United States Patent
Boone et al.

(10) Patent No.: US 7,371,559 B2
(45) Date of Patent: May 13, 2008

(54) PEPTIDES AND RELATED MOLECULES THAT MODULATE NERVE GROWTH FACTOR ACTIVITY

(75) Inventors: Thomas C. Boone, Newbury Park, CA (US); Kenneth C. Wild, Simi Valley, CA (US); Karen C. Sitney, Studio City, CA (US); Hosung Min, Newbury Park, CA (US); Bruce Kimmel, San Diego, CA (US)

(73) Assignee: Amgen Inc., Thousand Oaks, CA (US)

( * ) Notice: Subject to any disclaimer, the term of this patent is extended or adjusted under 35 U.S.C. 154(b) by 287 days.

(21) Appl. No.: 11/127,702

(22) Filed: May 11, 2005

(65) Prior Publication Data

US 2005/0222035 A1    Oct. 6, 2005

Related U.S. Application Data

(62) Division of application No. 10/666,480, filed on Sep. 18, 2003, now Pat. No. 6,919,426.

(60) Provisional application No. 60/412,524, filed on Sep. 19, 2002.

(51) Int. Cl.
   C12N 1/21    (2006.01)
   C12N 1/19    (2006.01)
   C12N 15/63   (2006.01)
   C12N 5/10    (2006.01)
   C07H 21/04   (2006.01)

(52) U.S. Cl. .............. 435/252.33; 435/254.11; 435/320.1; 435/325; 536/23.5

(58) Field of Classification Search .............. None
   See application file for complete search history.

(56) References Cited

U.S. PATENT DOCUMENTS 6,660,843 B1    12/2003    Feige et al.

FOREIGN PATENT DOCUMENTS

| WO | WO96/32478  | 10/1996 |
| WO | WO97/34631  | 9/1997  |
| WO | WO 99/53055 | 10/1999 |
| WO | WO00/24782  | 5/2000  |
| WO | WO 01/78698 | 10/2001 |

OTHER PUBLICATIONS

Ramer, M.S., et al., Adrenergic innervation of rat sensory ganglia following proximal or distal painful sciatic neuropathy: distinct mechanisms revealed by anti-NGF treatment. Eur J Neurosci 11:837-846 (1999).
Ro, L.S., et al., Effect of NGF and anti-NGF on neuropathic pain in rats following chronic constriction injury of the sciatic nerve. Pain 79: 265-274 (1999).

*Primary Examiner*—Maryam A. Monshipouri
*Assistant Examiner*—Marsha Tsay
(74) *Attorney, Agent, or Firm*—Lawrence B. Bugaisky

(57) ABSTRACT

The present invention relates to certain biologically active peptides and polypeptides which can be used as therapeutics or prophylactics against diseases or disorders linked to NGF as the causative agent. In one aspect of the present invention, pharmacologically active polypeptides comprising peptides linked to one or more Fc domains are provided.

7 Claims, 9 Drawing Sheets

FIG. 2A

```
    ATGGACAAAACTCACACATGTCCACCTTGTCCAGCTCCGGAACTCCTGGGGGGACCGTCA
1   ---------+---------+---------+---------+---------+---------+  60
    TACCTGTTTTGAGTGTGTACAGGTGGAACAGGTCGAGGCCTTGAGGACCCCCCTGGCAGT

M  D  K  T  H  T  C  P  P  C  P  A  P  E  L  L  G  G  P  S

GTCTTCCTCTTCCCCCCAAAACCCAAGGACACCCTCATGATCTCCCGGACCCCTGAGGTC
61  ---------+---------+---------+---------+---------+---------+  120
    CAGAAGGAGAAGGGGGGTTTTGGGTTCCTGTGGGAGTACTAGAGGGCCTGGGGACTCCAG

V  F  L  F  P  P  K  P  K  D  T  L  M  I  S  R  T  P  E  V

ACATGCGTGGTGGTGGACGTGAGCCACGAAGACCCTGAGGTCAAGTTCAACTGGTACGTG
121 ---------+---------+---------+---------+---------+---------+  180
    TGTACGCACCACCACCTGCACTCGGTGCTTCTGGGACTCCAGTTCAAGTTGACCATGCAC

T  C  V  V  V  D  V  S  H  E  D  P  E  V  K  F  N  W  Y  V

GACGGCGTGGAGGTGCATAATGCCAAGACAAAGCCGCGGGAGGAGCAGTACAACAGCACG
181 ---------+---------+---------+---------+---------+---------+  240
    CTGCCGCACCTCCACGTATTACGGTTCTGTTTCGGCGCCCTCCTCGTCATGTTGTCGTGC

D  G  V  E  V  H  N  A  K  T  K  P  R  E  E  Q  Y  N  S  T

TACCGTGTGGTCAGCGTCCTCACCGTCCTGCACCAGGACTGGCTGAATGGCAAGGAGTAC
241 ---------+---------+---------+---------+---------+---------+  300
    ATGGCACACCAGTCGCAGGAGTGGCAGGACGTGGTCCTGACCGACTTACCGTTCCTCATG

Y  R  V  V  S  V  L  T  V  L  H  Q  D  W  L  N  G  K  E  Y

AAGTGCAAGGTCTCCAACAAAGCCCTCCCAGCCCCCATCGAGAAAACCATCTCCAAAGCC
301 ---------+---------+---------+---------+---------+---------+  360
    TTCACGTTCCAGAGGTTGTTTCGGGAGGGTCGGGGGTAGCTCTTTTGGTAGAGGTTTCGG

K  C  K  V  S  N  K  A  L  P  A  P  I  E  K  T  I  S  K  A

AAAGGGCAGCCCCGAGAACCACAGGTGTACACCCTGCCCCCATCCCGGGATGAGCTGACC
361 ---------+---------+---------+---------+---------+---------+  420
    TTTCCCGTCGGGGCTCTTGGTGTCCACATGTGGGACGGGGGTAGGGCCCTACTCGACTGG

K  G  Q  P  R  E  P  Q  V  Y  T  L  P  P  S  R  D  E  L  T

AAGAACCAGGTCAGCCTGACCTGCCTGGTCAAAGGCTTCTATCCCAGCGACATCGCCGTG
421 ---------+---------+---------+---------+---------+---------+  480
    TTCTTGGTCCAGTCGGACTGGACGGACCAGTTTCCGAAGATAGGGTCGCTGTAGCGGCAC

```
      GAGTGGGAGAGCAATGGGCAGCCGGAGAACAACTACAAGACCACGCCTCCCGTGCTGGAC
481   ---------+---------+---------+---------+---------+---------+ 540
      CTCACCCTCTCGTTACCCGTCGGCCTCTTGTTGATGTTCTGGTGCGGAGGGCACGACCTG

E   W   E   S   N   G   Q   P   E   N   N   Y   K   T   T   P   P   V   L   D

TCCGACGGCTCCTTCTTCCTCTACAGCAAGCTCACCGTGGACAAGAGCAGGTGGCAGCAG
541   ---------+---------+---------+---------+---------+---------+ 600
      AGGCTGCCGAGGAAGAAGGAGATGTCGTTCGAGTGGCACCTGTTCTCGTCCACCGTCGTC

S   D   G   S   F   F   L   Y   S   K   L   T   V   D   K   S   R   W   Q   Q

GGGAACGTCTTCTCATGCTCCGTGATGCATGAGGCTCTGCACAACCACTACACGCAGAAG
601   ---------+---------+---------+---------+---------+---------+ 660
      CCCTTGCAGAAGAGTACGAGGCACTACGTACTCCGAGACGTGTTGGTGATGTGCGTCTTC

G   N   V   F   S   C   S   V   M   H   E   A   L   H   N   H   Y   T   Q   K

AGCCTCTCCCTGTCTCCGGGTAAA
661   ---------+---------+---- 684
      TCGGAGAGGGACAGAGGCCCATTT

```
XbaI                              NdeI ApaLI
 |                                  |    |
  TCTAGATTTGTTTTAACTAATTAAAGGAGGAATAACATATGGGTGCACAGAAAGCGGCCG
1 ---------+---------+---------+---------+---------+---------+ 60
  AGATCTAAACAAAATTGATTAATTTCCTCCTTATTGTATACCCACGTGTCTTTCGCCGGC

XhoI
       |
   CAAAAAAACTCGAGGGTGGAGGCGGTGGGGACAAAACTCACACATGTCCACCTTGCCCAG
61 ---------+---------+---------+---------+---------+---------+ 120
   GTTTTTTTGAGCTCCCACCTCCGCCACCCCTGTTTTGAGTGTGTACAGGTGGAACGGGTC

CACCTGAACTCCTGGGGGGACCGTCAGTTTTCCTCTTCCCCCCAAAACCCAAGGACACCC
121 ---------+---------+---------+---------+---------+---------+ 180
    GTGGACTTGAGGACCCCCCTGGCAGTCAAAAGGAGAAGGGGGGTTTTGGGTTCCTGTGGG

TCATGATCTCCCGGACCCCTGAGGTCACATGCGTGGTGGTGGACGTGAGCCACGAAGACC
181 ---------+---------+---------+---------+---------+---------+ 240
    AGTACTAGAGGGCCTGGGGACTCCAGTGTACGCACCACCACCTGCACTCGGTGCTTCTGG

CTGAGGTCAAGTTCAACTGGTACGTGGACGGCGTGGAGGTGCATAATGCCAAGACAAAGC
241 ---------+---------+---------+---------+---------+---------+ 300
    GACTCCAGTTCAAGTTGACCATGCACCTGCCGCACCTCCACGTATTACGGTTCTGTTTCG

CGCGGGAGGAGCAGTACAACAGCACGTACCGTGTGGTCAGCGTCCTCACCGTCCTGCACC
301 ---------+---------+---------+---------+---------+---------+ 360
    GCGCCCTCCTCGTCATGTTGTCGTGCATGGCACACCAGTCGCAGGAGTGGCAGGACGTGG

AGGACTGGCTGAATGGCAAGGAGTACAAGTGCAAGGTCTCCAACAAAGCCCTCCCAGCCC
361 ---------+---------+---------+---------+---------+---------+ 420
    TCCTGACCGACTTACCGTTCCTCATGTTCACGTTCCAGAGGTTGTTTCGGGAGGGTCGGG

CCATCGAGAAAACCATCTCCAAAGCCAAAGGGCAGCCCCGAGAACCACAGGTGTACACCC
421 ---------+---------+---------+---------+---------+---------+ 480
    GGTAGCTCTTTTGGTAGAGGTTTCGGTTTCCCGTCGGGGCTCTTGGTGTCCACATGTGGG

TGCCCCCATCCCGGGATGAGCTGACCAAGAACCAGGTCAGCCTGACCTGCCTGGTCAAAG
481 ---------+---------+---------+---------+---------+---------+ 540
    ACGGGGGTAGGGCCCTACTCGACTGGTTCTTGGTCCAGTCGGACTGGACGGACCAGTTTC
```

FIG. 3B

```
    GCTTCTATCCCAGCGACATCGCCGTGGAGTGGGAGAGCAATGGGCAGCCGGAGAACAACT
541 ---------+---------+---------+---------+---------+---------+ 600
    CGAAGATAGGGTCGCTGTAGCGGCACCTCACCCTCTCGTTACCCGTCGGCCTCTTGTTGA

ACAAGACCACGCCTCCCGTGCTGGACTCCGACGGCTCCTTCTTCCTCTACAGCAAGCTCA
601 ---------+---------+---------+---------+---------+---------+ 660
    TGTTCTGGTGCGGAGGGCACGACCTGAGGCTGCCGAGGAAGAAGGAGATGTCGTTCGAGT

CCGTGGACAAGAGCAGGTGGCAGCAGGGGAACGTCTTCTCATGCTCCGTGATGCATGAGG
661 ---------+---------+---------+---------+---------+---------+ 720
    GGCACCTGTTCTCGTCCACCGTCGTCCCCTTGCAGAAGAGTACGAGGCACTACGTACTCC

BamHI
                                                           |
    CTCTGCACAACCACTACACGCAGAAGAGCCTCTCCCTGTCTCCGGGTAAATAATGGATCC
721 ---------+---------+---------+---------+---------+---------+ 780
    GAGACGTGTTGGTGATGTGCGTCTTCTCGGAGAGGGACAGAGGCCCATTTATTACCTAGG
```

FIG. 4A

```
     XbaI                          NdeI
       |                             |
       TCTAGATTTGTTTTAACTAATTAAAGGAGGAATAACATATGGACAAAACTCACACATGTC
   1   ---------+---------+---------+---------+---------+---------+  60
       AGATCTAAACAAAATTGATTAATTTCCTCCTTATTGTATACCTGTTTTGAGTGTGTACAG

CACCTTGTCCAGCTCCGGAACTCCTGGGGGGACCGTCAGTCTTCCTCTTCCCCCCAAAAC
  61   ---------+---------+---------+---------+---------+---------+ 120
       GTGGAACAGGTCGAGGCCTTGAGGACCCCCCTGGCAGTCAGAAGGAGAAGGGGGGTTTTG

CCAAGGACACCCTCATGATCTCCCGGACCCCTGAGGTCACATGCGTGGTGGTGGACGTGA
 121   ---------+---------+---------+---------+---------+---------+ 180
       GGTTCCTGTGGGAGTACTAGAGGGCCTGGGGACTCCAGTGTACGCACCACCACCTGCACT

GCCACGAAGACCCTGAGGTCAAGTTCAACTGGTACGTGGACGGCGTGGAGGTGCATAATG
 181   ---------+---------+---------+---------+---------+---------+ 240
       CGGTGCTTCTGGGACTCCAGTTCAAGTTGACCATGCACCTGCCGCACCTCCACGTATTAC

CCAAGACAAAGCCGCGGGAGGAGCAGTACAACAGCACGTACCGTGTGGTCAGCGTCCTCA
 241   ---------+---------+---------+---------+---------+---------+ 300
       GGTTCTGTTTCGGCGCCCTCCTCGTCATGTTGTCGTGCATGGCACACCAGTCGCAGGAGT

CCGTCCTGCACCAGGACTGGCTGAATGGCAAGGAGTACAAGTGCAAGGTCTCCAACAAAG
 301   ---------+---------+---------+---------+---------+---------+ 360
       GGCAGGACGTGGTCCTGACCGACTTACCGTTCCTCATGTTCACGTTCCAGAGGTTGTTTC

CCCTCCCAGCCCCCATCGAGAAAACCATCTCCAAAGCCAAAGGGCAGCCCCGAGAACCAC
 361   ---------+---------+---------+---------+---------+---------+ 420
       GGGAGGGTCGGGGGTAGCTCTTTTGGTAGAGGTTTCGGTTTCCCGTCGGGGCTCTTGGTG

AGGTGTACACCCTGCCCCCATCCCGGGATGAGCTGACCAAGAACCAGGTCAGCCTGACCT
 421   ---------+---------+---------+---------+---------+---------+ 480
       TCCACATGTGGGACGGGGGTAGGGCCCTACTCGACTGGTTCTTGGTCCAGTCGGACTGGA

GCCTGGTCAAAGGCTTCTATCCCAGCGACATCGCCGTGGAGTGGGAGAGCAATGGGCAGC
 481   ---------+---------+---------+---------+---------+---------+ 540
       CGGACCAGTTTCCGAAGATAGGGTCGCTGTAGCGGCACCTCACCCTCTCGTTACCCGTCG

CGGAGAACAACTACAAGACCACGCCTCCCGTGCTGGACTCCGACGGCTCCTTCTTCCTCT
 541   ---------+---------+---------+---------+---------+---------+ 600
       GCCTCTTGTTGATGTTCTGGTGCGGAGGGCACGACCTGAGGCTGCCGAGGAAGAAGGAGA
```

FIG. 4B

```
    ACAGCAAGCTCACCGTGGACAAGAGCAGGTGGCAGCAGGGGAACGTCTTCTCATGCTCCG
601 ---------+---------+---------+---------+---------+---------+ 660
    TGTCGTTCGAGTGGCACCTGTTCTCGTCCACCGTCGTCCCCTTGCAGAAGAGTACGAGGC

TGATGCATGAGGCTCTGCACAACCACTACACGCAGAAGAGCCTCTCCCTGTCTCCGGGTA
661 ---------+---------+---------+---------+---------+---------+ 720
    ACTACGTACTCCGAGACGTGTTGGTGATGTGCGTCTTCTCGGAGAGGGACAGAGGCCCAT

ApaLI                         XhoI      BamHI
                |                             |         |
    AAGGTGGAGGTGGTGGTGCACAGAAAGCGGCCGCAAAAAAACTCGAGTAATGGATCC
721 ---------+---------+---------+---------+---------+------- 777
    TTCCACCTCCACCACCACGTGTCTTTCGCCGGCGTTTTTTTGAGCTCATTACCTAGG
```

PEPTIDES AND RELATED MOLECULES THAT MODULATE NERVE GROWTH FACTOR ACTIVITY

This application is a divisional of application Ser. No. 10/666,480 filed Sep. 18, 2003, now U.S. Pat. No. 6,919,426 B2, which claims the benefit of U.S. Provisional Application No. 60/412,524, filed Sep. 19, 2002, both of which are hereby incorporated by reference.

BACKGROUND OF THE INVENTION

More than two million people in the United States alone are incapacitated by chronic pain on any given day (T. M. Jessell & D. D. Kelly, Pain and Analgesia in PRINCIPLES OF NEURAL SCIENCE, third edition (E. R. Kandel, J. H. Schwartz, T. M. Jessell, ed., (1991)). Unfortunately, current treatments for pain are only partially effective, and many also cause debilitating or dangerous side effects. For example, non-steroidal anti-inflammatory drugs ("NSAIDs") such as aspirin, ibuprofen, and indomethacin are moderately effective against inflammatory pain but they are also renal toxins, and high doses tend to cause gastrointestinal irritation, ulceration, bleeding, and confusion. Patients treated with opioids frequently experience confusion, and long-term opioid use is associated with tolerance and dependence. Local anesthetics such as lidocaine and mixelitine simultaneously inhibit pain and cause loss of normal sensation.

Pain is a perception based on signals received from the environment and transmitted and interpreted by the nervous system (for review, see Millan, M. J., The induction of pain: an integrative review. Prog Neurobiol 57:1-164 (1999)). Noxious stimuli such as heat and touch cause specialized sensory receptors in the skin to send signals to the central nervous system ("CNS"). This process is called nociception, and the peripheral sensory neurons that mediate it are nociceptors. Depending on the strength of the signal from the nociceptor(s) and the abstraction and elaboration of that signal by the CNS, a person may or may not experience a noxious stimulus as painful. When one's perception of pain is properly calibrated to the intensity of the stimulus, pain serves its intended protective function. However, certain types of tissue damage cause a phenomenon, known as hyperalgesia or pronociception, in which relatively innocuous stimuli are perceived as intensely painful because the person's pain thresholds have been lowered. Both inflammation and nerve damage can induce hyperalgesia. Thus, persons afflicted with inflammatory conditions, such as sunburn, osteoarthritis, colitis, carditis, dermatitis, myositis, neuritis, collagen vascular diseases (which include rheumatoid arthritis and lupus) and the like, often experience enhanced sensations of pain. Similarly, trauma, surgery, amputation, abscess, causalgia, collagen vascular diseases, demyelinating diseases, trigeminal neuralgia, cancer, chronic alcoholism, stroke, thalamic pain syndrome, diabetes, herpes infections, acquired immune deficiency syndrome ("AIDS"), toxins and chemotherapy cause nerve injuries that result in excessive pain.

As the mechanisms by which nociceptors transduce external signals under normal and hyperalgesic conditions become better understood, processes implicated in hyperalgesia can be targeted to inhibit the lowering of the pain threshold and thereby lessen the amount of pain experienced.

Neurotrophic factors have been shown to play significant roles in the transmission of physiologic and pathologic pain. Nerve growth factor (NGF) appears to be particularly important (for review, see McMahon, S. B., NGF as a mediator of inflammatory pain, Phil Trans R Soc Lond 351:431-40 (1996); and Apfel, S. C., Neurotrophic Factors and Pain, The Clinical Journal of Pain 16:S7-S11 (2000)). Both local and systemic administration of NGF have been shown to elicit hyperalgesia and allodynia (Lewin, et al., Peripheral and central mechanisms of NGF-induced hyperalgesia. Eur. J. Neurosci. 6:1903-1912 (1994)). Intravenous infusion of NGF in humans produces a whole body myalgia while local administration evokes injection site hyperalgesia and allodynia in addition to the systemic effects (Apfel, et al., Recombinant human nerve growth factor in the treatment of diabetic polyneuropathy. Neurology 51: 695-702 (1998)). There is also a considerable body of evidence implicating endogenous NGF in conditions in which pain is a prominent feature. For example, NGF is upregulated in DRG Schwann cells for at least 2 months following peripheral nerve injury and increased levels have been reported in the joints of animals suffering from a variety of models of arthritis (e.g., Aloe, et al., The synovium of transgenic arthritic mice expressing human tumor necrosis factor contains a high level of nerve growth factor. Growth Factors 9:149-155 (1993)). In humans, NGF levels are elevated in synovial fluid from patients with rheumatoid or other types of arthritis (e.g., Aloe et al., Nerve growth factor in the synovial fluid of patients with chronic arthritis. Arthritis and Rheumatism 35:351-355 (1992)). Furthermore, it has been demonstrated that antagonism of NGF function prevents hyperalgesia and allodynia in models of neuropathic and chronic inflammatory pain. For example, in models of neuropathic pain (e.g. nerve trunk or spinal nerve ligation) systemic injection of neutralizing antibodies to NGF prevents both allodynia and hyperalgesia (Ramer, M. S., et al., Adrenergic innervation of rat sensory ganglia following proximal or distal painful sciatic neuropathy: distinct mechanisms revealed by anti-NGF treatment. Eur J Neurosci 11:837-846 (1999); and Ro, L. S., et al., Effect of NGF and anti-NGF on neuropathic pain in rats following chronic constriction injury of the sciatic nerve. Pain 79: 265-274 (1999)).

Clearly, there is a need for new safe and effective treatments for pain. It is an object of the present invention to provide novel binding agents of NGF that modulate NGF activity and that are useful for managing pain. Such agents of the present invention take the form of NGF binding peptides and NGF binding modified peptides, i.e., peptides fused to other molecules such as an Fc portion of an antibody, where the peptide moiety specifically binds to NGF.

SUMMARY OF THE INVENTION

The present invention concerns novel agents which bind to and modulate the activity of nerve growth factor (NGF).

In accordance with the present invention, modifiers of NGF activity comprise an amino acid sequence of the following formula:

$$a^1 a^2 a^3 C a^5 a^6 a^7 a^8 a^9 a^{10} a^{11} L Q S C a^{16} a^{17} a^{18} \quad \text{(SEQ ID NO: 276)}$$

wherein:

$a^1, a^2, a^3, a^5, a^6, a^8$ and $a^{18}$ are each independently absent or amino acid residues;

$a^7$ is a neutral hydrophobic or polar hydrophobic amino acid residue;

$a^9$ is a neutral hydrophobic or polar hydrophobic amino acid residue;

$a^{10}$ is a neutral hydrophobic, neutral polar, or a basic amino acid residue;

$a^{11}$ is a neutral hydrophobic, neutral polar, or a basic amino acid residue;

$a_{16}$ is a neutral hydrophobic amino acid residue;

$a^{17}$ is a neutral hydrophobic or polar hydrophobic amino acid residue; or a physiologically acceptable salt thereof, and wherein said peptide is capable of modulating NGF activity.

Also in accordance with the present invention are NGF activity modulating peptides comprising an amino acid sequence of the formula:

$$b^1b^2b^3CWb^6b^7b^8b^9GCb^{12}b^{13}b^{14}$$ (SEQ ID NO: 274)

wherein:

$b^1$, $b^2$, $b^3$, $b^8$, $b^9$, $b^{13}$ and $b^{14}$ are each independently absent or amino acid residues;

$b^6$ is a neutral hydrophobic amino acid residue;

$b^7$ is a polar hydrophobic amino acid residue;

$b^{12}$ is a neutral hydrophobic or an acidic amino acid residue; or a physiologically acceptable salt thereof, and wherein said peptide is capable of modulating NGF activity.

Further in accordance with the present invention are NGF activity modulating peptides of the formula:

$$c^1c^2QCc^5c^6Sc^8c^9GCc^{12}c^{13}c^{14}c^{15}c^{16}$$

wherein:

$c^1$, $c^5$, $c^8$, $c^9$, $c^{13}$ and $c^{14}$ are each independently absent or amino acid residues;

$c^2$ is a neutral hydrophobic amino acid residue;

$c^6$ is a neutral hydrophobic or polar hydrophopic amino acid residue;

$c^{12}$ is a neutral hydrophobic or an acidic amino acid residue; or a physiologically acceptable salt thereof, and wherein said peptide is capable of modulating NGF activity.

Further in accordance with the present invention are NGF activity modulating peptides comprising an amino acid sequence of the formula:

$$d^1d^2d^3d^4d^5d^6d^7PPd^{10}d^{11}d^{12}d^{13}d^{14}d^{15}Pd^{17}d^{18}d^{19}d^{20}d^{21}d^{22}d^{23}d^{24}$$

wherein:

$d^1$ is a W, Y, Q, or E;

$d^2$ is a V, L, F, S, or Q;

$d^3$ is a W, F, G, S, or Q;

$d^4$ is a A, Q, D, E, or K;

$d^5$ is a V, W, G, or R;

$d^6$ is a M, S, Y, Q, N, E, K, or R;

$d^7$ is a A, V, L, P, W, Q, or H;

$d^{10}$ is a D or E;

$d^{11}$ is a V or I;

$d^{12}$ is a V, L, F, or Y;

$d^{13}$ is a V, L, G, Q, or E;

$d^{14}$ is a Q, D, or E;

$d^{15}$ is a W or C;

$d^{17}$ is a W, Y, or Q;

$d^{18}$ is a V, T, Q, N, or K;

$d^{19}$ is a A, L, or P;

$d^{20}$ is a P, Q, R, or H;

$d^{21}$ is a V, I, W, D;

$d^{22}$ is a A, I, S, Q, or D;

$d^{23}$ is a L or absent;

$d^{24}$ is a E or absent; or a physiologically acceptable salt thereof, and wherein said peptide is capable of modulating NGF activity.

Other aspects of the invention are peptides comprising an amino acid sequence of the formula:

$$f^1f^2f^3f^4f^5f^6f^7f^8f^9f^{10}f^{11}Lf^{13}EQYFf^{18}Lf^{20}PPGf^{24}f^{25}f^{26}$$

wherein:

$f^1$-$f^6$, $f^8$, $f^9$, $f^{11}$, $f^{18}$, $f^{24}$, $f^{25}$ and $f^{26}$ are each independently absent or amino acid residues;

$f^7$, $f^{10}$, and $f^{13}$ are each independently neutral hydrophobic or polar hydrophopic amino acid residues;

$f^{20}$ is a T, M, or I; or a physiologically acceptable salt thereof, and wherein said peptide is capable of modulating NGF activity.

Further in accordance with the present invention are peptides comprising an amino acid sequence of the formula:

$$h^1h^2h^3h^4h^5h^6LGh^9h^{10}h^{11}Lh^{13}YFh^{16}Lh^{18}PPGh^{22}h^{23}h^{24}$$

wherein:

$h^1$-$h^6$, $h^9$, $h^{11}$, $h^{23}$, and $h^{24}$ are each independently absent or amino acid residues;

$h^{10}$ and $h^{13}$ are each independently neutral hydrophobic or polar hydrophopic amino acid residues;

$h^{16}$ is a polar hydrophopic or basic amino acid residue;

$h^{18}$ is a neutral hydrophopic amino acid residue;

$h^{22}$ is a neutral polar amino acid residue; or a physiologically acceptable salt thereof, and wherein said peptide is capable of modulating NGF activity.

Another aspect of the invention includes a pharmacologically active peptide (P) comprising an amino acid sequence selected from the group consisting of:
 i. SEQ ID NO: 1 to SEQ ID NO: 58, inclusive;
 ii. SEQ ID NO: 202 to SEQ ID NO: 280, inclusive;
 iii. an analog of (i) or (ii);
 iv. a derivative of (i), (ii) or (iii);
 v. a multimer of (i), (ii), (iii), or (iv); and
 vi. a physiologically acceptable salt of (i), (ii), (iii), (iv), or (v), wherein said peptide is capable of inhibiting NGF activity.

Another aspect of the invention comprises a composition of matter of the formula:

$$(X^1)_a\text{-}F^1\text{-}(X^2)_b \qquad (I)$$

and multimers thereof, wherein:

$F^1$ is a vehicle (preferably an Fc domain);

$X^1$ and $X^2$ are each independently selected from -(L$^1$)$_c$-P$^1$, -(L$^1$)$_c$-P$^1$-(L$^2$)$_d$-P$^2$, -(L$^1$)$_c$-P$^1$-(L$^2$)$_d$-P$^2$-(L$^3$)$_e$-P$^3$, and -(L$^1$)$_c$-P$^1$-(L$^2$)$_d$-P$^2$-(L$^3$)$_e$-P$^3$-(L$^4$)$_f$-P$^4$;

$L^1$, $L^2$, $L^3$, and $L^4$ are each independently linkers;

a, b, c, d, e, and f are each independently 0 or 1, provided that at least one of a and b is 1; and $P^1$, $P^2$, $P^3$, and $P^4$ are each independently sequences of pharmacologically active peptides selected from the group consisting of:
 i. SEQ ID NO: 1 to SEQ ID NO: 58, inclusive;
 ii. SEQ ID NO: 202 to SEQ ID NO: 280, inclusive;
 iii. an analog of (i) or (ii);
 iv. a derivative of (i), (ii) or (iii); and
 v. a physiologically acceptable salt of (i), (ii), (iii), or (iv), and wherein said composition of matter is capable of modulating NGF activity.

The peptides and modified peptides of the invention may be prepared by standard synthetic methods, recombinant DNA techniques, or any other methods of preparing peptides and fusion proteins.

Modified peptides of the invention that encompass non-peptide portions may be synthesized by standard organic chemistry reactions, in addition to standard peptide chemistry reactions when applicable.

The peptides and modified peptides of the invention have therapeutic value for the treatment of chronic pain states of neuropathic or inflammatory origin, and can also be used to treat other diseases linked to NGF as a causative agent, including, but not limited to, migraine, asthma, urge incontinence (i.e., hyperactive bladder), psoriasis, and cancer (especially, pancreatic cancer and melanoma).

The peptides and modified peptides of the invention may be used for therapeutic or prophylactic purposes by formulating them with appropriate pharmaceutical carrier materials and administering an effective amount to a patient, such as a human (or other mammal) in need thereof.

Additional useful peptides and modified peptides may result from conservative modifications of the amino acid of the peptides and modified peptides disclosed herein. Conservative modifications will produce peptides and modified peptides having functional, physical, and chemical characteristics similar to those of the peptide or modified peptide from which such modifications are made.

Additional aspects and advantages of the present invention will become apparent upon consideration of the detailed description of the invention which follows.

BRIEF DESCRIPTION OF THE FIGURES

FIG. 1 shows the structure of a typical or preferred modified peptide of the invention. "Fc" in this figure represents any of the Fc variants within the meaning of "Fc domain" herein. The modified peptide is comprised of a homodimer comprised of two Fc monomers, each with one attached peptide. The purified "dimer" possesses twelve cysteine residues which form two intermolecular and four intramolecular disulfide bonds as depicted.

FIG. 2 shows exemplary nucleic acid and amino acid sequences (SEQ ID NOS: 59 and 60, respectively) of human IgG1 Fc that may be used in the invention.

FIG. 3A-B shows the double stranded DNA sequence (SEQ ID NOs: 61 and 62, top/sense and bottom/anti-sense strands, respectively) of an Fc N-terminal vector inserted into expression plasmid pAMG21 between the NdeI restriction site (position #5675 in pAMG21) and BamHI restriction site (position #5745 in pAMG21), resulting in an expression plasmid capable of expressing peptide-Fc fusion proteins in accordance with the invention.

FIG. 4A-B shows the double stranded DNA sequence (SEQ ID NOS: 121 and 122, top/sense and bottom/anti-sense strands, respectively) of an Fc C-terminal vector inserted into expression plasmid pAMG21 between the NdeI restriction site (position #5675 in pAMG21) and BamHI restriction site (position #5745 in pAMG21), resulting in an expression plasmid capable of expressing peptide-Fc fusion proteins in accordance with the invention.

DETAILED DESCRIPTION OF THE INVENTION

Figure 1A:
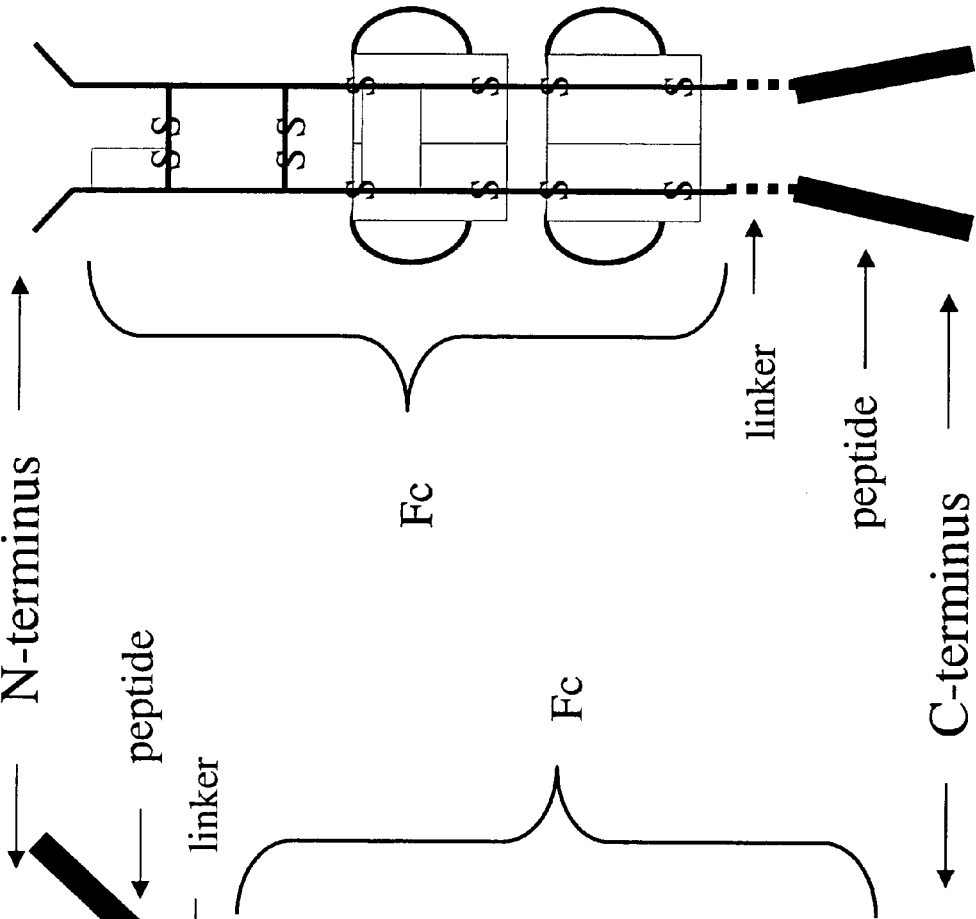
FIG. 1A shows a molecule in which the linker-peptide portion is present as single chains extending from the N-terminus of the Fc domain.
Figure 1B:
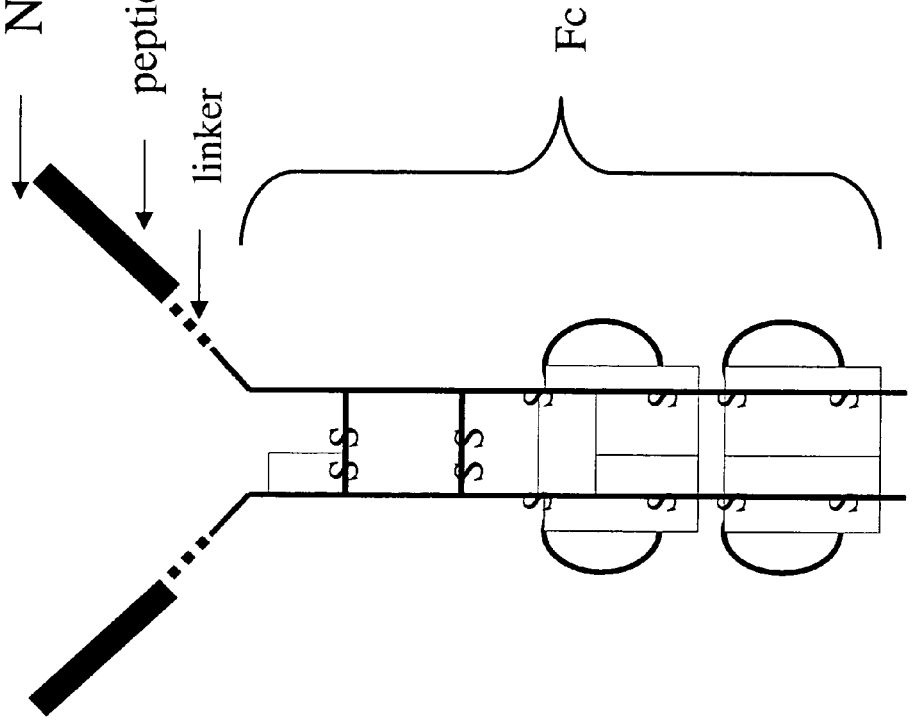
FIG. 1B shows a molecule in which the linker-peptide portion is present as single chains extending from the C-terminus of the Fc domain.

The terms used throughout this specification are defined as follows, unless otherwise limited in specific instances.

Amino acid residues are discussed in three ways: full name of the amino acid, standard three-letter code, or standard single-letter code in accordance with the chart shown below.

| A = Ala | G = Gly | M = Met | S = Ser |
|---------|---------|---------|---------|
| C = Cys | H = His | N = Asn | T = Thr |
| D = Asp | I = Ile | P = Pro | V = Val |
| E = Glu | K = Lys | Q = Gln | W = Trp |
| F = Phe | L = Leu | R = Arg | Y = Tyr |

The term "comprising" means that a peptide or modified peptide may include additional amino acids on either or both of the N- or C-termini of the given sequence. Of course, these additional amino acids should not significantly interfere with the activity of the peptide or modified peptide.

Modifications can protect therapeutic peptides and proteins, primarily by blocking their exposure to proteolytic enzymes, leading to increased stability, circulation time and biological activity of the therapeutic molecule. A review article describing protein modification and fusion proteins is Francis, Focus on Growth Factors Volume 3, pages 4-10, published by Mediscript, London (1992), which is hereby incorporated by reference.

One useful protein modification is a combination with the "Fc" domain of an antibody. Antibodies comprise two functionally independent parts, a variable domain known as "Fab", which binds antigen, and a constant domain known as "Fc", which links to such effector functions as complement activation and attack by phagocytic cells. An Fc domain has a long serum half-life, whereas a Fab is short-lived. Capon et al., Nature, Volume 337, pages 525-31 (1989). When constructed together with a therapeutic protein, an Fc domain can provide longer half-life or incorporate such functions as Fc receptor binding, protein A binding, complement fixation, and perhaps even placental transfer.

As used herein, the term "native Fc" refers to a molecule or sequence comprising the sequence of a non-antigen-binding fragment resulting from chemical or enzymatic digestion of whole antibody. The original immunoglobulin source of the native Fc is preferably of human origin and may be any of the immunoglobulins, although IgG1 and IgG2 are preferred. Native Fc domains are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgA2). One example of a native Fc is a disulfide-bonded dimer resulting from papain digestion of an IgG; see Ellison et al., Nucleic Acids Res., Volume 10, pages 4071-4079 (1982).

The term "Fc variant" refers to a molecule or sequence that is modified from a native Fc but still comprises a binding site for the salvage receptor, FcRn. International applications WO 97/34631 and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" and the term "Fc" are intended to encompass native Fc and Fc variant molecules and sequences as defined above.

Published International Patent Application WO 00/24782 describes fusion proteins comprising Fc antibody domains linked to biologically active peptides and their use as pharmaceutical agents. Linkage of the peptides to the Fc domains is disclosed as increasing the half-life of the peptide, which would otherwise be quickly degraded in vivo. The peptides can be selected by phage display, E. coli display, ribosome display, RNA-peptide screening or chemical-peptide screening. Specifically exemplified are Fc fusion products made from peptide mimetics of TPO (megakaryocyte growth and differentiation factor) and peptide inhibitors of TNF-α, IL-1 and VEGF, among others.

The terms "derivatizing" and "derivative" or "derivatized" comprise processes and resulting peptides or modified peptides, respectively, in which (1) the peptide or modified peptide has a cyclic portion; for example, cross-linking between cysteinyl residues within the modified peptide; (2) the peptide or modified peptide is cross-linked or has a cross-linking site; for example, the peptide or modified peptide has a cysteinyl residue and thus forms cross-linked dimers in culture or in vivo; (3) one or more peptidyl linkage is replaced by a non-peptidyl linkage; (4) the N-terminus is replaced by —NRR$^1$, NRC(O)R$^1$, —NRC(O)OR$^1$, —NRS(O)$_2$R$^1$, —NHC(O)NHR, a succinimide group, or substituted or unsubstituted benzyloxycarbonyl-NH—, wherein R and R$^1$ and the ring substituents are as defined hereinafter; (5) the C-terminus is replaced by —C(O)R$^2$ or —NR$^3$R$^4$ wherein R$^2$, R$^3$ and R$^4$ are as defined hereinafter; and (6) peptides or modified peptides in which individual amino acid moieties are modified through treatment with agents capable of reacting with selected side chains or terminal residues. Derivatives are further described hereinafter.

The term "NGF" means nerve growth factor.

The interaction of a protein ligand with its receptor often takes place at a relatively large interface. However, as demonstrated for human growth hormone and its receptor, only a few key residues at the interface contribute to most of the binding energy. Clackson et al., Science, Volume 267, pages 383-386 (1995). The bulk of the protein ligand merely displays the binding epitopes in the right topology or serves functions unrelated to binding. Thus, molecules of only "peptide" length can bind to the receptor protein of a given large protein ligand. Such peptides may mimic the bioactivity of the large protein ligand ("peptide agonists") or, through competitive binding, inhibit the bioactivity of the large protein ligand ("peptide antagonists").

The term "peptide" as used generally herein refers to molecules of 5 to 50 amino acids, with molecules of 5 to 20 amino acids being preferred and those of 6 to 15 amino acids being most preferred.

Phage display peptide libraries have emerged as a powerful method in identifying peptide agonists and peptide antagonists. See, for example, Scott et al., Science, Volume 249, page 386 (1990); Devlin et al. Science, Volume 249, page 404 (1990); U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated herein by reference). In such libraries, random peptide sequences are displayed by fusion with coat proteins of filamentous phage. Typically, the displayed peptides are affinity-eluted against an antibody-immobilized extracellular domain of a receptor. The retained phages may be enriched by successive rounds of affinity purification and repropagation. The best binding peptides may be sequenced to identify key residues within one or more structurally related families of peptides. See, for example, Cwirla et al., Science Volume 276, pages 1696-1699 (1997), in which two distinct families were identified. The peptide sequences may also suggest which residues may be safely replaced by alanine scanning or by mutagenesis at the DNA level. Mutagenesis libraries may be created and screened to further optimize the sequence of the best binders. Lowman, Ann. Rev. Biophys. Biomol. Struct., Volume 26, pages 401-424 (1997).

Structural analysis of protein-protein interaction may also be used to suggest peptides that mimic the binding activity of large protein ligands. In such an analysis, the crystal structure may suggest the identity and relative orientation of critical residues of the large protein ligand from which a peptide may be designed. See, for example, Takasaki et al., Nature Biotech., Volume 15, pages 1266-1270 (1997). These analytical methods may also be used to investigate the interaction between a receptor protein and peptides selected by phage display, which may suggest further modification of the peptides to increase binding affinity.

Other methods compete with phage display in peptide research. A peptide library can be fused to the carboxyl terminus of the lac repressor and expressed in E. coli. Another E. coli-based method allows display on the outer membrane of the cell by fusion with a peptidoglycan-associated lipoprotein (PAL). Hereinafter, these and related methods are collectively referred to as "E. coli display." In another method, translation of random RNA is halted prior to ribosome release, resulting in a library of polypeptides with their associated RNA still attached. Hereinafter, this and related methods are collectively referred to as "ribosome display." Still other methods employ chemical linkage of peptides to RNA; see, for example, Roberts and Szostak, Proc. Natl. Acad. Sci. USA, Volume 94, pages 12297-12303 (1997). Hereinafter, this and related methods are collectively referred to as "RNA-peptide screening." Chemically derived peptide libraries have also been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other unnatural analogs, as well as non-peptide elements. Both biological and chemical methods are reviewed in Wells and Lowman, Curr. Opin. Biotechnol., Volume 3, pages 355-362 (1992).

Conceptually, one may discover peptide mimetics of any protein using phage display, and the other methods mentioned above. These methods have been used for epitope mapping, for identification of critical amino acids in protein-protein interactions, and also as leads for the discovery of new therapeutic agents. For example, see Cortese et al., Curr. Opin. Biotech. Volume 7, pages 616-621 (1996). Peptide libraries are now being used most often in immunological studies, such as epitope mapping. Kreeger, The Scientist, Volume 10, Number 13, pages 19-20 (1996). Peptides are oftentimes regarded as "leads" in development of therapeutic agents rather than as therapeutic agents themselves. Like many other proteins, they would be rapidly removed in vivo by renal filtration, cellular clearance mechanisms in the reticulo-endothelial system, or proteolytic degradation. See Francis, Focus on Growth Factors, Volume 3, pages 4-11 (1992). As a result, the identified peptides are often used to validate drug targets or as scaffolds for design of organic modified peptides that might not have been as easily or as quickly identified through chemical library screening. Lowman, Ann. Rev. Biophys. Biomol. Struct., Volume 26, pages 401-424 (1997); Kay et al., Drug Disc. Today, Volume 3, pages 370-378(1998).

The term "pharmacologically active" means that a substance so described is determined to have activity that affects a medical parameter or disease state (for example, pain). In the context of the invention, this term typically refers to an NGF-induced or NGF-mediated disease or abnormal medical condition or disorder, and more specifically, to antagonism of pain.

The terms "antagonist" and "inhibitor" refer to a molecule that blocks or in some way interferes with the biological activity of the associated protein of interest. A preferred "antagonist" or "inhibitor" of the present invention is a molecule that binds to and inhibits NGF with an $IC_{50}$ of 20 nM or less in in vitro assays of NGF activity. A more preferred "antagonist" or "inhibitor" of the present invention is a molecule that binds to and inhibits NGF with an $IC_{50}$ of 1 nM or less in in vitro assays of NGF activity. A most preferred "antagonist" or "inhibitor" of the present invention is a molecule that binds to and inhibits NGF with an $IC_{50}$ of 20 nM or less in in vitro assays of NGF activity and prevents, ameliorates or abolishes pain as measured in at least one generally accepted in vivo animal model of neurological pain.

Additionally, physiologically acceptable salts of the modified peptides of the invention are also encompassed herein. By "physiologically acceptable salts" is meant any salts that are known or later discovered to be pharmaceutically acceptable (i.e., useful in the treatment of a warm-blooded animal). Some specific examples are: acetate; trifluoroacetate; hydrohalides, such as hydrochloride and hydrobromide; sulfate; citrate; tartrate; glycolate; and oxalate.

Structure of Modified Peptides

In General. With respect to the modified peptides of the present invention, the peptide portion may be attached to the vehicle (i.e., Fc domain) through the N-terminus and/or C-terminus of the peptide. Thus, the resulting vehicle-peptide composite may be described by the following formula:

$$(X^1)_a\text{-}F^1\text{-}(X^2)_b \quad \text{(I)}$$

wherein:

$F^1$ is a vehicle (preferably an Fc domain);

$X^1$ and $X^2$ are each independently selected from $-(L^1)_c\text{-}P^1$, $-(L^1)_c\text{-}P^1\text{-}(L^2)_d\text{-}P^2$, $-(L^1)_c\text{-}P^1\text{-}(L^2)_d\text{-}P^2\text{-}(L^3)_e\text{-}P^3$, and $-(L^1)_c\text{-}P^1\text{-}(L^2)_d\text{-}P^2\text{-}(L^3)_e\text{-}P^3\text{-}(L^4)_f\text{-}P^4$;

$L^1$, $L^2$, $L^3$, and $L^4$ are each independently linkers;

a, b, c, d, e, and f are each independently 0 or 1, provided that at least one of a and b is 1; and $P^1$, $P^2$, $P^3$, and $P^4$ are each independently a pharmacologically active peptide selected from the group consisting of:

i. SEQ ID NO: 1 to SEQ ID NO: 58, inclusive;
ii. SEQ ID NO: 202 to SEQ ID NO: 280, inclusive;
iii. an analog of (i) or (ii); and
iv. a derivative of (i), (ii) or (iii).

The modified peptides of formula I will comprise preferred embodiments of the formulas:

$$X^1\text{-}F^1 \quad \text{(II)}$$

wherein $F^1$ is an Fc domain and is attached at the C-terminus of $X^1$;

$$F^1\text{-}X^2 \quad \text{(III)}$$

wherein $F^1$ is an Fc domain and is attached at the N-terminus of $X^2$; and $$F^1\text{-}(L)_c\text{-}P \quad \text{(IV)}$$

wherein $F^1$ is an Fc domain and is attached at the N-terminus of $-(L)_c\text{-}P$.

In addition to the peptides (P) and the modified peptides provided by formulas (I)-(IV), also intended as part of the invention are fragments (i.e., "subsequences"), analogs, and derivatives of such peptides and modified peptides which are substantially equivalent with respect to in vitro and/or in vivo anti-NGF activity, including but not limited to, monomers or multimers of any of the peptides (P) disclosed herein.

The term "analog" is intended to mean molecules representing one or more amino acid substitutions, deletions and/or additions derived from the linear array of amino acids of the peptides (P) or the modified peptides provided for by (I)-(IV), and which are substantially equivalent with respect to in vitro and/or in vivo anti-NGF activity as compared to at least one analogous peptide or modified peptide specifically disclosed herein.

For the purposes of the invention, "substantially homologous" sequences are at least 81%, preferably at least 85%, more preferably at least 90%, and most preferably at least 91%, 92%, 93%, 94%, 95%, 96%, 97%, 98%, 99% identical, over any region of P of at least 10 amino acids, as determined by any of the alignment methods generally applied in the art (for example, the GAP program) and/or as discussed herein, even if the sequences differ more substantially outside of the P region.

Percent sequence identity can be determined by standard methods that are commonly used to compare the similarity in position of the amino acids of two polypeptides in order to generate an optimal alignment of two respective sequences. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., *SIAM J. Applied Math.*, 48:1073 (1988). Methods to determine identity and similarity are also described in publicly available computer programs. Preferred computer program methods to determine identity and similarity between two sequences include, but are not limited to, the GCG program package, including GAP (Devereux et al., *Nucl. Acid. Res.*, 12:387 (1984); Genetics Computer Group, University of Wisconsin, Madison, Wis.), BLASTP, BLASTN, and FASTA (Altschul et al., *J. Mol. Biol.*, 215:403-410 (1990)). The BLASTX program is publicly available from the National Center for Biotechnology Information (NCBI) and other sources (*BLAST Manual*, Altschul et al. NCB/NLM/NIH Bethesda, Md. 20894; Altschul et al., supra). The well known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full length sequences. Preferred methods to determine identity and/or similarity are designed to give the largest match between the sequences tested. For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., *Proc. Natl. Acad. Sci USA*, 89:10915-10919 (1992) for the BLOSUM 62 comparison matrix) is also used by the algorithm. Preferred parameters for a polypeptide sequence comparison include the following:

Algorithm: Needleman et al., *J. Mol. Biol.*, 48:443-453 (1970);
Comparison matrix: BLOSUM 62 from Henikoff et al., *Proc. Natl. Acad. Sci. USA*, 89:10915-10919 (1992);
Gap Penalty: 12
Gap Length Penalty: 4
Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparisons include the following:

Algorithm: Needleman et al., *J. Mol Biol.*, 48:443-453 (1970);
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

Using a known computer program such as BLAST or FASTA, two polypeptides are aligned for optimal matching of their respective amino acids (either along the full length of one or both sequences, or along a pre-determined portion of one or both sequences). The programs provide a "default" opening penalty and a "default" gap penalty, and a scoring matrix such as PAM 250. A standard scoring matrix can be used in conjunction with the computer program; see Dayhoff et al., in Atlas of Protein Sequence and Structure, volume 5, supplement 3 (1978). The percent identity can then be calculated as follows:

$$\frac{\text{Total number of identical matches} \times 100}{[\text{No. of residues in region of alignment not including non-identical residues at either or both ends and residues opposite a gap}]}$$

Analog polypeptides in accordance with the invention will typically have one or more amino acid substitutions, deletions and/or insertions. It is generally recognized that conservative amino acid changes are least likely to perturb the structure and/or function of a polypeptide and generally involve substitution of one amino acid with another that is similar in structure and/or function (e.g., amino acids with side chains similar in size, charge and/or shape). The nature of these substitutions are well known to one skilled in the art and exemplary amino acid substitutions are summarized in Tables 1 and 2.

TABLE 1

Amino Acid Substitutions

Basic:

Arg; Lys; His; Asn; Gln
Acidic:

Glu; Asp
Polar:

Glu; Asn
Hydrophilic:

Asp; Glu; Asn; Ser; Tyr
Hydrophobic:

Ala; Met; Ile; Leu; nor-Leu; Val
Aromatic:

Phe; Trp; Tyr
Small:

Gly; Ala; Ser; Thr; Met

TABLE 2

Amino Acid Substitutions

| Amino Acid | Preferred Substitutions | Most Preferred Substitution |
|---|---|---|
| Ala | Gly; Leu; Ile; Asn; Pro | Val |
| Arg | Ala; Asn; Gln; Ser | Lys |
| Asn | Arg; Gln; His; Lys; Ser; Tyr | Gln |
| Asp | Asn; Ser; Thr; Gln | Glu |
| Cys | Ala | Ser |
| Gln | Ala; Arg; Glu; Leu; Lys; Met; Ser; Tyr | Asn |
| Glu | Gln; Ser; Thr; Asn | Asp |
| Gly | | Pro |
| His | Asn; Gln; Lys; Tyr; Phe | Arg |
| Ile | Tyr; Val; Met; Ala; Phe; nor-Leu | Leu |
| Leu | nor-Leu; Ile; Val; Met; Ala; Phe | Ile |
| Lys | Asn; Asp; Ala; Glu; Gln; Ser; Tyr | Arg |
| Met | Ala; Gln; Tyr; Trp; Phe | Leu |
| Phe | Leu; Val; Ile; Ala; Met | Leu |
| Pro | Ile; Val | Gly |
| Ser | Ala; Asn; Asp; Gly; Lys | Thr |
| Thr | Ala; Gly; Ile; Val; Lys | Ser |
| Trp | Phe; Tyr; His | Tyr |
| Tyr | Trp; Thr; Ser | Phe |
| Val | Ala; Ile; Met; Phe; Tyr; nor-Leu | Leu |

Changing from A, F, H, I, L, M, P, V, W, or Y to C is more preferred if the new cysteine remains as a free thiol.

Desired amino acid substitutions (whether conservative or non-conservative) can be determined by those skilled in the art at the time such substitutions are desired. For example, amino acid substitutions can be used to identify important residues of the peptide sequence, or to increase or decrease the affinity of the peptide or vehicle-peptide molecules (see preceding formula) described herein.

In certain embodiments, conservative amino acid substitutions also encompass non-naturally occurring amino acid residues which are typically incorporated by chemical peptide synthesis rather than by synthesis in biological systems.

As noted in the foregoing section, naturally occurring residues may be divided into classes based on common side chain properties that may be useful for modifications of sequence. For example, non-conservative substitutions may involve the exchange of a member of one of these classes for a member from another class. Such substituted residues may be introduced into regions of the peptide that are homologous with non-human orthologs, or into the non-homologous regions of the molecule. In addition, one may also make modifications using P or G for the purpose of influencing chain orientation.

In making such modifications, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157: 105-131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

A skilled artisan will be able to determine suitable analogs of the peptides and modified peptides set forth herein using well known techniques. For identifying suitable areas of the molecule that may be changed without destroying activity, one skilled in the art may target areas not believed to be important for activity. It will be appreciated that changes in areas of a peptide that are not conserved relative to other such similar peptides would be less likely to adversely affect the biological activity and/or structure of the peptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the peptide structure.

Additionally, one skilled in the art can review structure-function studies identifying residues in similar peptides that are important for activity or structure. In view of such a comparison, one can predict the importance of amino acid residues in a peptide that correspond to amino acid residues that are important for activity or structure in similar peptides. One skilled in the art may opt for chemically similar amino acid substitutions for such predicted important amino acid residues of the peptides or modified peptides of the present invention.

One skilled in the art can also analyze the three-dimensional structure and amino acid sequence in relation to that structure in similar peptides or polypeptides. In view of that information, one skilled in the art may predict the alignment of amino acid residues of a peptide or a polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test analogs containing a single amino acid substitution at each desired amino acid residue. The analogs can then be screened using activity assays know to those skilled in the art. Such data could be used to gather information about suitable analogs. For example, if one discovered that a change to a particular amino acid residue resulted in destroyed, undesirably reduced, or unsuitable activity, analogs with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will gain dramatically in accuracy.

Additional methods of predicting secondary structure include "threading" (Jones, D., Curr. Opin. Struct. Biol., 7(3):377-87 (1997); Sippl et al., Structure, 4(1): 15-9 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-8 (1987)), and "evolutionary linkage" (See Home, supra, and Brenner, supra).

Peptide and modified peptide fragments (i.e., subsequences) included within the invention will be those that have less than the full length sequence, but which possess substantially the same biological activity in vitro and/or in vivo with respect to anti-NGF activity and are truncated at the amino terminus, the carboxy terminus, and/or internally.

Peptide and modified peptide analogs, fragments, and derivatives in accordance with the invention will be useful for the same purposes for which the peptides and modified peptides specifically disclosed herein are useful (i.e., antagonists of NGF activity in vitro and/or in vivo).

Peptides. The peptides used in conjunction with the present invention are, as mentioned, peptides that modulate (e.g., increase or decrease) the activity of NGF. Phage display, in particular, has been useful in generating the peptides which are listed below in Table 3 (SEQ ID NOS: 1-29). Also useful are the methionyl-mature (Met$^{-1}$) versions of each of these peptides, in which a methionine residue may be expressed at the N-terminus (SEQ ID NOS: 30-58). Especially preferred peptides of the present invention are the affinity matured peptides listed below in Table 5 (SEQ ID NOS: 202-280).

Vehicles. The term "vehicle" as used herein refers to a molecule that prevents degradation and/or increases half-life, reduces toxicity, reduces immunogenicity, or increases biological activity of a therapeutic protein. In the context of the invention, the preferred vehicle constitutes an Fc domain. One aspect of the invention requires the presence of at least one vehicle ($F^1$) attached to a peptide through the N-terminus, C-terminus, and/or a side chain of one of the amino acid residues. Multiple vehicles may be used, such as, for example, Fc domains (Fc) at each terminus.

The Fc domain may be fused to the N or C termini of the peptide or at both the N and C termini. A native Fc may be extensively modified to form an Fc analog in accordance with the invention, provided that binding to the intended substrate (i.e., NGF) is maintained; see, for example, WO 97/34631 and WO 96/32478. In such Fc variants, one may remove one or more sites of a native Fc that provide structural features or functional activity not required by the fusion molecules of the invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, and several of them are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (for example, alanyl or seryl).

2. A native Fc is modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionine residue, especially when the molecule is expressed recombinantly in a bacterial cell such as *E. coli*. The Fc domain of SEQ ID NO: 60 (FIG. 2) is one such Fc variant. Such an Fc variant is preferred for certain embodiments of the present invention, in particular, those embodiments having the formulas:

$$F_c\text{-}P \tag{V}$$

wherein the Fc domain is attached to the N-terminus of the peptide;

$$F_c\text{-}(X^2) \tag{VI}$$

wherein the Fc domain is attached to the N-terminus of the linker-peptide component ($X^2$) of a modified peptide; and most preferably

$$F_c\text{-}(L)_c\text{-}P \tag{VII}$$

wherein the Fc domain is attached at the N-terminus of the linker-peptide component ($X^2$) of a modified peptide and wherein ($X^2$) has the formula -(L)$_c$-P.

Embodiments of the present invention also include modified peptides of the formulas:

$$P\text{-}F_c \tag{VIII}$$

wherein a Fc domain is attached to the C-terminus of the peptide;

$$(X^1)\text{-}F_c \tag{IX}$$

wherein the Fc domain is attached to the C-terminus of the peptide-linker component ($X^1$); and

$$P\text{-}(L)_c\text{-}F_c \tag{X}$$

wherein the Fc domain is attached at the C-terminus of the linker-peptide component ($X^2$) and wherein ($X^2$) has the formula P-(L)$_c$. For modified peptides of the formula (VIII)-(X), the preferred vehicle is a Fc variant wherein the Fc domain shown in SEQ ID NO:60 lacks the methionine residue shown at position 1 of SEQ ID NO:60.

3. A portion of the N-terminus of a native Fc is removed to prevent N-terminal heterogeneity when expressed in a selected host cell. For this purpose, one may delete any of the first twenty amino acid residues at the N-terminus, particularly those at positions 1, 2, 3, 4 and 5. Such an Fc variant is preferred for certain embodiments of the present invention, in particular, when the vehicle (F$^1$) is attached to the N-terminus of the peptide or linker-peptide component of a modified peptide of the present invention.

4. One or more glycosylation sites are removed. Residues that are typically glycosylated (e.g., asparagine) may confer cytolytic response. Such residues may be deleted or substituted with residues that are not glycosylated (e.g., alanine).

5. Sites involved in interaction with complement, such as the C1q binding site, are removed. For example, one may delete or substitute the EKK sequence of human IgG1. Complement recruitment may not be advantageous for the molecules of the invention and so may be avoided with such an Fc variant.

6. Sites are removed that affect binding to Fc receptors other than a salvage receptor. A native Fc may have sites for interaction with certain white blood cells that are not required for the fusion molecules of the present invention and so may be removed.

7. The ADCC site is removed. ADCC sites are known in the art; see, for example, Molec. Immunol., Volume 29 Number 5, pages 633-639 (1992) with regard to ADCC sites in IgG1. These sites, as well, are not required for the modified peptides (fusion products) of the present invention and so may be removed.

8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

As between the peptides or modified peptides of the present invention and substantial homologs thereof, it is preferable that no more than six residues in the P region, other than at termini, are different. More preferably, substantial homologs contemplated by the present invention include molecules with up to about six amino acid substitutions, insertions, or deletions at any particular locus, other than at a termini, of the P region of a peptide or modified peptide of the present invention. Most preferably, the divergence in sequence between a peptide or modified peptide and a substantial homolog thereof, particularly in the specified P region, is in the form of "conservative modifications".

Linkers. Any "linker" group is optional. When present, its chemical structure is not critical, since it serves primarily as a spacer. The linker is preferably made up of amino acids linked together by peptide bonds. Thus, in preferred embodiments, the linker is made up of from 1 to 20 amino acids linked by peptide bonds, wherein the amino acids are selected from the twenty naturally occurring amino acids. Some of these amino acids may be glycosylated, as will be understood by those skilled in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines, particularly (Gly)$_4$ (SEQ ID NO: 284), (Gly)$_5$ (SEQ ID NO: 285), (Gly)$_7$ (SEQ ID NO: 286), as well as poly(Gly-Ala) and polyalanines. Other specific examples of linkers are:

| | |
|---|---|
| (Gly)$_3$Lys(Gly)$_4$; | (SEQ ID NO: 123) |
| (Gly)$_3$AsnGlySer(Gly)$_2$; | (SEQ ID NO: 124) |
| (Gly)$_3$Cys(Gly)$_4$; and | (SEQ ID NO: 125) |
| GlyProAsnGlyGly. | (SEQ ID NO: 126) |

To explain the above nomenclature, for example, (Gly)$_3$Lys(Gly)$_4$ means Gly-Gly-Gly-Lys-Gly-Gly-Gly-Gly. Combinations of Gly and Ala are also preferred. The linkers shown here are merely exemplary; linkers within the scope of the invention may be much longer and may include other residues.

Non-peptide linkers are also possible. For example, alkyl linkers such as —NH—(CH$_2$)$_s$—C(O)—, wherein s=2-20 could be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc. An exemplary non-peptide linker is a PEG linker,

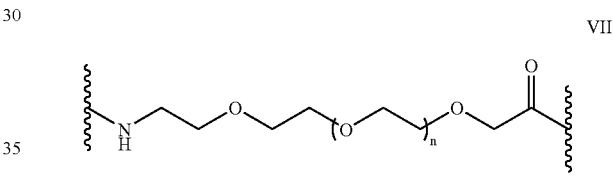

VII wherein n is such that the linker has a molecular weight of 100 to 5000 kilodaltons (kD), preferably 100 to 500 kD. The peptide linkers may be altered to form derivatives in the same manner as described above.

Derivatives. Also contemplated are derivatives of the peptides or the modified peptides of the present invention. Such derivatives may improve the solubility, absorption, biological half-life, and the like, of the peptides or modified peptides. The moieties may alternatively eliminate or attenuate any undesirable side-effect of the peptides or modified peptides, and the like. Exemplary derivatives include peptides or modified peptides in which:

1. The peptide or modified peptide or some portion thereof is cyclic. For example, the peptide or peptide portion of a modified peptide may be modified to contain two or more Cys residues (e.g., in the linker), which could cyclize by disulfide bond formation. For citations to references on the preparation of cyclized derivatives, see WO 00/24782.

2. The peptide or modified peptide is cross-linked or is rendered capable of cross-linking between molecules. For example, the peptide or peptide portion of a modified peptide may be modified to contain one Cys residue and thereby be able to form an intermolecular disulfide bond with a like molecule. The modified peptide may also be cross-linked through its C-terminus, as in the molecule shown below.

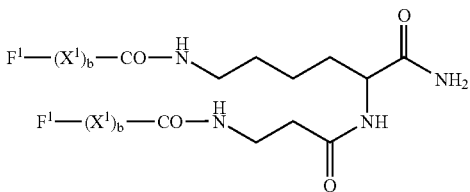

3. One or more peptidyl [—C(O)NR—] linkages (bonds) is replaced by a non-peptidyl linkage. Exemplary non-peptidyl linkages are —CH$_2$-carbamate [—CH$_2$—OC(O)NR—], phosphonate, —CH$_2$-sulfonamide [—CH$_2$—S(O)$_2$NR—], urea [—NHC(O)NH—], —CH$_2$-secondary amine, and alkylated peptide [—C(O)NR$^6$— wherein R$^6$ is lower alkyl].

4. The N-terminus is derivatized. Typically, the N-terminus may be acylated or modified to a substituted amine. Exemplary N-terminal derivative groups include —NRR$^1$ (other than —NH$_2$), —NRC(O)R$^1$, —NRC(O)OR$^1$, —NRS(O)$_2$R$^1$, —NHC(O)NHR$^1$, succinimide, or benzyloxycarbonyl-NH— (CBZ-NH—), wherein R and R$^1$ are each independently hydrogen or lower alkyl and wherein the phenyl ring may be substituted with 1 to 3 substituents selected from the group consisting of C$_1$-C$_4$ alkyl, C$_1$-C$_4$ alkoxy, chloro, and bromo.

5. The free C-terminus is derivatized. Typically, the C-terminus is esterified or amidated. For example, one may use methods described in the art to add (NH—CH$_2$—CH$_2$—NH$_2$)$_2$ to modified peptides of the invention having any of SEQ ID NOS: 1 to 58 at the C-terminus. Likewise, one may use methods described in the art to add —NH$_2$ to modified peptides of the invention having any of SEQ ID NOS: 1 to 58 at the C-terminus. Exemplary C-terminal derivative groups include, for example, —C(O)R$^2$ wherein R$^2$ is lower alkoxy or —NR$^3$R$^4$ wherein R$^3$ and R$^4$ are independently hydrogen or C$_1$-C$_8$ alkyl (preferably C$_1$-C$_4$ alkyl).

6. A disulfide bond is replaced with another, preferably more stable, cross-linking moiety (e.g., an alkylene). See, for example, Bhatnagar et al., J. Med. Chem., Volume 39, pages 3814-3819 (1996); Alberts et al., Thirteenth Am. Pep. Symp., pages 357-359 (1993).

Derivatization with bifunctional agents is useful for cross-linking the peptides or modified peptides or their functional derivatives to a water-insoluble support matrix or to other macromolecular vehicles. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]-propioimidate yield photo-activatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Carbohydrate (oligosaccharide) groups may conveniently be attached to sites that are known to be glycosylation sites in proteins. Generally, O-linked oligosaccharides are attached to serine (Ser) or threonine (Thr) residues, while N-linked oligosaccharides are attached to asparagine (Asn) residues when they are part of the sequence Asn-X-Ser/Thr, where X can be any amino acid except proline. X is preferably one of the nineteen naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated modified peptide. Such site(s) may be incorporated in the linker of the modified peptides of the invention and are preferably glycosylated by a cell during recombinant production of the polypeptide modified peptides (e.g., in mammalian cells such as CHO, BHK, COS). However, such sites may further be glycosylated by synthetic or semi-synthetic procedures known in the art.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains. Creighton, Proteins: Structure and Molecule Properties, W. H. Freeman & Co., San Francisco, pages 79-86 (1983).

Also contemplated are the chemical modifications of the peptides by the attachment of at least one moiety wherein said moiety permits an increase in overall stability of the modified peptide and increase in circulation time in the body. Moieties useful as covalently attached vehicles in the invention may also be used for this purpose. Examples of such moieties include: polyethylene glycol (PEG), copolymers of ethylene glycol and propylene glycol, carboxymethyl cellulose, dextran, polyvinyl alcohol, polyvinyl pyrrolidone and polyproline. See, for example, Abuchowski and Davis, Soluble Polymer-Enzyme Adducts, Enzymes as Drugs, Hocenberg and Roberts, eds., Wiley-Interscience, New York, N.Y., pages 367-383 (1981); Newmark et al., J. Appl. Biochem. Volume 4, pages 185-189 (1982). Other polymers that could be used are poly-1,3-dioxolane and poly-1,3,6-trioxocane. Preferred are PEG moieties.

Peptides and modified peptides of the present invention may be changed at the DNA level, as well. The DNA sequence of any portion of the modified peptide may be changed to codons more compatible with the chosen host cell. For *E. coli*, which is the preferred host cell, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes.

Methods of Making

The modified peptides of the invention, for the most part, may be made in transformed host cells using recombinant DNA techniques. To do so, a recombinant DNA molecule coding for the peptide is prepared. Methods of preparing such DNA molecules are well known in the art. Reference works on the general principles of recombinant DNA Technology include Watson et al., *Molecular Biology of the Gene,* Volumes I and II, The Benjamin/Cummings Publishing Company, Inc., Menlo Park, Calif. (1987); Darnell et al., *Molecular Cell Biology,* Scientific American Books, Inc., New York, N.Y. (1986); Lewin, *Genes* II, John Wiley & Sons, New York, N.Y. (1985); Old, et al., *Principles of Gene Manipulation: An Introduction to Genetic Engineering,* 2k edition, University of California Press, Berkeley, Calif. (1981); Sambrook et al., *Molecular Cloning, A Laboratory*

*Manual,* Cold Spring Harbor Laboratory Press, Cold Spring Harbor, N.Y. (1989); and Ausubel et al, *Current Protocols in Molecular Biology,* Wiley Interscience, N.Y., (1987, 1992). These references are herein entirely incorporated by reference as are the references cited therein.

For instance, sequences coding for the peptides can be excised from DNA using suitable restriction enzymes. Alternatively, the DNA molecule can be synthesized using chemical synthesis techniques, such as the phosphoramidate method. Also, a combination of these techniques can be used.

The invention also includes a vector capable of expressing the peptides or modified peptides in an appropriate host. The vector comprises the DNA molecule that codes for the peptides or modified peptides operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of the invention. The selection of a particular host is dependent upon a number of factors recognized by the art. These include, for example, compatibility with the chosen expression vector, toxicity of the peptides encoded by the DNA molecule, rate of transformation, ease of recovery of the peptides or modified peptides, expression characteristics, bio-safety, and costs. A balance of these factors must be struck, with the understanding that not all hosts may be equally effective for the expression of a particular DNA sequence.

Within these general guidelines, useful microbial hosts include bacteria from the genera *Bacillus, Escherichia* (such as *E. coli*), *Pseudomonas, Streptomyces, Salmonella, Erwinia,* and yeasts from the genera *Hansenula, Kluyveromyces, Pichia, Rhinosporidium, Saccharomyces,* and *Schizosaccharomyces,* and other fungi. The more preferred hosts are microorganisms of the species *Pichia pastoris, Bacillus subtilis, Bacillus brevis, Saccharomyces cerevisiae,* the various strains of *Escherichia coli* (e.g., HB101, (ATCC NO. 33694) DH5α, DH10, and MC1061 (ATCC NO. 53338)), and *Yarrowia lipolytica.*

A number of suitable mammalian host cells are also known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61) CHO DHFR-cells (Urlaub et al., *Proc. Natl. Acad. Sci. USA,* 97:4216-4220 (1980)), human embryonic kidney (HEK) 293 or 293T cells (ATCC No. CRL1573), or 3T3 cells (ATCC No. CCL92). The selection of suitable mammalian host cells and methods for transformation, culture, amplification, screening and product production and purification are known in the art. Other suitable mammalian cell lines, are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include, but are not limited to, mouse neuroblastoma N2A cells, HeLa, mouse L-929 cells, 3T3 lines derived from Swiss, Balb-c or NIH mice, BHK or HaK hamster cell lines, which are available from the ATCC. Each of these cell lines is known by and available to those skilled in the art of protein expression.

Many strains of yeast cells known to those skilled in the art are also available as host cells for the expression of the polypeptides of the present invention. Preferred yeast cells include, for example, *saccharomyces cerivisae* and *pichia pastoris.*

Additionally, where desired, insect cell systems may be utilized in the methods of the present invention. Such systems are described for example in Kitts et al., *Biotechniques,* 14:810-817 (1993); Lucklow, *Curr. Opin. Biotechnol.,* 4:564-572 (1993); and Lucklow et al. (*J. Virol.,* 67:4566-4579 (1993). Preferred insect cells are Sf-9 and HI5 (Invitrogen, Carlsbad, Calif.). One may also use transgenic animals to express the peptides and modified peptides of the present invention. For example, one may use a transgenic milk-producing animal (a cow or goat, for example) and obtain the peptide or modified peptide in the animal milk. One may also use plants to produce the peptides and modified peptides of the present invention, however, in general, the glycosylation occurring in plants is different from that produced in mammalian cells, and may result in a glycosylated product which is not suitable for human therapeutic use.

The transformed host is cultured and a single clonal isolate is purified. Host cells may be cultured under conventional fermentation conditions so that the desired modified peptides are expressed. Such fermentation conditions are well known in the art. Any promoter which is functional in the host cell may be used to control gene expression.

Preferably the modified peptides, or at least the peptide portion thereof, of the invention are secreted. If the modified peptide or peptide portion thereof is secreted, the peptides can be purified from culture by methods well known in the art.

If the modified peptide or peptide portion thereof is expressed in bacterial hosts as insoluble inclusion bodies the modified peptides or peptide portion thereof can be harvested from host cells in accordance with methods known in the art. For example, the solubilization of washed and frozen inclusion bodies can be accomplished by the addition of a buffer containing a chaotropic agent and a reducing agent to thawed inclusion bodies. Preferably, the solubilization mixture is diluted into the refold buffer to form the correct protein conformation and disulfide bonds. Redox reagents may be added to the refold buffer just prior to the addition of the solubilization mixture. The refold solution may be passed through a filter system to remove particulate matter and then be concentrated by low temperature (approximately 5° C.) ultrafiltration (UF). Low temperature dialfiltration (DF) may be performed also to remove low molecular weight solutes. Precipitation and clarification at an acidic pH is generally carried out to remove the majority of host cell impurities, product aggregates, and misfolded impurities. Residual host cell impurities and product aggregates may be removed by cation exchange chromatography e.g., on SP Sepharose FF media, Q Sepharose HP column, and/or Ceramic Hydroxyapatite resin (Bio-Rad, Hercules, Calif.).

The modified peptides, or at least the peptide portion thereof, may also be made by synthetic methods. For example, solid phase synthesis techniques may be used.

Suitable techniques are well known in the art, and include those described in Merrifield, Chem. Polypeptides, pages 335-361 (Katsoyannis and Panayotis editors) (1973); Merrifield, J. Am. Chem. Soc., Volume 85, page 2149 (1963); Davis et al., Biochem. Intl., Volume 10, pages 394-414 (1985); Stewart and Young, Solid Phase Peptide Synthesis (1969); U.S. Pat. No. 3,941,763; Finn et al., The Proteins (3d edition), Volume 2, pages 105-253 (1976); and Erickson et al., The Proteins (Third Edition), Volume 2, pages 257-527 (1976). Solid phase synthesis is the preferred technique for making individual peptides because of its cost-effectiveness.

Modified peptides that contain non-peptide groups may be synthesized by well-known organic chemistry techniques.

Pharmaceutical Compositions

In General. The present invention also provides methods of using pharmaceutical compositions of the inventive peptides and/or modified peptides, e.g., in the prevention or treatment of pain (including, but not limited to, inflammatory pain and associated hyperalgesia and allodynia, neuropathic pain and associated hyperalgesia and allodynia, diabetic neuropathy pain, causalgia, sympathetically maintained pain, deafferentation syndromes, acute pain, tension headache, migraine, dental pain, pain from trauma, surgical pain, pain resulting from amputation or abscess, causalgia, demyelinating diseases, and trigeminal neuralgia). The peptides and modified peptides of the invention have therapeutic value for the prevention or treatment of other diseases linked to NGF as a causative agent, including, but not limited to, asthma, urge incontinence (i.e., hyperactive bladder), psoriasis, cancer (especially, pancreatic cancer and melanoma), chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, colitis, gastric ulceration, duodenal ulcers, vasomotor or allergic rhinitis, or bronchial disorders.

The invention also provides for the use of the peptides and/or modified peptides of the present invention for the prevention or treatment of the same diseases listed above.

Accordingly, the present invention also relates to the use of one or more of the peptide and/or modified peptides of the present invention in the manufacture of a medicament for the treatment of a disorder such as any one of those mentioned above.

Such pharmaceutical compositions or medicaments may be for administration by injection, or for oral, pulmonary, nasal, transdermal or other forms of administration. In general, the invention encompasses pharmaceutical compositions comprising effective amounts of a peptide or modified peptide of the invention (in amounts effective to prevent, ameliorate, or abolish pain or any of the other medical conditions provided herein) together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimerosol, benzyl alcohol) and bulking substances (e.g., lactose, mannitol); incorporation of the material into particulate preparations of polymeric modified peptides such as polylactic acid, polyglycolic acid, etc. or into liposomes. Hyaluronic acid may also be used, and this may have the effect of promoting sustained duration in the circulation. Such compositions may influence the physical state, stability, rate of in vivo release, and rate of in vivo clearance of the present proteins and derivatives. See, for example, Remington's Pharmaceutical Sciences, 18th Edition., Mack Publishing Co., Easton, Pa., pages 1435-1712 (1990), which is herein incorporated by reference. The compositions may be prepared in liquid form, or as a dried powder (such as lyophilized form). Implantable sustained release formulations are also contemplated, as are transdermal formulations.

Oral dosage forms. Contemplated for use herein are oral solid dosage forms, which are described generally in Chapter 89 of Remington's Pharmaceutical Sciences, above, which is herein incorporated by reference. Solid dosage forms include tablets, capsules, pills, troches or lozenges, cachets or pellets. Also, liposomal or proteinoid encapsulation may be used to formulate the present compositions (such as, for example, the proteinoid microspheres reported in U.S. Pat. No. 4,925,673). Liposomal encapsulation may be used, and the liposomes may be derivatized with various polymers (see, for example, U.S. Pat. No. 5,013,556). A description of possible solid dosage forms is given in Chapter 10 of Marshall, K., Modern Pharmaceutics, edited by G. S. Banker and C. T. Rhodes (1979), herein incorporated by reference. In general, the formulation will include a modified peptide of the invention , as well as inert ingredients which allow for protection against the stomach environment and release of the modified peptide in the intestine.

Also specifically contemplated are oral dosage forms of the inventive peptides or modified peptides themselves. In this regard, if necessary, the peptides or modified peptides may be chemically modified so that oral delivery is efficacious. It is also possible to use a salt of a modified aliphatic amino acid, such as sodium N-(8-[2-hydroxybenzoyl] amino) caprylate (SNAC), as a carrier to enhance absorption of the modified peptides of the invention. See U.S. Pat. No. 5,792,451, entitled "Oral Drug Delivery Composition and Methods".

The peptides or modified peptides of the invention can be included in the formulation as fine multiparticulates in the form of granules or pellets of a particle size about one millimeter. The formulation of the material for capsule administration could also be as a powder, as lightly compressed plugs, or even as tablets. The therapeutic could be prepared by compression.

Colorants and flavoring agents may all be included. For example, the peptide or modified peptide or derivative thereof may be formulated (such as by liposome or microsphere encapsulation) and then further contained within an edible product, such as a refrigerated beverage containing colorants and flavoring agents.

One may dilute or increase the volume of the peptide or modified peptide of the invention with an inert material. These diluents could include carbohydrates, especially, mannitol, α-lactose, anhydrous lactose, cellulose, sucrose, modified dextrans and starch. Certain inorganic salts may also be used as fillers, including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include, but are not limited to, starch, including the commercially available disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may also be used. Another form of the disintegrants are the insoluble cationic exchange resins. Powdered gums may be used as disintegrants and as binders, and these can include powdered gums such as agar, Karaya or tragacanth. Alginic acid and its sodium salt are also useful as disintegrants.

Binders may be used to hold the components of the pharmaceutical composition together to form a hard tablet, and they include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation to prevent sticking during the formulating process. Lubricants may be used as a layer between the therapeutic and the die wall, and these can include, but are not limited to: stearic acid, including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the modified peptide during formulation and to aid rearrangement during compression might be added. Such glidants may include starch, talc, pyrogenic silica and hydrated silicoaluminate.

To aid dissolution of the peptide or modified peptide of the invention into the aqueous environment, a surfactant might be added as a wetting agent. Such surfactants may include anionic detergents such as sodium lauryl sulfate, dioctyl sodium sulfosuccinate and dioctyl sodium sulfonate. Cationic detergents may be used and can include benzalkonium chloride or benzethonium chloride. The list of potential nonionic detergents that may be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants may be present in the formulation either alone or as a mixture in different ratios.

Additives may also be included in the formulation to enhance uptake of the peptide or modified peptide. Additives potentially having this property include various fatty acids, such as, for instance, oleic acid, linoleic acid and linolenic acid.

Controlled release formulation may be desirable. The peptide or modified peptide of the invention may be incorporated into an inert matrix which permits release by either diffusion or leaching mechanisms, for example, gums. Slowly degenerating matrices may also be incorporated into the formulation, for example, alginates or polysaccharides. Another form of a controlled release of the peptide or modified peptide of the invention is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film-coated tablet, and the materials used in this instance are divided into two groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of enteric materials that are commonly esters of phthalic acid.

A mixture of materials may be used to provide the optimum film coating. Film coating may be carried out in a pan coater, in a fluidized bed, or by compression coating.

Pulmonary delivery forms. Also contemplated herein is pulmonary delivery of a pharmaceutical composition in accordance with the invention. The peptide or modified peptide (or derivatives thereof) is delivered to the lungs of a mammal while inhaling and traverses across the lung epithelial lining to the blood stream. Reports relating to the pulmonary delivery of macromolecules that may be helpful in this regard include Adjei et al., Pharma. Res., Volume 7, pages 565-569 (1990); Adjei et al., Internatl. J. Pharmaceutics, Volume 63, pages 135-144 (1990) (leuprolide acetate); Braquet et al., J. Cardiovasc. Pharmacol., Volume 13 (suppl. 5), s. 143-146 (1989) (endothelin-1); Hubbard et al., Annals Int. Med., Volume 3, pages 206-12 (1989) ($\alpha$1-antitrypsin); Smith et al., J. Clin. Invest., Volume 84, pages 1145-1146 (1989) ($\alpha$1-proteinase); Oswein et al., "Aerosolization of Proteins", Proc. Symp. Resp. Drug Delivery II, Keystone, Colorado (1990) (recombinant human growth hormone); Debs et al., J. Immunol., Volume 140, pages 3482-3488 (1988) (interferon-$\gamma$ and tumor necrosis factor $\alpha$); and U.S. Pat. No. 5,284,656 (granulocyte colony stimulating factor).

Contemplated for use in the practice of the invention are a wide range of mechanical devices designed for the pulmonary delivery of therapeutic products, including but not limited to nebulizers, metered dose inhalers, and powder inhalers, all of which are familiar to those skilled in the art. Some specific examples of commercially available devices suitable for the practice of the invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the described peptides and modified peptides. Typically, each formulation is specific to the type of device employed and may involve the use of an appropriate propellant material, in addition to diluents, adjuvants and/or carriers useful in therapy.

The peptides or modified peptides of the invention will most advantageously be prepared in particulate form, with an average particle size of less than 10 micrometers ($\mu$m), or microns, and most preferably in the range from 0.5 to 5 $\mu$m, for most effective delivery to the distal lung.

Pharmaceutically acceptable carriers for these pulmonary compositions include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the protein or analog). Dextrans, such as cyclodextran, bile salts, cellulose and cellulose derivatives may also be used. Amino acids may be used, such as in a buffer formulation.

In addition, the use of liposomes, microcapsules or microspheres, inclusion complexes, or other types of carriers is contemplated.

Formulations suitable for use with a nebulizer, either jet or ultrasonic type, will typically comprise the described modified peptide dissolved in water at a concentration of about 0.1 to 25 milligrams (mg) of biologically active protein per milliliter (ml) of solution. The formulation may also include a buffer and a simple sugar (e.g., for peptide stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the described modified peptide suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the described modified peptide and may also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery forms. Nasal delivery of the peptides and modified peptides is also contemplated. Nasal delivery allows the passage of the modified peptides of the invention to the blood stream directly after administering the therapeutic product to the nose, without the necessity for deposition of the product in the lung. Formulations for nasal delivery include those with dextran or cyclodextran. Delivery via transport across other mucous membranes is also contemplated.

Dosages. The dosage regimen involved in a method for treating the involved disease or disorder will be determined by the attending physician, considering various factors which modify the action of therapeutic agents, such as the age, condition, body weight, sex and diet of the patient, the severity of the condition being treated, time of administration, and other clinical factors. Generally, the daily regimen should be in the range of 1.0-10000 micrograms (μg) of the modified peptide per kilogram (kg) of body weight, preferably 1.0-1000 μg per kilogram of body weight, and most preferably 1.0-150 μg per kilogram of body weight.

EXAMPLES

The peptides and modified peptides of the invention may be prepared as described below. These examples comprise preferred embodiments of the invention and are intended to be illustrative only and not limiting.

Example 1

Identification of NGF-Inhibitory Peptides by Peptide Phage Display

1. NGF-coated Magnetic Bead Preparation

A. Biotinylation of NGF protein. Human recombinant NGF was biotinylated using the EZ-link Sulfo-NHS-LC-Biotinylation Kit (Pierce, Rockford, Ill.) according to the manufacturer's suggestions. The biotinylated NGF protein was dialyzed in phosphate buffered saline (PBS) to remove any free-floating biotin from the solution. The biotinylated NGF protein solution was passed through the Immunopure Immobilized Monomeric Avidin column (Pierce, Rockford, Ill.) to further remove any unbound or loosely bound biotins. The biotinylated NGF protein-containing solution was concentrated using Centricon units (Amicon, Bedford, Mass.), and the final protein concentration was determined using Bio-Rad Protein Assay reagent (Bio-Rad Labs, Hercules, Calif.). The purified and concentrated biotinylated NGF was shown to be fully active in the DRG neuron-based NGF neutralization bioassay (see further below in Example 3) and also in an SCG neuron-based neutralization assay (not described here).

B. NGF immobilization on magnetic beads. The biotinylated NGF protein was immobilized on Streptavidin Dynabeads (Dynal, Lake Success, N.Y.) at a concentration of 2 milligrams (mg) of biotinylated NGF protein per 100 milliliters (ml) of the bead stock from the manufacturer. By drawing the beads to one side of a tube using a magnet and pipetting away the liquid, the beads were washed twice with phosphate buffered saline (PBS) and resuspended in PBS. Biotinylated NGF protein was added to the washed beads at the above concentration and incubated, with rotation, for one hour at room temperature. NGF-coated beads were then blocked by adding BSA to 1% final concentration and incubating overnight at 4° C., with rotation. The resulting NGF-coated beads were then washed five times with PBST (i.e., PBS with 0.05% Tween-20) before being subjected to the selection procedures.

C. Negative selection bead preparation. Additional beads were also prepared for negative selections. For each panning condition, 250 microliters (μl) of the bead stock from the manufacturer was subjected to the above procedure (Section 1.A., above) except that the incubation step with biotinylated NGF was omitted. In the last washing step, the beads were divided into five 50-ml aliquots.

2. Selection of NGF Binding Phage

A. Overall strategy. Three filamentous phage libraries, TN8-IX ($5 \times 10^9$ independent transformants), TN12-I ($1.4 \times 10^9$ independent transformants), and Linear ($2.3 \times 10^9$ independent transformants) (Dyax Corp., Cambridge, Mass.), were used to select for NGF binding phage. Each library was subjected to antibody elution (Section 2.D.), receptor elution (Section 2.E.), and bead elution (Section 2.F.). Thus, nine different panning conditions were carried out (TN8-IX using the antibody elution method, TN8-IX using the receptor elution method, TN8-IX using the bead elution method, TN12-I using the antibody elution method, TN12-I using the receptor elution method, and TN12-I using the bead elution method, Linear using the antibody elution method, Linear using the receptor elution method, and Linear using the bead elution method). Three rounds of selection were performed for each condition.

B. Negative selection. For each panning condition, about 100 random library equivalent for TN8-IX and TN12-I libraries ($5 \times 10^{11}$ pfu for TN8-IX, and $1.4 \times 10^{11}$ pfu for TN12-I) and about 10 random library equivalent for Linear library (2.3×10¹⁰ pfu) were aliquoted from the library stock and diluted to 300 µl of PBST. After the last washing liquid was drawn out from the first 50-µl aliquot of the beads prepared for negative selections (Section 1.B.), the 300 µl-diluted library stock was added to the beads. The resulting mixture was incubated for ten minutes at room temperature with rotation. The phage supernatant was drawn out using the magnet and added to the second 50 µl aliquot for another negative selection step. In this manner, five negative selection steps were performed.

C. Selection using the NGF protein coated beads. The phage supernatant after the last negative selection step (Section 1.B., above) was added to the NGF-coated beads after the last washing step (Section 1.A., above). This mixture was incubated with rotation for one to two hours at room temperature, allowing specific phage to bind to the target protein. After the supernatant was discarded, the beads were washed seven times with PBST.

D. Antibody elution of bound phage. After the last washing step (Section 2.C., above), the bound phages were eluted from the magnetic beads by adding 100 µl of 10 µM Monoclonal Anti-Human Nerve Growth Factor-β Clone 25623.1 (Catalog No. N-3279, Sigma, St. Louis, Mo.). After one hour of incubation with rotation at room temperature, the liquid containing the eluted phage was drawn out and transferred to another tube. Nine hundred microliters of Min A Salts solution (60 mM $K_2HPO_4$, 33 mM $KH_2PO_4$, 7.6 mM $(NH_4)SO_4$, and 1.7 mM sodium citrate) were added to bring the final volume to 1 ml.

E. Receptor (trkA) elution of bound phage. After the last washing step (Section 2.C., above), the bound phages were eluted from the magnetic beads by adding 100 µl of 100 µM soluble NGF receptor, trkA (Ig-like extracellular subdomain; amino acids 280-384). After one hour of incubation with rotation at room temperature, the liquid containing the eluted phage was drawn out and transferred to another tube. Nine hundred microliters of Min A Salts solution (60 mM $K_2HPO_4$, 33 MM $KH_2PO_4$, 7.6 mM $(NH_4)SO_4$, and 1.7 mM sodium citrate) were added to make the final volume to 1 ml.

F. Bead elution. After the final washing liquid was drawn out (Section 2.C.), 1 ml of Min A salts solution was added to the beads. This bead mixture was added directly to a concentrated bacteria sample for infection (Sections 3.A. and 3.B., following).

3. Amplification

A. Preparation of plating cells. Fresh *E. coli* (XL-1 Blue MRF') culture was grown to $OD_{600}=0.5$ in LB media containing 12.5 µg/ml of tetracycline. For each panning condition, 20 ml of this culture were chilled on ice and centrifuged. The bacterial pellet was resuspended in 1 ml of the Min A Salts solution.

B. Transduction. Each mixture from different elution methods (Sections 2.D. and 2.E., above) was added to a concentrated bacteria sample (Section 3.A.) and incubated at 37° C. for fifteen minutes. Two milliliters of NZCYM media (2XNZCYM, 50 µg/ml Ampicillin) were added to each mixture and incubated at 37° C. for fifteen minutes. The resulting 4-ml solution was plated on a large NZCYM agar plate containing 50 µg/ml of Ampicillin and incubated overnight at 37° C.

C. Phage Harvesting. Each of the bacteria/phage mixtures that had been grown overnight on a large NZCYM agar plate (Section 3.B.) was scraped off in 35 ml of LB media, and the agar plate was further rinsed with an additional 35 ml of LB media. The resulting bacteria/phage mixture in LB media was centrifuged to remove the bacteria. Fifty milliliters of the phage supernatant was transferred to a fresh tube, and 12.5 ml of PEG solution (20% PEG 8000, 3.5 M ammonium acetate) were added and incubated on ice for two hours to precipitate phages. Precipitated phage were centrifuged down and resuspended in 6 ml of the phage resuspension buffer (250 mM NaCl, 100 mM Tris pH8, 1 mM EDTA). This phage solution was further purified by centrifuging away the remaining bacteria and precipitating the phage for the second time by adding 1.5 ml of the PEG solution. After a centrifugation step, the phage pellet was resuspended in 400 ml of PBS. This solution was subjected to a final centrifugation to rid it of any remaining bacterial debris. The resulting phage preparation was titered by a standard plaque formation assay (Molecular Cloning, Maniatis, et al., Third Edition).

4. Additional Rounds of Selection and Amplification.

In a second round, the amplified phage ($10^{10}$ pfu) from the first round (Section 3.C.) was used as the input phage to perform the selection and amplification steps (Sections 2 and 3). The amplified phage ($10^{10}$ pfu) from the second round, in turn, was used as the input phage to perform the third round of selection and amplification (Sections 2 and 3). After the elution steps (Sections 2.D., 2.E., and 2.F.) of the third round, a small fraction of the eluted phage was plated out as in the plaque formation assay (Section 3.C.). Individual plaques were picked and placed into 96-well microtiter plates containing 100 µl of TE buffer (10 mM Tris, 1 mM EDTA, ph 8.0) in each well. Sambrook et al., Molecular Cloning, A Laboratory Manual, Cold Spring Harbor Laboratory Press, Cold Spring Harbor, N.Y. (1989). These master plates were incubated at 4° C. overnight to allow phages to elute into the TE buffer.

5. Clonal Analysis (Phage ELISA and Sequencing)

The phage clones were analyzed by phage ELISA and by conventional sequencing methods. The sequences were ranked based on the combined results from these two assays.

A. Phage ELISA. An XL-1 Blue MRF' culture was grown until $OD_{600}$ reached 0.5. Thirty microliters of this culture were aliquoted into each well of a 96-well Maxisorp microtiter plate. Ten microliters of eluted phage (from Section 4) were added to each well and allowed to infect bacteria for fifteen minutes at room temperature. One hundred and thirty microliters of LB media containing 12.5 µg/ml of tetracycline and 50 µg/ml of ampicillin were added to each well. The microtiter plate was then incubated with shaking overnight at 37° C. Recombinant NGF protein (1 mg/ml in PBS) was allowed to coat the 96-well plates (NUNC) overnight at 4° C. As a control, pure streptavidin was coated on a separate Maxisorp plate at 2 µg/ml in PBS. On the following day, liquid in the protein-coated Maxisorp plates was discarded, and each well was blocked with 300 ml of 5% milk solution at 4° C. overnight (alternatively, one hour at room temperature). The milk solution was discarded and the wells were washed three times with the PBST solution. After the last washing step, 50 µl of PBST-4% milk were added to each well of the protein-coated Maxisorp plates. Each of the 50-µl overnight cultures in the 96-well microtiter plate was transferred to the corresponding wells of the NGF-coated plates as well as to the control streptavidin-coated plates. The 100-µl mixtures in the two kinds of plates were incubated for one hour at room temperature. The liquid was discarded from the Maxisorp plates and the wells were washed five times with PBST. The HRP-conjugated anti-M13 antibody (Pharmacia) was diluted to 1:7500, and 100 µl of the diluted solution were added to each well of the Maxisorp plates for one hour incubation at room temperature. The liquid was again discarded and the wells were washed seven times with PBST. One hundred microliters of TMB substrate (Sigma) were added to each well for the color reaction to develop, and the reaction was stopped with 50 μl of 5N $H_2SO_4$ solution. The $OD_{450}$ was read on a plate reader (Molecular Devices).

B. Sequencing of the phage clones. For each phage clone, the sequencing template was prepared by a PCR method. The following oligonucleotide pair was used to amplify an approximately 500-base pair fragment: first primer, 5'-CGGCGCAACTATCGGTATCAAGCTG-3' (SEQ ID NO: 127), and second primer, 5'-CATGTACCGTAACACTGAGTTTCGTC-3' (SEQ ID NO: 128). The following mixture was prepared for each clone.

| Reagents | Volume (μL) per tube |
|---|---|
| $dH_2O$ | 26.25 |
| 50% glycerol | 10 |
| 10× PCR Buffer (w/o $MgCl_2$) | 5 |
| 25 mM $MgCl_2$ | 4 |
| 10 mM dNTP mix | 1 |
| 100 μM primer 1 | 0.25 |
| 100 μM primer 2 | 0.25 |
| Taq polymerase | 0.25 |
| Phage in TE (section 4) | 3 |
| Final reaction volume | 50 |

A thermocycler (GeneAmp PCR System 9700, Applied Biosystems, Inc., Foster City, Calif.) was used to run the following program: 94° C. for 5 minutes; [94° C. for 30 seconds, 55° C. for 30 seconds, 72° C. for 45 seconds]×30 cycles; 72° C. for 7 minutes; cool to 4° C. The PCR product from each reaction was purified using a QIAquick Multiwell PCR Purification kit (Qiagen), following the manufacturer's protocol. The purified product was checked by running 10 μl of each PCR reaction mixed with 1 μl of 10× agarose gel loading dye on a 1% agarose gel. The remaining product was then sequenced using an ABI 377 Sequencer (Applied Biosystems, Foster City, Calif.) in accordance with the manufacturer's recommended protocol.

6. Peptide Sequence Ranking and Consensus Sequences

A. Sequence ranking. The phage clones were ranked by the combined results of the phage ELISA and DNA sequencing. Peptide sequences that occurred multiple times were considered candidates for modification. In addition, each of the peptide encoding nucleotide sequences (Section 5.B.) were correlated to ELISA data. The peptides expressed by phage clones yielding higher $OD_{450}$ readings in the NGF-coated wells relative to the $OD_{450}$ readings they produced in the corresponding streptavidin-coated wells were also considered for modification. A monomer of each peptide sequence selected for modification based on these criteria (SEQ ID NOS:1-29) was fused in-frame to the Fc region of human IgG1 (i.e., modified peptides) as described in Example 2.

B. Consensus sequence determination. From the TN8-IX library, two different consensus sequences were determined. They were: X C WF/WS/TEEG C X X X (SEQ ID NO:274), and X L/FQC X F/YS X X G C P X X (SEQ ID NO:275). The underlined "core amino acid sequences" were obtained by determining the most frequently occurring amino acid in each position. The two cysteines adjacent to the core sequences were fixed amino acids in the TN8-IX library. An LQS motif followed by the fixed cysteine was observed in many sequences from the TN12-I library:

X X X C X X X X X X X L Q S C X X X (SEQ ID NO:276). However, there was no highly conserved motif found in the sequences obtained from the Linear library.

Example 2

Construction of Peptide-Fc Fusion Products

The candidate peptide sequences selected as described above were used to construct fusion proteins in which a monomer of each peptide was fused in-frame to the Fc region of human IgG1. Each modified peptide was constructed by annealing the pairs of oligonucleotides ("oligos") indicated in Table 3 to generate a duplex encoding the peptide and a linker comprised, depending on the peptide, of five glycine residues, one leucine residue and one glutamic acid residue as an NdeI to XhoI fragment. These duplex molecules were ligated into a vector (pAMG21-Fc N-terminal, described further below) containing the human Fc gene, also digested with NdeI and XhoI. The resulting ligation mixtures were transformed by electroporation into *E. coli* strain 2596 cells (GM221, described further below). Clones were screened for the ability to produce the recombinant protein product and to possess the gene fusion having a correct nucleotide sequence. A single such clone was selected for each of the modified peptides (i.e., Fc-peptide fusion products). The peptide portions of samples NGF-C12 through NGF-C18 were consensus sequences based on the analysis described above.

TABLE 3

Anti-NGF Peptides and Oligonucleotides used to Generate Modified Anti-NGF Peptides

| SEQ ID NO: | Sequence of Peptide Portion of Fc-Peptide Fusion Product | SEQ ID NO: for Sense oligo | SEQ ID NO: for Anti-sense oligo |
|---|---|---|---|
| 1 | TGYTEYTEEWPMGFGYQWSF | 149 | 150 |
| 2 | TDWLSDFPFYEQYFGLMPPG | 151 | 152 |
| 3 | FMRFPNPWKLVEPPQGWYYG | 153 | 154 |
| 4 | VVKAPHFEFLAPPHFHEFPF | 155 | 156 |
| 5 | FSYIWIDETPSNIDRYMLWL | 157 | 158 |
| 6 | VNFPKVPEDVEPWPWSLKLY | 159 | 160 |
| 7 | TWHPKTYEEFALPFFVPEAP | 161 | 162 |
| 8 | WHFGTPYIQQQPGVYWLQAP | 163 | 164 |
| 9 | VWNYGPFFNNFPDSTYFLHE | 165 | 166 |
| 10 | WRIHSKPLDYSHVWFFPADF | 167 | 168 |
| 11 | FWDGNQPPDILVDWPWNPPV | 169 | 170 |
| 12 | FYSLEWLKDHSEFFQTVTEW | 171 | 172 |
| 13 | QFMELLKFFNSPGDSSHHFL | 173 | 174 |
| 14 | TNVDWISNNWEHMKSFFTED | 175 | 176 |
| 15 | PNEKPYQMQSWFPPDWPVPY | 177 | 178 |
| 16 | WSHTEWVPQVWWKPPNHFYV | 179 | 180 |
| 17 | WGEWINDAQVHMHEGFISES | 181 | 182 |
| 18 | VPWEHDHDLWEIISQDWHIA | 183 | 184 |

TABLE 3-continued

Anti-NGF Peptides and Oligonucleotides used to
Generate Modified Anti-NGF Peptides

| SEQ ID NO: | Sequence of Peptide Portion of Fc-Peptide Fusion Product | SEQ ID NO: for Sense oligo | SEQ ID NO: for Anti-sense oligo |
|---|---|---|---|
| 19 | VLHLQDPRGWSNFPPGVLEL | 185 | 186 |
| 20 | IHGCWFTEEGCVWQ | 129 | 130 |
| 21 | YMQCQFARDGCPQW | 131 | 132 |
| 22 | KLQCQYSESGCPTI | 133 | 134 |
| 23 | FLQCEISGGACPAP | 135 | 136 |
| 24 | KLQCEFSTSGCPDL | 137 | 138 |
| 25 | KLQCEFSTQGCPDL | 139 | 140 |
| 26 | KLQCEFSTSGCPWL | 141 | 142 |
| 27 | IQGCWFTEEGCPWQ | 143 | 144 |
| 28 | SFDCDNPWGHVLQSCFGF | 145 | 146 |
| 29 | SFDCDNPWGHKLQSCFGF | 147 | 148 |

Construction of pAMG21-Fc N-Terminal Vector pAMG21

Expression plasmid pAMG21 (ATCC No. 98113) is derived from expression vector pCFM1656 (ATCC No. 69576) and the expression vector system described in U.S. Pat. No. 4,710,473, by following the procedure described in published International Patent Application WO 00/24782 (see the portion of Example 2 therein extending from pages 100-103, as well as FIGS. 17A and 17B).

Fc N-terminal Vector

The DNA sequence of the pAMG21-Fc N-terminal vector inserted into expression plasmid pAMG21 between the NdeI and BamHI restriction sites is shown in FIG. 3; top strand, SEQ ID NO: 61, bottom strand SEQ ID NO: 62.

The DNA sequences encoding the thirty peptides (SEQ ID NOS: 1-29) generated for splicing into the above vector and expression as Fc-peptide fusion products are represented by SEQ ID NOS: 63 to 91, inclusive. These DNA sequences include a codon for Met$^{-1}$ (this feature is optional).

The sequences of the corresponding "methionyl mature" peptides encoded by these DNA sequences, i.e., expressed with a methionine residue at the N-terminus, are represented by SEQ ID NOS: 92-120, inclusive.

In addition to making these modified peptides as N-terminal fusions to Fc, some of them were also made as C-terminal fusion products. The vector used for making the C-terminal fusion products is described below.

Fc C-terminal Vector

The DNA sequence of the pAMG21-Fc C-terminal vector inserted into expression plasmid pAMG21 between the NdeI and BamHI restriction sites is shown in FIG. 4; top strand, SEQ ID NO: 121, bottom strand, SEQ ID NO: 122.

GM221 (#2596). Host strain #2596, used for expressing Fc-peptide fusion proteins, is an *E. coli* K-12 strain modified to contain both the temperature sensitive lambda repressor cI857s7 in the early ebg region and the lacI$^Q$ repressor in the late ebg region. The presence of these two repressor genes allows the use of this host with a variety of expression systems, but the repressors are irrelevant to expression from lUXP$_R$. Details regarding its construction are found in WO 00/24782 (see Example 2 therein).

Expression in *E. coli*. Cultures of each of the pAMG21-Fc fusion constructs in *E. coli* GM221 were grown at 37° C. in Terrific Broth medium (See Tartof and Hobbs, "Improved media for growing plasmid and cosmid clones", Bethesda Research Labs Focus, Volume 9, page 12, 1987, cited in aforementioned Sambrook et al. reference). Induction of gene product expression from the luxPR promoter was achieved following the addition of the synthetic autoinducer, N-(3-oxohexanoyl)-DL-homoserine lactone, to the culture medium to a final concentration of 20 nanograms per milliter (ng/ml). Cultures were incubated at 37° C. for an additional six hours. The bacterial cultures were then examined by microscopy for the presence of inclusion bodies and collected by centrifugation. Refractile inclusion bodies were observed in induced cultures, indicating that the Fc-fusions were most likely produced in the insoluble fraction in *E. coli*. Cell pellets were lysed directly by resuspension in Laemmli sample buffer containing 10% β-mercaptoethanol and then analyzed by SDS-PAGE. In each case, an intense coomassie-stained band of the appropriate molecular weight was observed on an SDS-PAGE gel.

Purification. Cells were broken in water (1/10) using high pressure homogenization (two passes at 14,000 PSI), and inclusion bodies were harvested by centrifugation (4000 RPM in a J-6B centrifuge, for one hour). Inclusion bodies were solubilized in 6 M guanidine, 50 mM Tris, 10 mM DTT, pH 8.5, for one hour at a 1/10 ratio. For linear peptides fused to Fc, the solubilized mixture was diluted twenty-five times into 2 M urea, 50 mM Tris, 160 mM arginine, 2 mM cysteine, pH 8.5. The oxidation was allowed to proceed for two days at 4° C., allowing formation of the disulfide-linked compound (i.e., Fc-peptide homodimer). For cyclic peptides fused to Fc, this same protocol was followed with the addition of the following three folding conditions: (1) 2 M urea, 50 mM Tris, 160 mM arginine, 4 mM cysteine, 1 mM cystamine, pH 8.5; (2) 4 M urea, 20% glycerol, 50 mM Tris, 160 mM arginine, 2 mM cysteine, pH 8.5; and (3) 4 M urea, 20% glycerol, 50 mM Tris, 160 mM arginine, 4 mM cysteine, 1 mM cystamine, pH 8.5. The refolded protein was dialyzed against 1.5 M urea, 50 mM NaCl, 50 mM Tris, pH 9.0. The pH of this mixture was lowered to pH 5 with acetic acid. The precipitate was removed by centrifugation, and the supernatant was adjusted to a pH of from 5 to 6.5, depending on the isoelectric point of each fusion product. The protein was filtered and loaded at 4° C. onto an SP-Sepharose HP column equilibrated in 20 mM NaAc, 50 mM NaCl at the pH determined for each construct. The protein was eluted using a 20-column volume linear gradient in the same buffer ranging from 50 mM NaCl to 500 mM NaCl. The peak was pooled and filtered.

Example 3

In vitro NGF-Inhibition Activity of Modified Peptides

The effectiveness of the modified peptides (Fc fusion products) prepared in Example 2 as inhibitors of NGF activity (i.e., NGF "neutralization") was evaluated by measuring the ability of each modified peptide to block NGF induction of vanilloid receptor-1 (VR1) expression.

Dorsal Root Ganglion Neuronal Cultures. Dorsal root ganglia (DRG) were dissected one by one under aseptic conditions from all spinal segments of embryonic 19-day old (E19) rats that were surgically removed from the uterus of timed-pregnant, terminally anesthetized Sprague-Dawley rats (Charles River, Wilmington, Mass.). DRG were collected in ice-cold L-15 media (GibcoBRL, Grand Island, N.Y.) containing 5% heat inactivated horse serum (GibcoBRL), and any loose connective tissue and blood vessels were removed. The DRG were rinsed twice in $Ca^{2+}$- and $Mg^{2+}$-free Dulbecco's phosphate buffered saline (DPBS), pH 7.4 (GibcoBRL). The DRG were then dissociated into single cell suspension using a papain dissociation system (Worthington Biochemical Corp., Freehold, N.J.). Briefly, DRG were incubated in a digestion solution containing 20 U/ml of papain in Earle's Balanced Salt Solution (EBSS) at 37° C. for fifty minutes. Cells were dissociated by trituration through fire-polished Pasteur pipettes in a dissociation medium consisting of MEM/Ham's F12, 1:1, 1 mg/ml ovomucoid inhibitor and 1 mg/ml ovalbumin, and 0.005% deoxyribonuclease I (DNase). The dissociated cells were pelleted at 200×g for five minutes and re-suspended in EBSS containing 1 mg/ml ovomucoid inhibitor, 1 mg/ml ovalbumin and 0.005% DNase. Cell suspension was centrifuged through a gradient solution containing 10 mg/ml ovomucoid inhibitor, 10 mg/ml ovalbumin at 200×g for six minutes to remove cell debris, and then filtered through a 88-μm nylon mesh (Fisher Scientific, Pittsburgh, Pa.) to remove any clumps. Cell number was determined with a hemocytometer, and cells were seeded into poly-ornithine 100 μg/ml (Sigma, St. Louis, Mo.) and mouse laminin 1 μg/ml (GibcoBRL)-coated 96-well plates at $10 \times 10^3$ cells/well in complete medium. The complete medium consisted of minimal essential medium (MEM) and Ham's F12, 1:1, penicillin (100 U/ml), streptomycin (100 μg/ml), and 10% heat inactivated horse serum (GibcoBRL). The cultures were kept at 37° C., 5% $CO_2$ and 100% humidity. For controlling the growth of non-neuronal cells, 5-fluoro-2'-deoxyuridine (75 μM) and uridine (180 μM) were included in the medium.

Treatment with NGF and anti-NGF. Two hours after plating, cells were treated with recombinant human β-NGF or recombinant rat β-NGF at a concentration of 10 ng/ml (0.38 nM). Positive controls comprising serial-diluted anti-NGF antibody (R&D Systems, Minneapolis, Minn.) were applied to each culture plate. Modified peptides (from Example 2) were added at ten concentrations using 3.16-fold serial dilutions. All of the samples were diluted in complete medium before being added to the cultures. Incubation time was 40 hours prior to measurement of VR1 expression.

Measurement of VR1 Expression in DRG Neurons. Cultures were fixed with 4% paraformaldehyde in Hanks' balanced salt solution for fifteen minutes, blocked with Superblock (Pierce, Rockford, Ill.), and permeabilized with 0.25% Nonidet P-40 (Sigma) in Tris.HCl (Sigma)-buffered saline (TBS) for one hour at room temperature. Cultures were rinsed once with TBS containing 0.1% Tween 20 (Sigma) and incubated with rabbit anti-VR1 IgG (prepared at Amgen) for one and one-half hours at room temperature, followed by incubation of Eu-labeled anti-rabbit second antibody (Wallac Oy, Turku, Finland) for one hour at room temperature. Washes with TBS (3× five minutes with slow shaking) were applied after each antibody incubation. Enhance solution (150 μl/well, Wallac Oy) was added to the cultures. The fluorescence signal was then measured in a time-resolved fluorometer (Wallac Oy). VR1 expression in samples treated with the modified peptides was determined by comparing to a standard curve of NGF titration from 0-1000 ng/ml. Percent inhibition (compared to maximum possible inhibition) of NGF effect on VR1 expression in DRG neurons was determined by comparing to controls that were not NGF-treated. Results are given in Table 4. The effectiveness of a sampling of the peptides identified in Example 1, Section 6, paragraph A was also determined in the manner described above (data not shown).

TABLE 4

Neutralizing Activity of Modified Peptides In Vitro

| SEQ ID NO: | Peptide Portion of Fusion Product | Attachment of Peptide Portion to Fc | Activity of Modified Peptide |
|---|---|---|---|
| 1 | TGYTEYTEEWPMGFGYQWSF | | − |
| 2 | TDWLSDFPFYEQYFGLMPPG | | + |
| 2 | TDWLSDFPFYEQYFGLMPPG | C-term | − |
| 3 | FMRFPNPWKLVEPPQGWYYG | | n/a |
| 4 | VVKAPHFEFLAPPHFHEFPF | | + |
| 4 | VVKAPHFEFLAPPHFHEFPF | C-term | − |
| 5 | FSYIWIDETPSNIDRYMLWL | | − |
| 6 | VNFPKVPEDVEPWPWSLKLY | | + |
| 6 | VNFPKVPEDVEPWPWSLKLY | C-term | + |
| 7 | TWHPKTYEEFALPFFVPEAP | | + |
| 8 | WHFGTPYIQQQPGVYWLQAP | | + |
| 9 | VWNYGPFFMNFPDSTYFLHE | | + |
| 10 | WRIHSKPLDYSHVWFFPADF | | + |
| 10 | WRIHSKPLDYSHVWFFPADF | C-term | + |
| 11 | FWDGNQPPDILVDWPWNPPV | | + |
| 11 | FWDGNQPPDILVDWPWNPPV | C-term | − |
| 12 | FYSLEWLKDHSEFFQTVTEW | | n/a |
| 13 | QFMELLKFFNSPGDSSRHFL | | − |
| 14 | TNVDWISNNWEHMKSFFTED | | + |
| 14 | TNVDWISNNWEHMKSFFTED | C-term | + |
| 15 | PNEKPYQMQSWFPPDWPVPY | | − |
| 16 | WSHTEWVPQVWWKPPNHFYV | | n/a |
| 17 | WGEWINDAQVHMHEGFISES | | − |
| 18 | VPWEHDHDLWEIISQDWHIA | | + |
| 18 | VPWEHDHDLWEIISQDWHIA | C-term | − |
| 19 | VLHLQDPRGWSNFPPGVLEL | | n/a |
| 20 | IHGCWFTEEGCVWQ | | n/a |
| 21 | YMQCQFARDGCPQW | | + |
| 22 | KLQCQYSESGCPTI | | + |
| 23 | FLQCEISGGACPAP | | − |
| 24 | KLQCEFSTSGCPDL | | + |
| 25 | KLQCEFSTQGCPDL | | + |
| 26 | KLQCEFSTSGCPWL | | + |

TABLE 4-continued

Neutralizing Activity of Modified Peptides In Vitro

| SEQ ID NO: | Peptide Portion of Fusion Product | Attachment of Peptide Portion to Fc | Activity of Modified Peptide |
|---|---|---|---|
| 27 | IQGCWFTEEGCPWQ | | + |
| 28 | SFDCDNPWGHVLQSCFGF | | − |
| 29 | SFDCDNPWGHKLQSCFGF | | − |

"+" indicates at least 50% inhibition of NGF induced activity observed at modified peptide concentrations of 18 μM or lower.
"-" indicates less than 50% inhibition of NGF induced activity observed at modified peptide concentrations of at least 18 μM.
"n/a" means not applicable.
Peptides are attached to the N-terminus of Fc unless designated "C-term" wherein such peptides are attached to the C-terminus of Fc.

Example 4

Identification of Additional Peptides Capable of Modulating NGF Activity

I. Construction of Secondary Anti-NGF Peptide Libraries

A. Electrocompetent *E. coli* cells. *E. coli* XL1-Blue MRF' electroporation competent cells were purchased from Stratagene Cloning Systems, La Jolla, Calif. (catalog no. 200158).

B. Modification of pCES1 vector. A PCR reaction was performed using Extend Long Template PCR Systems (Roche Diagnostics Corp., Indianapolis, Ind.) with 1 μg of pCES1 vector (TargetQuest Inc., now Dyax Corp., Cambridge, Mass.) as a template. The volume of PCR mixture was 100 μl and contained 1×PCR buffer, 200 nM of each of the primers, 5'-CAAACGAATGGATCCTCATTAAAGCCAGA-3' (SEQ ID NO: 191) and 5'-GGTGGTGCGGCCGCACTCGAGACTGTTGAAAGTTGTTTAGCA-3' (SEQ ID NO: 192), 200 nM dNTP, and 3 units of Tag DNA polymerase. A TRIO-Thermoblock (Biometra, Göttingen, Germany) PCR system was used to run the following program: 94° C. for 5 minutes; 30 cycles of [94° C. for 30 seconds, 50° C. for 30 seconds, 72° C. for 45 seconds]; 72° C. for 10 minutes; cool to 4° C. The PCR products were run on a 1% agarose gel and purified with a Qiagen Spin Column (Qiagen Inc., Valencia, Calif.) in accordance with the manufacturer's protocols. A second PCR reaction was performed with 5 μl of PCR products and 200 nM of each of the two primers, 5'-CAAACGAATGGATCCTCATTAAAGCCAGA-3' and 5'-AACACAAAAGTGCACAGGGTGGAGGTGGTGGTGCGGCCGCACT-3' (SEQ ID NOS: 191 and 193, respectively), using the same PCR conditions as described above. The PCR products and original pCES1 vector were digested separately in a 100-μl reaction containing 1×NEB2 buffer, 60 units of ApaLI (New England Biolabs, Beverly, Mass.), 60 units of BamHI (New England Biolabs) at 37° C. for one hour. Both digested DNA molecules were purified with a Qiagen Spin Column and ligated together in a 40-ul reaction containing 1× ligation buffer and 40 units of T4 DNA ligase (New England Biolabs) at room temperature, overnight.

The vectors were transfected into *E. coli* cells and incubated at 37° C., overnight. Isolated single colonies were selected, and plasmid was purified with Qiagen Spin Column. The correct insert was confirmed by DNA sequencing.

C. Preparation of vector DNA. One microgram of the modified pCES1 vector DNA (Section I.B., above) was transformed into 40 μl of electrocompetent XL1-blue *E. coli* (Section I.A.) using a Gene Pulser II (Bio-Rad Labs, Hercules, Calif.) with the setting of 2500 V, 25 μF, and 200 ohms. The transformed bacteria sample was then transferred immediately into a tube containing 960 μl of SOC (2% tryptone, 0.5% yeast extract, 10 mM NaCl, 2.5 mM KCl, 20 mM glucose, 10 MM $MgSO_4$, 10 mM $MgCl_2$), and this culture was allowed to grow at 37° C., with shaking, for one hour. The cells were then spread onto a plate of 2×YT agar supplemented with 100 μg/ml of ampicillin, 12.5 μg/ml of tetracycline and 2% glucose (2×YTAGT; Invitrogen Corporation, Carlsbad, Calif.) and incubated at 37° C. overnight. A single colony was confirmed by sequencing and used to inoculate two liters of 2×YTAGT media at 37° C., with shaking, overnight. The plasmid vector DNA was purified with a Qiagen Plasmid Maxi Kit according to the manufacturer's protocols.

D. Digestion of vector DNA. A total of about 1,100 micrograms of vector DNA was digested in two batches. Eight hundred micrograms of vector DNA (Section I.C.) was digested at 37° C. in a 1500 μl reaction containing 1×NEB buffer 2, 1000 units of ApaLI and 1000 units of XhoI, overnight. The remaining 300 micrograms of vector DNA (Section I.C.) was digested in a 500-μl reaction containing 1×NEB buffer 2, 300 units of ApaLI, and 300 units of XhoI at 37° C. overnight. Both restriction digest reactions were incubated overnight at 37° C. and analyzed in a pre-made 0.8% agarose gel (Embi Tec, San Diego, Calif.). The linearized vector DNA was excised from the gel and extracted with QIAquick Gel Extraction Kit (Qiagen Inc.) in accordance with the manufacturer's directions.

E. Preparation of library oligonucleotides. Six library oligonucleotides (two fixed and four doped) were designed based on the sequences derived from previous work. The two fixed library oligonucleotides were 5'-CACAGTGCACAGGGTNNKNNKNNKNNKNNKNNKNNKCTGCAGNNKS ARTWTAGCNNKNNKNNKNNKNNKNNKNNKCATTCTCTCGAGATCA-3' and 5'-CACAGTGCACAGGGTNNKNNKNNKAAACTGCAGNNKGAATTTAGCACCAGC GGCNNKCCGGATCTGNNKNNKNNKCATTCTCTCGAGATCA-3' (SEQ ID NOS:194 and 195, respectively; N and K represents an equal representation of nucleotides A,G,C,T and G,T during oligo synthesis, respectively,). The three 70%-doped library oligo-nucleotides were 5'-CACAGTGCACAGGGT NNKNNKNNKNNKNNKNNKNNKKtgKttKacKgaKgaKggKNNKNNKNNKNNKNNKN NKNNKCATTCTCTCGAGATCA-3', 5'-CACAGTGCACAGGGTNNKKttKtgKga KggKaaKcaKccKccKgaKatKttKgtKgaKtgKccKtgKaaKccKccKgtKNNK CATTCTCTCGAGATCA-3', and 5'-CACAGTGCACAGGGTNNKacKgaKtg KctKagKgaKttKccKttKtaKgaKcaKtaKttKggKctKatKccKccKggKNN KCATTCTCTCGAGATCA-3' (SEQ ID NOS: 196, 197, and 198, respectively; lower case letters represent a mixture of 70% of the indicated base and 10% of each of the other three nucleotides) The 91% doped library oligo was 5'-CACAGTGCACAGGGTNNKNNKNNKaaKctKcaKNNKgaKttKtcKacKtcKg gKNNKccKgaKctKNNKNNKNNKCATTCTCTCGAGATCA-3' (SEQ ID NO: 199; lower case letters represent a mixture of 91% of the indicated base and 3% of each of the other three nucleotides). All were synthesized by the Amgen DNA synthesis group. Each of these oligonucleotides was used as a template in a Polymerase Chain Reaction (PCR).

An Expand High Fidelity PCR System kit (Roche Diagnostics Corp.) was used for PCR reactions. Each PCR reaction comprised 2400 µl in volume, and half of the volume contained 1 nM of a library oligonucleotide while the other half contained 10 nM of a library oligonucleotide, 1×PCR buffer, 300 nM of each of the primers, 5'-CACAGT-GCACAGGGT-3' (SEQ ID NO: 200) and 5'-TGATCTC-GAGAGAATG-3' (SEQ ID NO: 201), 200 µM dNTP, 2 mM $MgCl_2$, and 84 units of Expand polymerase. A thermocycler (GeneAmp PCR System 9700, Applied Biosystems, Foster City, Calif.) was used to run the following program: 94° C. for 5 minutes; 30 cycles of [94° C. for 30 seconds, 55° C. for 30 seconds, 72° C. for 45 seconds]; 72° C. for 7 minutes; cool to 4° C. The free nucleotides were removed using the QIAquick PCR Purification Kit (Qiagen Inc., Catalog No. 28104) in accordance with the manufacturer's protocols.

F. Digestion of library oligonucleotides. Each of the PCR products from the 2400-µl reaction (Section I.E.) was digested in a 500 µl reaction that contained 1×NEB buffer2, 250 units of ApaLI, and 250 units of XhoI at 37° C., overnight. The digested DNA was separated on a pre-made 3% agarose gel (Embi Tec). The DNA band of interest from each reaction was cut from the gel and extracted with a QIAquick Gel Extraction Kit.

G. Ligation of vector with library oligonucleotides. The linearized vector (Section I.D.) and each digested PCR product (Section I.F.) were ligated at a 1:5 molar ratio in two batches: the first batch included one fixed library oligonucleotide and three doped library oligonucleotides in a 800 µl reaction containing 1×NEB ligation buffer and 20,000 units of the T4 DNA ligase at 16° C., overnight; the second batch included two fixed library oligonucleotides and one doped library oligonucleotide in a 400 µl reaction containing 1×NEB ligation buffer and 20,000 units of T4 DNA ligase at 16° C., overnight. The ligated products were incubated at 65° C. for twenty minutes to inactivate the T4 DNA ligase and further incubated with 100 units of NotI at 37° C. for two hours to minimize vector self-ligation. The ligated products were then purified by a standard phenol/chloroform extraction (Molecular Cloning, Maniatis, et al., 3rd Edition) and resuspended in 100 µl of water.

H. Electroporation Transformation. For each library, ten electroporation reactions were performed. For each transformation, 10 µl of ligated vector DNA (Section I.G.) and 300 µl of XL1-BLUE MRF' cells (Section I.A.) were mixed in a 0.2-cm cuvette (Bio-Rad Labs). The resulting mixture was pulsed with a Gene Pulser II, with a setting of 2500 V, 25 µF, and 200 ohms. The transformed bacteria from the ten electroporation reactions were combined and transferred into a flask containing 30 ml of SOC for incubation at 37° C. for one hour. The cells were then added to 400 ml of 2×YTAGT and grown at 37° C., with shaking, for five hours. The cells were then centrifuged at 4000 rpm for fifteen minutes at 4° C. The cell pellets were then resuspended in 12 ml of 2×YT broth containing 15% glycerol and stored at −80° C. This was the primary stock for the libraries. Titers showed library sizes of $2.5 \times 10^9$ (library number 93), $2.5 \times 10^9$ (library number 59), $5.0 \times 10^9$ (library number 72), $8.0 \times 10^9$ (library number 95), $8.5 \times 10^9$ (library number 39) independent transformants and $1.5 \times 10^9$ (library number 63) independent transformants for the fixed and doped libraries, respectively.

II. Amplification of the Libraries.

A. Making secondary stock of the libraries. The primary library cell stock (Section I.H.) was used to inoculate 1700 ml (for both fixed libraries 93 and 59), and 1800 ml, 2700 ml, 3000 ml, 1000 ml (for doped libraries 72, 95, 39 and 63, respectively) of 2×YTAGT media so that the starting $OD_{600}$ was equal to 0.1. The cultures were allowed to grow at 37° C., with shaking, for several hours until the $OD_{600}$ was 0.5. A one-tenth aliquot from each library were taken out and grown up in separate flasks for another two hours at 37° C. These sub-cultures were centrifuged at 4000 rpm (using a Beckman JA-14 rotor) for 10 minutes at 4° C., and the bacteria pellets (for each library) were resuspended in 9.5 ml of 2×YT containing 15% glycerol/for storage at −80° C.

B. Phage Induction. M13KO7 helper phage aliquots (Amersham Biosciences, Inc., Piscataway, N.J. were added to the remaining bacteria cultures at $OD_{600}$=0.5 (Section II.A.) to a final concentration of $3 \times 10^9$ pfu/ml. The helper phages were allowed to infect bacteria at 37° C. for thirty minutes without shaking and thirty minutes with slow shaking. The infected cells were centrifuged with 5000 rpm for fifteen minutes at 4° C. The cell pellets were resuspended in the same volume (Section II.A.) with 2YT broth with 100 µg/ml of ampicillin, 40 µg/ml of kanamycin and 12.5 µg/ml of tetracycline (2×YTAKT). The phagemid production was allowed to occur at 30° C. overnight while shaking.

C. Harvest of phage. The bacteria cultures (Section II.B.) were centrifuged at 5000 rpm for fifteen minutes at 4° C. The supernatants were transferred into new bottles, and 0.2 volume of 20% PEG/2.5M NaCl was added and incubated on ice for one hour to precipitate the phagemids. Precipitated phagemids were centrifuged at 10,000 rpm for thirty minutes at 4° C. and carefully resuspended with 100 ml of cold PBS. The phagemid solution was further purified by centrifuging away the remaining cells with 4000 rpm for ten minutes at 4° C. and precipitating the phagemids by adding 0.2 volume of 20% PEG/2.5M NaCl. The phagemids were centrifuged at 10,000 rpm for thirty minutes at 4° C., and the phagemid pellets were resuspended using 18 ml of cold PBS. Six milliliters of 60% glycerol solution were added to the phagemid solution for storage at −80° C. The phagemid titers were determined by a standard procedure (see Molecular Cloning, Maniatis, et al., 3rd Edition).

III. Selection of Human NGF Binding Phages.

A. Biotinylation of human NGF. One milligram of human NGF was biotinylated using an EZ-Link Sulfo-NHS-LC-Biotinylation Kit (Pierce, Rockford, Ill.) in accordance with the manufacturer's directions.

B. Immobilization of NGF on magnetic beads. Biotinylated NGF (Section III.A.) was immobilized on Dynabead M-280 Streptavidin (DYNAL, Lake Success, N.Y.) at a concentration of 200 ng NGF per 100 µl of bead stock from the manufacturer. After drawing the beads to one side of a tube using a magnet and then pipetting away the liquid, the beads were washed twice with the phosphate buffer saline (PBS) and resuspended in PBS. The biotinylated NGF protein was added to the washed beads at the above concentration and incubated, with rotation, for one hour at room temperature. The NGF-coated beads were then blocked by adding BSA to 2% final concentration and incubating overnight at 4° C., with rotation. The resulting NGF-coated beads were washed twice with PBST (PBS with 0.05% Tween-20) before being subjected to the selection procedures described in the next section.

C. Selection using the NGF-coated beads. Approximately 1000-fold library equivalent phagemids (Section II.C.) were blocked for one hour with 1 ml of PBS containing 2% BSA. The blocked phagemid sample was subjected to two negative selection steps by adding to blank beads (the same beads as Section III.B. but without an NGF coating), and this mixture was incubated at room temperature for fifteen minutes, with rotation. The phagemid containing supernatant was drawn out using a magnet and transferred to a second tube containing blank beads, and this mixture was incubated at room temperature for fifteen minutes, with rotation. The phagemid-containing supernatant was drawn out using magnet and transferred to a new tube containing NGF-coated beads (Section III.B.), and this mixture was incubated at room temperature for one hour, with rotation. After the supernatant was discarded, the phagemid-bound beads were washed ten times with 2% milk-PBS; ten times with 2% BSA-PBS; ten times with PBST, and twice with PBS. The phagemids (from libraries 72, 95, 39) were then allowed to elute in 1 ml of 100 mM triethylamine solution (Sigma, St. Louis, Mo.) for ten minutes on a rotator. The pH of the phagemid-containing solution was neutralized by adding 0.5 ml of 1 M Tris-HCl (pH 7.5). The phagemids (from libraries 93, 59, 63) were eluted in 1 ml of 100 nM, 1000 nM and 100 mM TEA sequentially. The resulting phagemids were used to infect 5 ml of freshly grown XL1-Blue MRF' bacteria ($OD_{600}$=about 0.5) at 37° C. for thirty minutes without shaking and thirty minutes with slow shaking. All of the infected XL1-BLUE MRF' cells were plated on a large 2×YTAG plate and incubated at 30° C. overnight.

D. Induction and harvesting of phage. A 10 ml aliquot of 2×YTAGT media was added to the plate (Section III.C.) to resuspend XL1-BLUE MRF' cells. All XL1-BLUE MRF' cells were collected in a tube, and a 250 µl aliquot of these cells was added to 25 ml of 2×YTAGT and grown at 37° C. until the $OD_{600}$ was equal to 0.5. M13KO7 helper phages were added to a concentration of $3 \times 10^9$ cfu/ml and incubated at 37° C. for thirty minutes without shaking and 30 minutes with slow shaking. The cells were centrifuged with 5000 rpm for 10 minutes at 4° C. and resuspended with 25 ml of 2×YTAK. The bacteria were allowed to grow at 30° C. overnight, with shaking. The induced phagemids were harvested and purified as described in Section II.C.

E. Second round selection. The second round selection was performed as outlined in Sections III.B. and III.C., except as follows. Approximately 100-fold library equivalent phagemids resulting from Section III.D. were used as the input phagemid.

F. Third round selection. A third round selection was performed as outlined in Sections III.B. and III.C., except as follows. Approximately 10-fold library equivalent phagemids resulting from Section III.E. was used as the input phagemid. Only 20 ng of biotinylated NGF (Section III.A.) was used to coat the Dynabead M-280 Streptavidin. The phage-bound beads were washed ten times with 2% milk-PBS; ten times with 2% BSA-PBS; and ten times with PBST, in which the final wash involved thirty minutes of incubation at room temperature in PBST. The beads were washed twice with PBS.

G. Fourth round selection. A fourth round selection was performed as outlined in Sections III.B. and III.C., except for the following. Approximately one-fold library equivalent phagemids resulting from Section 3.F. were used as the input phagemid. Only two nanograms of biotinylated NGF (Section III.A.) were used to coat the Dynabead M-280 Streptavidin. The phage-bound beads were same as in round three.

IV. Clonal Analysis

A. Preparation of master plate. Single colonies from the second round selection were picked and inoculated into 96-well plates containing 120 µl of 2×YTAGT per well. The 96-well plates were incubated at 30° C. in a shaker overnight. Forty microliters of 60% glycerol were added per well for storage at −80° C.

B. Phagemid deep-well ELISA. About 20 µl aliquots of cells from the master plate (Section IV.A.) were inoculated into a fresh Costar® 96-well two milliliter assay block (Corning Inc., Corning, N.Y., Catalog No. 3960) containing 500 µl of 2×YTAGT per well, and this new plate of cells was grown at 37° C. until the $OD_{600}$ was approximately equal to 0.5. Forty microliters of 2×YTAGT containing M13KO7 helper phage ($1.5 \times 10^{10}$ cfu/ml) were added to each well, and the 96-well plate was incubated at 37° C. for thirty minutes without shaking and another thirty minutes with slow shaking. The plate was centrifuged at 2000 rpm (Beckman CS-6R tabletop centrifuge) for ten minutes at 4° C. The supernatants were removed from the wells, and each cell pellet was resuspended using 500 µl of 2×YTAKT per well. The plate was incubated at 30° C. overnight for phagemid expression.

Human NGF was coated onto the 96-well Maxisorp plate (NUNC) at a concentration of 5 µg/ml in 1×PBS at 4° C., overnight. As a control, BSA (Sigma) was coated onto a separate Maxisorp plate at 5 µg/ml.

On the following day, the overnight cell cultures were centrifuged at 2000 rpm for ten minutes at 4° C. Twenty microliters of supernatant from each well were transferred to a new 96-well plate containing a BSA/PBS solution so as to dilute the supernatant at 1:2 to 1:10 range. The resulting mixtures were incubated for one hour at room temperature, with shaking, to block the phagemids. Meanwhile, the NGF-coated plate was blocked with 200 µl of 2% BSA/PBS solution per well for one hour at room temperature, while shaking. The BSA solution was discarded, and each well was washed three times with PBS solution. After the final washing step, 100 µl of blocked phagemid solution were added to each well of the NGF-coated plate as well as the control plate and incubated for one hour at room temperature with shaking. The liquid was discarded, and each well was washed three times with PBST solution. One hundred microliters of the HRP-conjugated anti-M13 mAb (Amersham Biosciences, Inc., Piscataway, N.J.) at 5,000 dilution were added to each well of the NGF-coated and control plates, and these plates were incubated for one hour at room temperature, with shaking. The liquids were discarded again, and each well was washed three times with PBST solution. One hundred microliters of LumiGLO chemiluminescent substrates (Kirkegaard & Perry Laboratories, Gaithersburg, Md.) were added to the wells, and each well was read by Luminoskan Ascent DLRearly machine (Labsystems, Franklin, Mass.).

C. Sequencing of the phage clones. PCR reaction was performed using 1 µl of bacteria from each well of the master plate (Section IV.A.) as a template. The volume of each PCR mixture was 50 µl, containing 1×PCR buffer, 300 nM of each of the primers, 5'-GTTAGCTCACTCATTAG-GCAC-3' (SEQ ID NO:281) and 5'-GTACCGTAACACT-GAGTTTCG-3' (SEQ ID NO: 282), 200 µM DNTP, 2 mM $MgCl_2$, and 2.5 units of taq DNA polymerase (Roche Molecular Biochemicals). A GeneAmp PCR System 9700 (Applied Biosystems, Foster City, Calif.) was used to run the following program: 94° C. for 5 minutes; 40 cycles of [94° C. for 45 seconds, 55° C. for 45 seconds, 72° C. for 90 seconds]; 72° C. for 10 minutes; cool to 4° C. The PCR products were purified with QIAquick 96 PCR Purification Kit (Qiagen Inc.) according to the manufacturer's directions. All purified PCR products were sequenced with the primer 5'-CGGATAACAATTTCACACAGG-3' (SEQ ID NO:283), using an ABI 3770 Sequencer (Perkin Elmer) according to the manufacturer's directions.

V. Sequence Ranking. The peptide sequences that were translated from nucleotide sequences (Section IV.C.) were correlated to ELISA data. The peptides considered for modification were those expressed by phage clones that yielded higher $OD_{450}$ readings in the NGF-coated wells relative to the $OD_{450}$ reading produced in the corresponding BSA-coated wells. The peptides encoded by sequences that occurred multiple times were also considered for modification. On these criteria, the top two (2) peptides from library 93, top nine (9) peptides from library 72, top seventeen (17) peptides from library 39, top eleven (11) peptides from library 95, top six (6) peptides from library 59, and top ten (10) peptides from library 63 were selected for modification.

The candidate peptides selected from the affinity matured population were used to construct fusion proteins in which a monomer of each peptide was fused in-frame to the Fc region of human IgG1. For fusion of peptides to the N-terminus of Fc, constructs were made by annealing pairs of oligonucleotides ("oligos") to generate a duplex encoding the peptide and a linker comprised, depending on the peptide, of five glycine residues, one leucine residue and one glutamic acid residue as an NdeI to XhoI fragment. These duplex molecules were ligated into a vector (pAMG21-Fc N-terminal, described above) containing the human Fc gene, also digested with NdeI and XhoI. The resulting ligation mixtures were transformed by electroporation into *E. coli* strain 2596 cells (GM221, described further below). Clones were screened for the ability to produce the recombinant protein product and to possess the gene fusion having a correct nucleotide sequence. A single such clone was selected for each of the modified peptides (i.e., Fc-peptide fusion products) shown in Table 5. For fusion of peptides to the C-terminus of Fc, constructs were made by annealing pairs of oligonucleotides ("oligos") to generate a duplex encoding five glycine residues, one alanine and one glutamine residue, the peptide, followed by one leucine residue and one glutamic acid residue as an ApaLI to XhoI fragment. These duplex molecules were ligated into a vector (pAMG21-Fc C-terminal, described above) containing the human Fc gene, also digested with ApaLI and XhoI. The resulting ligation mixtures were transformed and screened as described above. Truncated versions of select peptides were made by PCR, using the parent construct as template. PCR products encoding the desired sequence were ligated into the parent construct as BsrGI to BamHI, NcoI to BsrGI or NdeI to BsrGI fragments. The resulting ligation mixtures were transformed and screened as described above.

Results from testing of the resulting modified peptides in the DRG neutralization assay (see above for protocol) are given in Table 5. The effectiveness of peptides selected from the affinity matured population may be determined in the DRG neutralization assay in the same manner.

TABLE 5

In vitro NGF Inhibition Activity of Matured Modified Peptides

| Linker (L) Portion of (L)–(P) fusion (SEQ ID NO:) | Peptide (P) Portion of (L)–(P) fusion (SEQ ID NO:) | | In Vivo anti-NGF Activity of Matured Modified Peptide |
|---|---|---|---|
| 285 | 202 | C-term | + |
| 285 | 203 | | + |
| 285 | 204 | | − |
| 285 | 205 | C-term | − |
| 285 | 206 | C-term | − |
| 285 | 207 | | − |
| 285 | 208 | | + |
| 285 | 209 | | + |
| 286 | 210 | C-term | + |
| 285 | 211 | C-term | + |
| 285 | 212 | C-term | − |
| 285 | 213 | C-term | − |
| 285 | 214 | | + |
| 285 | 215 | | + |
| 285 | 216 | C-term | + |
| 285 | 217 | | + |
| 285 | 218 | | − |
| 285 | 219 | C-term | + |
| 285 | 220 | | − |
| 285 | 221 | C-term | + |
| 285 | 222 | | + |
| 285 | 223 | | − |
| 285 | 224 | C-term | + |
| 285 | 225 | C-term | − |
| 285 | 226 | C-term | − |
| 286 | 227 | C-term | + |
| 286 | 228 | | + |
| 285 | 229 | | + |
| 285 | 230 | C-term | + |
| 286 | 231 | C-term | + |
| 285 | 232 | C-term | + |
| 285 | 233 | | + |
| 285 | 234 | | + |
| 285 | 235 | C-term | + |
| 285 | 236 | C-term | + |
| 285 | 237 | C-term | + |
| 285 | 238 | C-term | − |
| 285 | 239 | C-term | + |
| 285 | 240 | | + |
| 285 | 241 | C-term | + |
| 285 | 242 | | − |
| 285 | 243 | | + |
| 285 | 244 | | − |
| 285 | 245 | | − |
| 285 | 246 | | + |
| 286 | 247 | | + |
| 285 | 248 | | − |
| 285 | 249 | | + |
| 285 | 250 | C-term | − |
| 285 | 251 | C-term | + |
| 285 | 252 | | − |
| 285 | 253 | C-term | − |
| 285 | 254 | | + |
| 285 | 255 | | + |
| 285 | 256 | | − |
| 285 | 257 | | − |
| 285 | 258 | C-term | − |
| 285 | 259 | C-term | + |
| 285 | 260 | | − |
| 285 | 261 | | − |
| 285 | 262 | C-term | − |
| 285 | 263 | | + |
| 285 | 264 | | − |
| 285 | 265 | C-term | − |
| 285 | 266 | | + |
| 285 | 267 | | − |
| 285 | 268 | | − |
| 285 | 269 | | − |
| 285 | 270 | | − |
| 285 | 271 | C-term | + |
| 285 | 272 | C-term | + |
| 285 | 279 | C-term | + |

TABLE 5-continued

In vitro NGF Inhibition Activity of Matured Modified Peptides

| Linker (L) Portion of (L)–(P) fusion (SEQ ID NO:) | Peptide (P) Portion of (L)–(P) fusion (SEQ ID NO:) | | In Vivo anti-NGF Activity of Matured Modified Peptide |
|---|---|---|---|
| 285 | 280 | C-term | + |

"+" indicates at least 50% inhibition of NGF induced activity observed at matured modified peptide concentrations of 20 nM or lower
"–" indicates less than 50% inhibition of NGF induced activity observed at matured modified peptide concentrations of at least 20 nM.
"n/a" means not applicable.
*(L)–(P) fusions were attached to the N-terminus of Fc domain (SEQ ID NO: 60 lacking N-terminal methionine) unless designated "C-term" wherein the (L)–(P) fusions were attached to the C-terminus of Fc domain (SEQ ID NO: 60).

Example 5

In vivo Antinociceptive Activity of Anti-NGF Matured Modified Peptides in Rat Pain Models A. Neuropathic Pain Model. Male Sprague-Dawley rats (200 g) were anesthetized with isoflurane inhalant anesthesia and the left lumbar spinal nerves at the level of L5 and L6 were tightly ligated (4-0 silk suture) distal to the dorsal root ganglion and prior to entrance into the sciatic nerve, as first described by Kim and Chung (Kim, S. H.; Chung, J. M. An experimental model for peripheral neuropathy produced by segmental spinal nerve ligation in the rat. Pain 50:355-363, (1992)). The incisions were closed and the rats were allowed to recover. This procedure results in mechanical (tactile) allodynia in the left hind paw as assessed by recording the pressure at which the affected paw (ipsilateral to the site of nerve injury) was withdrawn from graded stimuli (von Frey filaments ranging from 4.0 to 148.1 mN) applied perpendicularly to the plantar surface of the paw (between the footpads) through wire-mesh observation cages. A paw withdrawal threshold (PWT) was determined by sequentially increasing and decreasing the stimulus strength and analyzing withdrawal data using a Dixon non-parametric test, as described by Chaplan et al. (Chaplan, S. R.; Bach, F. W.; Pogrel, J. W.; Chung, J. M.; Yaksh, T. L. Quantitative assessment of tactile allodynia in the rat paw. J. Neurosci. Meth, 53:55-63 (1994)).

Figure 5:
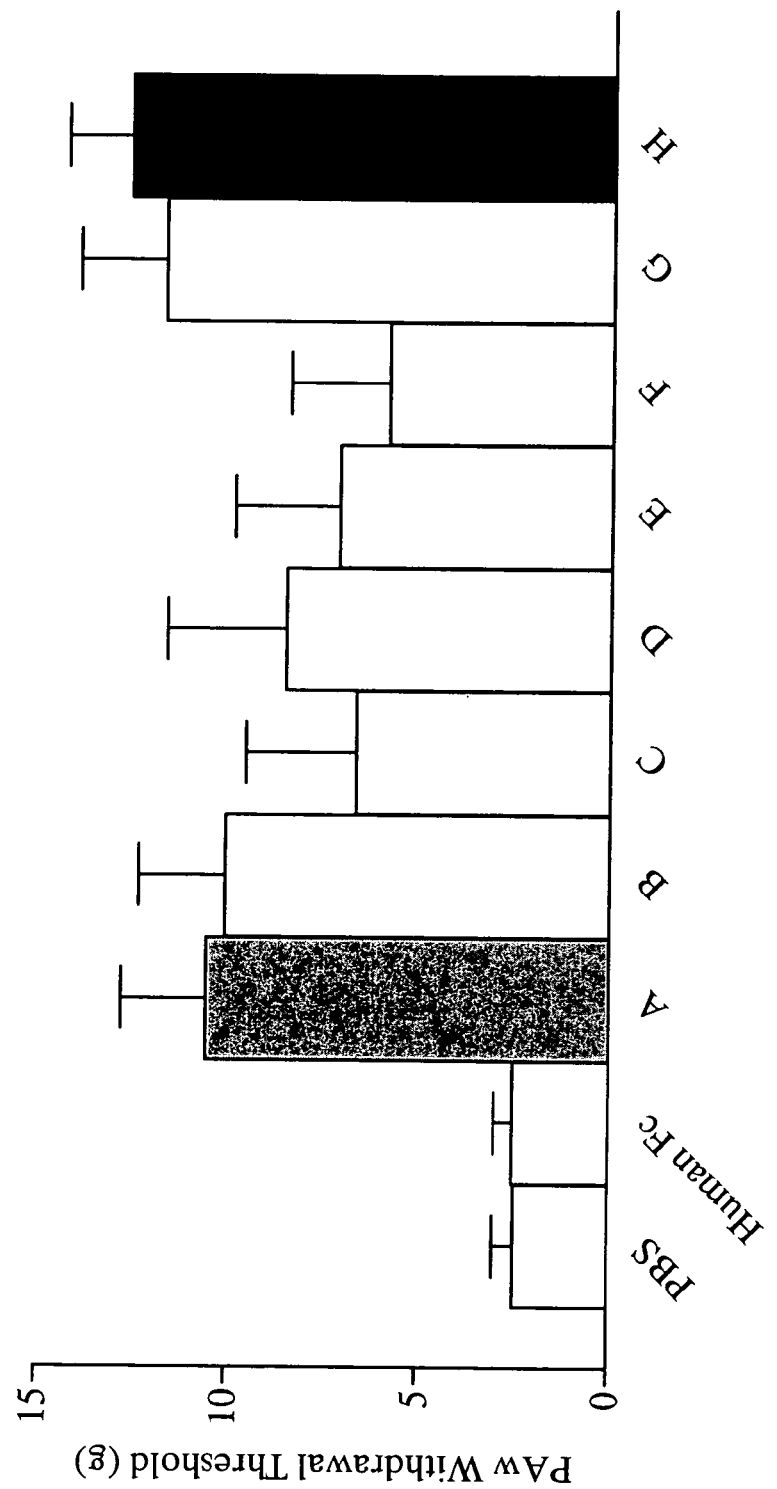
FIG. 5 depicts graphs of the antiallodynic effects of anti-NGF modified peptides (A-H as described in Table 6) in Chung neuropathic pain model in rats (60 mg/kg, s.c., at day 3 or 4 after administration).

Normal rats and sham surgery rats (nerves isolated but not ligated) withstand at least 148.1 mN (equivalent to 15 g) of pressure without responding. Spinal nerve ligated rats respond to as little as 4.0 mN (equivalent to 0.41 g) of pressure on the affected paw. Rats were included in the study only if they did not exhibit motor dysfunction (e.g., paw dragging or dropping) and their PWT was below 39.2 mN (equivalent to 4.0 g). At least seven days after surgery rats were treated with a matured modified peptide previously observed to inhibit at least 50% of NGF induced activity in vitro at concentrations of 20 nM or lower (matured modified peptides designated as "+" in Table 5). Generally, rats were treated with a screening dose of 60 mg/kg of the matured modified peptide or control diluent (PBS) once by s.c. injection and PWT was determined each day thereafter for 7 days (FIG. 5).

B. CFA Inflammatory Pain Model. Male Sprague-Dawley rats (200 g) were lightly anesthetized with isoflurane inhalant anesthesia and the left hindpaw was injected with complete Freund's adjuvant (CFA), 0.15 ml. This procedure results in mechanical (tactile) allodynia in the left hind paw as assessed by recording the pressure at which the affected paw was withdrawn from graded stimuli (von Frey filaments ranging from 4.0 to 148.1 mN) applied perpendicularly to the plantar surface of the paw (between the footpads) through wire-mesh observation cages. PWT was determined by sequentially increasing and decreasing the stimulus strength and analyzing withdrawal data using a Dixon non-parametric test, as described by Chaplan et al. (1994). Rats were included in the study only if they did not exhibit motor dysfunction (e.g., paw dragging or dropping) or broken skin and their PWT was below 39.2 mN (equivalent to 4.0 g).

At least seven days after CFA injection rats were treated with a matured modified peptide previously observed to inhibit at least 50% of NGF induced activity in vitro at concentrations of 20 nM or lower (matured modified peptides designated as "+" in Table 5). Generally, rats were treated with a screening dose of 60 mg/kg of the matured modified peptide or control diluent (PBS) once by s.c. injection and PWT was determined each day thereafter for 7 days. Average paw withdrawal threshold (PWT) was converted to percent of maximum possible effect (% MPE) using the following formula: % MPE=100*(PWT of treated rats−PWT of control rats)/(15−PWT of control rats). Thus, the cutoff value of 15 g (148.1 mN) is equivalent to 100% of the MPE and the control response is equivalent to 0% MPE.

Figure 6:
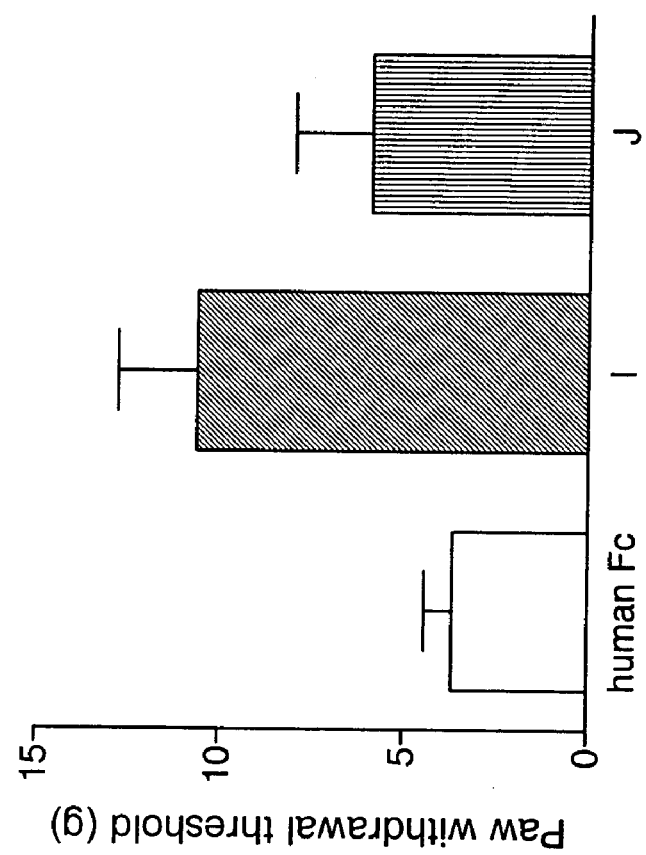
FIG. 6 depicts graphs of the antiallodynic effects of anti-NGF modified peptides (I-J as described in Table 6) in CFA inflammatory pain model in rats (60 mg/kg, s.c., at day 3 or 4 after administration).

At the screening dose of 60 mg/kg, certain modified peptides produced an antinociceptive effect within three or four days following a single s.c. injection (FIG. 6). Observable effects of active modified peptides generally subsided between days five and six following the injection.

TABLE 6

In vivo antinociceptive activity of anti-NGF matured modified peptides in rat pain models

| Linker (L) Portion of (L)–(P) fusion (SEQ ID NO:) | Peptide (P) Portion of (L)–(P) fusion (SEQ ID NO:) | Attachment of (L)–(P) fusion to Fc domain* | In Vivo anti-NGF Activity of Matured Modified Peptide |
|---|---|---|---|
| 285 | 219 | C-term | FIG. 5, A |
| 285 | 251 | C-term | FIG. 5, B |
| 285 | 236 | C-term | FIG. 5, C |
| 285 | 233 | | FIG. 5, D |
| 285 | 246 | | FIG. 5, E |
| 285 | 208 | | FIG. 5, F |
| 285 | 224 | C-term | FIG. 5, G |
| 285 | 241 | C-term | FIG. 5, H |
| 285 | 239 | C-term | FIG. 6, I |
| 285 | 266 | | FIG. 6, J |

*(L)–(P) fusions were attached to the N-terminus of Fc domain (SEQ ID NO: 60 lacking N-terminal methionine) unless designated "C-term" wherein the (L)–(P) fusions were attached to the C-terminus of Fc domain (SEQ ID NO: 60).

What is claimed is:

1. A polynucleotide comprising a polynucleotide sequence encoding a composition of matter comprising at least one peptide selected from the group consisting of SEQ ID NOS:202, 211, 219, 221, 231, 237, and 272, inclusive, and a vehicle.

2. An expression vector comprising the polynucleotide of claim 1.

3. An isolated host cell comprising the expression vector of claim 2.

4. The host cell according to claim 3 wherein the cell is a prokaryotic cell.

5. The host cell according to claim 4 wherein the cell is an *E. coli* cell.

6. The host cell according to claim 3 wherein the cell is a eukaryotic cell.

7. A polynucleotide of claim 1 wherein said vehicle is a Fc domain.

* * * * *

SEQUENCE LISTING

<160> NUMBER OF SEQ ID NOS: 286

<210> SEQ ID NO 1
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 1

Thr Gly Tyr Thr Glu Tyr Thr Glu Glu Trp Pro Met Gly Phe Gly Tyr
1               5                   10                  15

Gln Trp Ser Phe
            20

<210> SEQ ID NO 2
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 2

Thr Asp Trp Leu Ser Asp Phe Pro Phe Tyr Glu Gln Tyr Phe Gly Leu
1               5                   10                  15

Met Pro Pro Gly
            20

<210> SEQ ID NO 3
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 3

Phe Met Arg Phe Pro Asn Pro Trp Lys Leu Val Glu Pro Pro Gln Gly
1               5                   10                  15

Trp Tyr Tyr Gly
            20

<210> SEQ ID NO 4
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 4

Val Val Lys Ala Pro His Phe Glu Phe Leu Ala Pro Pro His Phe His
1               5                   10                  15

Glu Phe Pro Phe
            20

<210> SEQ ID NO 5
<211> LENGTH: 20
<212> TYPE: PRT
<213> ORGANISM: Artificial Sequence
<220> FEATURE:
<223> OTHER INFORMATION: Therapeutically active peptide of randomly generated, non-naturally occurring sequence

<400> SEQUENCE: 5

Phe Ser Tyr Ile Trp Ile Asp Glu Thr Pro Ser Asn Ile Asp Arg Tyr
1               5                   10                  15

Met Leu Trp Leu
            20

<210> SEQ ID NO 6
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 6

Val Asn Phe Pro Lys Val Pro Glu Asp Val Glu Pro Trp Pro Trp Ser
1               5                   10                  15

Leu Lys Leu Tyr
            20

<210> SEQ ID NO 7
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 7

Thr Trp His Pro Lys Thr Tyr Glu Glu Phe Ala Leu Pro Phe Phe Val
1               5                   10                  15

Pro Glu Ala Pro
            20

<210> SEQ ID NO 8
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 8

Trp His Phe Gly Thr Pro Tyr Ile Gln Gln Gln Pro Gly Val Tyr Trp
1               5                   10                  15

Leu Gln Ala Pro
            20

<210> SEQ ID NO 9
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 9

Val Trp Asn Tyr Gly Pro Phe Phe Met Asn Phe Pro Asp Ser Thr Tyr
1               5                   10                  15

Phe Leu His Glu
            20

```
<210> SEQ ID NO 10
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 10

Trp Arg Ile His Ser Lys Pro Leu Asp Tyr Ser His Val Trp Phe Phe
1               5                   10                  15

Pro Ala Asp Phe
            20

<210> SEQ ID NO 11
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 11

Phe Trp Asp Gly Asn Gln Pro Pro Asp Ile Leu Val Asp Trp Pro Trp
1               5                   10                  15

Asn Pro Pro Val
            20

<210> SEQ ID NO 12
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 12

Phe Tyr Ser Leu Glu Trp Leu Lys Asp His Ser Glu Phe Phe Gln Thr
1               5                   10                  15

Val Thr Glu Trp
            20

<210> SEQ ID NO 13
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 13

Gln Phe Met Glu Leu Leu Lys Phe Phe Asn Ser Pro Gly Asp Ser Ser
1               5                   10                  15

His His Phe Leu
            20

<210> SEQ ID NO 14
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 14

Thr Asn Val Asp Trp Ile Ser Asn Trp Glu His Met Lys Ser Phe
```

```
1               5                  10                 15

Phe Thr Glu Asp
            20

<210> SEQ ID NO 15
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 15

Pro Asn Glu Lys Pro Tyr Gln Met Gln Ser Trp Phe Pro Pro Asp Trp
1               5                   10                  15

Pro Val Pro Tyr
            20

<210> SEQ ID NO 16
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 16

Trp Ser His Thr Glu Trp Val Pro Gln Val Trp Trp Lys Pro Pro Asn
1               5                   10                  15

His Phe Tyr Val
            20

<210> SEQ ID NO 17
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 17

Trp Gly Glu Trp Ile Asn Asp Ala Gln Val His Met His Glu Gly Phe
1               5                   10                  15

Ile Ser Glu Ser
            20

<210> SEQ ID NO 18
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 18

Val Pro Trp Glu His Asp His Asp Leu Trp Glu Ile Ile Ser Gln Asp
1               5                   10                  15

Trp His Ile Ala
            20

<210> SEQ ID NO 19
<211> LENGTH: 20
<212> TYPE: PRT
<213> ORGANISM: Artificial Sequence
<220> FEATURE:
```

-continued

<223> OTHER INFORMATION: Therapeutically active peptide of randomly
      generated, non-naturally occurring sequence

<400> SEQUENCE: 19

Val Leu His Leu Gln Asp Pro Arg Gly Trp Ser Asn Phe Pro Pro Gly
1               5                   10                  15

Val Leu Glu Leu
            20

<210> SEQ ID NO 20
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 20

Ile His Gly Cys Trp Phe Thr Glu Glu Gly Cys Val Trp Gln
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 21

Tyr Met Gln Cys Gln Phe Ala Arg Asp Gly Cys Pro Gln Trp
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 22

Lys Leu Gln Cys Gln Tyr Ser Glu Ser Gly Cys Pro Thr Ile
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 23

Phe Leu Gln Cys Glu Ile Ser Gly Gly Ala Cys Pro Ala Pro
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 24

Lys Leu Gln Cys Glu Phe Ser Thr Ser Gly Cys Pro Asp Leu

<210> SEQ ID NO 25
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 25

Lys Leu Gln Cys Glu Phe Ser Thr Gln Gly Cys Pro Asp Leu
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 26

Lys Leu Gln Cys Glu Phe Ser Thr Ser Gly Cys Pro Trp Leu
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 27

Ile Gln Gly Cys Trp Phe Thr Glu Glu Gly Cys Pro Trp Gln
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 28

Ser Phe Asp Cys Asp Asn Pro Trp Gly His Val Leu Gln Ser Cys Phe
1               5                   10                  15

Gly Phe

<210> SEQ ID NO 29
<211> LENGTH: 18
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 29

Ser Phe Asp Cys Asp Asn Pro Trp Gly His Lys Leu Gln Ser Cys Phe
1               5                   10                  15

Gly Phe

<210> SEQ ID NO 30
<211> LENGTH: 21

```
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 30

Met Thr Gly Tyr Thr Glu Tyr Thr Glu Glu Trp Pro Met Gly Phe Gly
1               5                   10                  15

Tyr Gln Trp Ser Phe
            20

<210> SEQ ID NO 31
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 31

Met Thr Asp Trp Leu Ser Asp Phe Pro Phe Tyr Glu Gln Tyr Phe Gly
1               5                   10                  15

Leu Met Pro Pro Gly
            20

<210> SEQ ID NO 32
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 32

Met Phe Met Arg Phe Pro Asn Pro Trp Lys Leu Val Glu Pro Pro Gln
1               5                   10                  15

Gly Trp Tyr Tyr Gly
            20

<210> SEQ ID NO 33
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 33

Met Val Val Lys Ala Pro His Phe Glu Phe Leu Ala Pro Pro His Phe
1               5                   10                  15

His Glu Phe Pro Phe
            20

<210> SEQ ID NO 34
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 34

Met Phe Ser Tyr Ile Trp Ile Asp Glu Thr Pro Ser Asn Ile Asp Arg
1               5                   10                  15
```

```
Tyr Met Leu Trp Leu
            20

<210> SEQ ID NO 35
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 35

Met Val Asn Phe Pro Lys Val Pro Glu Asp Val Glu Pro Trp Pro Trp
1               5                   10                  15

Ser Leu Lys Leu Tyr
            20

<210> SEQ ID NO 36
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 36

Met Thr Trp His Pro Lys Thr Tyr Glu Glu Phe Ala Leu Pro Phe Phe
1               5                   10                  15

Val Pro Glu Ala Pro
            20

<210> SEQ ID NO 37
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 37

Met Trp His Phe Gly Thr Pro Tyr Ile Gln Gln Gln Pro Gly Val Tyr
1               5                   10                  15

Trp Leu Gln Ala Pro
            20

<210> SEQ ID NO 38
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 38

Met Val Trp Asn Tyr Gly Pro Phe Phe Met Asn Phe Pro Asp Ser Thr
1               5                   10                  15

Tyr Phe Leu His Glu
            20

<210> SEQ ID NO 39
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence
```

-continued

```
<400> SEQUENCE: 39

Met Trp Arg Ile His Ser Lys Pro Leu Asp Tyr Ser His Val Trp Phe
1               5                   10                  15

Phe Pro Ala Asp Phe
            20

<210> SEQ ID NO 40
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 40

Met Phe Trp Asp Gly Asn Gln Pro Pro Asp Ile Leu Val Asp Trp Pro
1               5                   10                  15

Trp Asn Pro Pro Val
            20

<210> SEQ ID NO 41
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 41

Met Phe Tyr Ser Leu Glu Trp Leu Lys Asp His Ser Glu Phe Phe Gln
1               5                   10                  15

Thr Val Thr Glu Trp
            20

<210> SEQ ID NO 42
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 42

Met Gln Phe Met Glu Leu Leu Lys Phe Phe Asn Ser Pro Gly Asp Ser
1               5                   10                  15

Ser His His Phe Leu
            20

<210> SEQ ID NO 43
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 43

Met Thr Asn Val Asp Trp Ile Ser Asn Asn Trp Glu His Met Lys Ser
1               5                   10                  15

Phe Phe Thr Glu Asp
            20

<210> SEQ ID NO 44
```

```
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 44

Met Pro Asn Glu Lys Pro Tyr Gln Met Gln Ser Trp Phe Pro Pro Asp
1               5                   10                  15

Trp Pro Val Pro Tyr
            20

<210> SEQ ID NO 45
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 45

Met Trp Ser His Thr Glu Trp Val Pro Gln Val Trp Trp Lys Pro Pro
1               5                   10                  15

Asn His Phe Tyr Val
            20

<210> SEQ ID NO 46
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 46

Met Trp Gly Glu Trp Ile Asn Asp Ala Gln Val His Met His Glu Gly
1               5                   10                  15

Phe Ile Ser Glu Ser
            20

<210> SEQ ID NO 47
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 47

Met Val Pro Trp Glu His Asp His Asp Leu Trp Glu Ile Ile Ser Gln
1               5                   10                  15

Asp Trp His Ile Ala
            20

<210> SEQ ID NO 48
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 48

Met Val Leu His Leu Gln Asp Pro Arg Gly Trp Ser Asn Phe Pro Pro
1               5                   10                  15
```

```
Gly Val Leu Glu Leu
         20

<210> SEQ ID NO 49
<211> LENGTH: 15
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 49

Met Ile His Gly Cys Trp Phe Thr Glu Glu Gly Cys Val Trp Gln
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 50

Met Tyr Met Gln Cys Gln Phe Ala Arg Asp Gly Cys Pro Gln Trp
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 51

Met Lys Leu Gln Cys Gln Tyr Ser Glu Ser Gly Cys Pro Thr Ile
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 52

Met Phe Leu Gln Cys Glu Ile Ser Gly Gly Ala Cys Pro Ala Pro
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 53

Met Lys Leu Gln Cys Glu Phe Ser Thr Ser Gly Cys Pro Asp Leu
1               5                   10                  15

<210> SEQ ID NO 54
<211> LENGTH: 15
<212> TYPE: PRT
<213> ORGANISM: Artificial Sequence
```

```
<220> FEATURE:
<223> OTHER INFORMATION: Therapeutically active peptide of randomly
      generated, non-naturally occurring sequence

<400> SEQUENCE: 54

Met Lys Leu Gln Cys Glu Phe Ser Thr Gln Gly Cys Pro Asp Leu
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 55

Met Lys Leu Gln Cys Glu Phe Ser Thr Ser Gly Cys Pro Trp Leu
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 56

Met Ile Gln Gly Cys Trp Phe Thr Glu Glu Gly Cys Pro Trp Gln
1               5                   10                  15

<210> SEQ ID NO 57
<211> LENGTH: 19
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 57

Met Ser Phe Asp Cys Asp Asn Pro Trp Gly His Val Leu Gln Ser Cys
1               5                   10                  15

Phe Gly Phe

<210> SEQ ID NO 58
<211> LENGTH: 19
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 58

Met Ser Phe Asp Cys Asp Asn Pro Trp Gly His Lys Leu Gln Ser Cys
1               5                   10                  15

Phe Gly Phe

<210> SEQ ID NO 59
<211> LENGTH: 684
<212> TYPE: DNA
<213> ORGANISM: Homo sapiens

<400> SEQUENCE: 59
atggacaaaa ctcacacatg tccaccttgt ccagctccgg aactcctggg gggaccgtca      60
```

-continued

```
gtcttcctct tccccccaaa acccaaggac accctcatga tctcccggac ccctgaggtc      120
acatgcgtgg tggtggacgt gagccacgaa gaccctgagg tcaagttcaa ctggtacgtg      180
gacggcgtgg aggtgcataa tgccaagaca agccgcggg aggagcagta caacagcacg       240
taccgtgtgg tcagcgtcct caccgtcctg caccaggact ggctgaatgg caaggagtac      300
aagtgcaagg tctccaacaa agccctccca gcccccatcg agaaaaccat ctccaaagcc      360
aaagggcagc cccgagaacc acaggtgtac accctgcccc catcccggga tgagctgacc      420
aagaaccagg tcagcctgac ctgcctggtc aaaggcttct atcccagcga catcgccgtg      480
gagtgggaga gcaatgggca gccggagaac aactacaaga ccacgcctcc cgtgctggac      540
tccgacggct ccttcttcct ctacagcaag ctcaccgtgg acaagagcag gtggcagcag      600
gggaacgtct tctcatgctc cgtgatgcat gaggctctgc acaaccacta cacgcagaag      660
agcctctccc tgtctccggg taaa                                             684
```

<210> SEQ ID NO 60
<211> LENGTH: 228
<212> TYPE: PRT
<213> ORGANISM: Homo sapiens

<400> SEQUENCE: 60

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 61
<211> LENGTH: 779
<212> TYPE: DNA

<213> ORGANISM: Artificial Sequence
<220> FEATURE:
<223> OTHER INFORMATION: Expression vector component

<400> SEQUENCE: 61

```
tctagatttg ttttaactaa ttaaaggagg aataacatat gggtgcacag aaagcggccg      60
caaaaaaact cgagggtgga ggcggtgggg acaaaactca cacatgtcca ccttgcccag     120
cacctgaact cctgggggga ccgtcagttt tcctcttccc cccaaaaccc aaggacaccc     180
tcatgatctc ccggacccct gaggtcacat gcgtggtggt ggacgtgagc cacgaagacc     240
ctgaggtcaa gttcaactgg tacgtggacg gcgtggaggt gcataatgcc aagacaaagc     300
cgcgggagga gcagtacaac agcacgtacc gtgtggtcag cgtcctcacc gtcctgcaca     360
ggactggctg aatggcaagg agtacaagtg caaggtctcc aacaaagccc tcccagcccc     420
catcgagaaa accatctcca aagccaaagg gcagccccga gaaccacagg tgtacaccct     480
gcccccatcc cggatgagc tgaccaagaa ccaggtcagc ctgacctgcc tggtcaaagg     540
cttctatccc agcgacatcg ccgtggagtg ggagagcaat gggcagccgg agaacaacta     600
caagaccacg cctcccgtgc tggactccga cggctccttc ttcctctaca gcaagctcac     660
cgtggacaag agcaggtggc agcaggggaa cgtcttctca tgctccgtga tgcatgaggc     720
tctgcacaac cactacacgc agaagagcct ctccctgtct ccgggtaaat aatggatcc     779
```

<210> SEQ ID NO 62
<211> LENGTH: 780
<212> TYPE: DNA
<213> ORGANISM: Artificial Sequence
<220> FEATURE:
<223> OTHER INFORMATION: Expression vector component

<400> SEQUENCE: 62

```
agatctaaac aaaattgatt aatttcctcc ttattgtata cccacgtgtc tttcgccggc      60
gttttttga gctcccacct ccgccacccc tgttttgagt gtgtacaggt ggaacgggtc     120
gtggacttga ggaccccct ggcagtcaaa aggagaaggg gggttttggg ttcctgtggg     180
agtactagag ggcctgggga ctccagtgta cgcaccacca cctgcactcg gtgcttctgg     240
gactccagtt caagttgacc atgcacctgc cgcacctcca cgtattacgg ttctgtttcg     300
gcgccctcct cgtcatgttg tcgtgcatgg cacaccagtc gcaggagtgg caggacgtgg     360
tcctgaccga cttaccgttc ctcatgttca cgttccagag gttgtttcgg gagggtcggg     420
ggtagctctt ttggtagagg tttcggtttc ccgtcggggc tcttggtgtc cacatgtggg     480
acggggtag ggccctactc gactggttct tggtccagtc ggactggacg gaccagtttc     540
cgaagatagg gtcgctgtag cggcacctca ccctctcgtt accgtcggc ctcttgttga     600
tgttctggtg cggagggcac gacctgaggc tgccgaggaa gaaggagatg tcgttcgagt     660
ggcacctgtt ctcgtccacc gtcgtcccct tgcagaagag tacgaggcac tacgtactcc     720
gagacgtgtt ggtgatgtgc gtcttctcgg agagggacag aggcccattt attacctagg     780
```

<210> SEQ ID NO 63
<211> LENGTH: 57
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 63

```
atgattcatg gttgttggtt tacagaagaa ggttgtgttt ggcaactcga gggtgga        57
```

<210> SEQ ID NO 64
<211> LENGTH: 57
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 64

```
atgtatatgc aatgtcaatt tgctcgtgat ggttgtccac aatggctcga gggtgga        57
```

<210> SEQ ID NO 65
<211> LENGTH: 57
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 65

```
atgaaattac aatgtcaata ttctgaatct ggttgtccaa caattctcga gggtgga        57
```

<210> SEQ ID NO 66
<211> LENGTH: 57
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 66

```
atgttttac aatgtgaaat ttctggtggt gcttgtccag ctccactcga gggtgga         57
```

<210> SEQ ID NO 67
<211> LENGTH: 57
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 67

```
atgaaattac aatgtgaatt ttctacttct ggttgtccag atttactcga gggtgga        57
```

<210> SEQ ID NO 68
<211> LENGTH: 57
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 68

```
atgaaattac aatgtgaatt ttctactcaa ggttgtccag atttactcga gggtgga        57
```

<210> SEQ ID NO 69
<211> LENGTH: 57
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 69

```
atgaaattac aatgtgaatt ttctacttct ggttgtcctt ggttactcga gggtgga        57
```

```
<210> SEQ ID NO 70
<211> LENGTH: 57
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 70
atgattcaag ttgttggtt tactgaagaa ggttgtcctt ggcaactcga gggtgga        57

<210> SEQ ID NO 71
<211> LENGTH: 69
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 71
atgtcttttg attgtgataa tccttggggt catgttttac aatcttgttt tggttttctc    60
gagggtgga                                                            69

<210> SEQ ID NO 72
<211> LENGTH: 69
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 72
atgtcttttg attgtgataa tccttggggt cataaattac aatcttgttt tggttttctc    60
gagggtgga                                                            69

<210> SEQ ID NO 73
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 73
atgacaggtt atacagaata tacagaagaa tggccaatgg ttttggtta tcaatggtcc     60 tttctcgagg gtgga                                                     75

<210> SEQ ID NO 74
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 74
atgacagatt ggttatctga ttttccattc tatgaacaat actttggttt aatgccacct    60
ggtctcgagg gtgga                                                     75

<210> SEQ ID NO 75
<211> LENGTH: 75
<212> TYPE: DNA
<213> ORGANISM: Artificial Sequence
```

```
<220> FEATURE:
<223> OTHER INFORMATION: Encodes for therapeutically active peptides
      with methionine residue at N-terminus

<400> SEQUENCE: 75
atgtttatgc gttttcctaa cccatggaaa ttagttgaac cacctcaagg ttggtactat    60
ggtctcgagg gtgga                                                    75

<210> SEQ ID NO 76
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 76
atggttgtta aagctccaca ttttgaattc ttagctccac ctcattttca tgaatttcca    60
tttctcgagg gtgga                                                    75

<210> SEQ ID NO 77
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 77
atgttttctt atatttggat tgatgaaact ccgtctaaca ttgatcgtta tatgctgtgg    60
ctgctcgagg gtgga                                                    75

<210> SEQ ID NO 78
<211> LENGTH: 74
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 78
tggttaactt tccgaaagtt ccggaagatg ttgaaccgtg gccgtggtct ctgaaactgt    60
atctcgaggg tgga                                                     74

<210> SEQ ID NO 79
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 79
atgacttggc acccgaaaac ttatgaagaa tttgctctgc cgttttttgt tccggaagct    60
ccgctcgagg gtgga                                                    75

<210> SEQ ID NO 80
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus
```

```
<400> SEQUENCE: 80
atgtggcatt ttggtactcc atatattcaa caacaaccag gtgtttattg gttacaagct     60
ccactcgagg gtgga                                                      75

<210> SEQ ID NO 81
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 81
atggtttgga attatggtcc attttttatg aattttccag attctactta ttttttacat     60
gaactcgagg gtgga                                                      75

<210> SEQ ID NO 82
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 82
atgtggcgta ttcattctaa accattagat tattctcatg tttggttttt ccagctgat      60 tttctcgagg gtgga                                                      75

<210> SEQ ID NO 83
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 83
atgttttggg atggtaatca accaccagat attttagttg attggccatg gaatccacca     60
gttctcgagg gtgga                                                      75

<210> SEQ ID NO 84
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 84 atgtttatt ctttagaatg gttaaaagat cattctgaat tttttcaaac tgttactgaa      60
tggctcgagg gtgga                                                      75

<210> SEQ ID NO 85
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 85
atgcaattta tggaattact gaaattcttt aattctccag gtgattcttc tcatcacttc     60
```

-continued ttactcgagg gtgga                                                    75

<210> SEQ ID NO 86
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 86
atgactaatg ttgattggat ttctaataat tgggaacata tgaaatcttt ttttactgaa    60
gatctcgagg gtgga                                                    75

<210> SEQ ID NO 87
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 87
atgccaaatg aaaaaccata tcaaatgcaa tcttggtttc caccagattg gccagttcca    60
tatctcgagg gtgga                                                    75

<210> SEQ ID NO 88
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 88
atgtggtctc atactgaatg ggttccacaa gtttggtgga aaccaccaaa tcatttttat    60
gttctcgagg gtgga                                                    75

<210> SEQ ID NO 89
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 89 atgtgggtg aatggattaa tgatgctcaa gttcacatgc atgaaggttt tatttctgaa    60
tctctcgagg gtgga                                                    75

<210> SEQ ID NO 90
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 90
atggttccat gggaacatga tcatgattta tgggaaatta tttctcaaga ttggcatatt    60
gctctcgagg gtgga                                                    75

<210> SEQ ID NO 91

```
<211> LENGTH: 75
<212> TYPE: DNA
<213> ORGANISM: Artificial Sequence
<220> FEATURE:
<223> OTHER INFORMATION: Encodes for therapeutically active peptides
      with methionine residue at N-terminus

<400> SEQUENCE: 91
atggttttac atttacaaga tccacgtggt tggtctaatt ttccaccagg tgttttagaa      60
ttactcgagg gtgga                                                      75

<210> SEQ ID NO 92
<211> LENGTH: 19
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 92

Met Ile His Gly Cys Trp Phe Thr Glu Glu Gly Cys Val Trp Gln Leu
1               5                   10                  15

Glu Gly Gly

<210> SEQ ID NO 93
<211> LENGTH: 19
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 93

Met Tyr Met Gln Cys Gln Phe Ala Arg Asp Gly Cys Pro Gln Trp Leu
1               5                   10                  15

Glu Gly Gly

<210> SEQ ID NO 94
<211> LENGTH: 19
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 94

Met Lys Leu Gln Cys Gln Tyr Ser Glu Ser Gly Cys Pro Thr Ile Leu
1               5                   10                  15

Glu Gly Gly

<210> SEQ ID NO 95
<211> LENGTH: 19
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 95

Met Phe Leu Gln Cys Glu Ile Ser Gly Gly Ala Cys Pro Ala Pro Leu
1               5                   10                  15

Glu Gly Gly

<210> SEQ ID NO 96
```

<211> LENGTH: 19
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 96

Met Lys Leu Gln Cys Glu Phe Ser Thr Ser Gly Cys Pro Asp Leu Leu
1               5                   10                  15

Glu Gly Gly

<210> SEQ ID NO 97
<211> LENGTH: 19
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 97

Met Lys Leu Gln Cys Glu Phe Ser Thr Gln Gly Cys Pro Asp Leu Leu
1               5                   10                  15

Glu Gly Gly

<210> SEQ ID NO 98
<211> LENGTH: 19
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 98

Met Lys Leu Gln Cys Glu Phe Ser Thr Ser Gly Cys Pro Trp Leu Leu
1               5                   10                  15

Glu Gly Gly

<210> SEQ ID NO 99
<211> LENGTH: 19
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 99

Met Ile Gln Gly Cys Trp Phe Thr Glu Glu Gly Cys Pro Trp Gln Leu
1               5                   10                  15

Glu Gly Gly

<210> SEQ ID NO 100
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 100

Met Ser Phe Asp Cys Asp Asn Pro Trp Gly His Val Leu Gln Ser Cys
1               5                   10                  15

Phe Gly Phe Leu Glu Gly Gly
                20

```
<210> SEQ ID NO 101
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 101

Met Ser Phe Asp Cys Asp Asn Pro Trp Gly His Lys Leu Gln Ser Cys
1               5                   10                  15

Phe Gly Phe Leu Glu Gly Gly
            20

<210> SEQ ID NO 102
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 102

Met Thr Gly Tyr Thr Glu Tyr Thr Glu Glu Trp Pro Met Gly Phe Gly
1               5                   10                  15

Tyr Gln Trp Ser Phe Leu Glu Gly Gly
            20                  25

<210> SEQ ID NO 103
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 103

Met Thr Asp Trp Leu Ser Asp Phe Pro Phe Tyr Glu Gln Tyr Phe Gly
1               5                   10                  15

Leu Met Pro Pro Gly Leu Glu Gly Gly Gly
            20                  25

<210> SEQ ID NO 104
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 104

Met Phe Met Arg Phe Pro Asn Pro Trp Lys Leu Val Glu Pro Pro Gln
1               5                   10                  15

Gly Trp Tyr Tyr Gly Leu Glu Gly Gly
            20                  25

<210> SEQ ID NO 105
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 105
```

```
Met Val Val Lys Ala Pro His Phe Glu Phe Leu Ala Pro Pro His Phe
1               5                   10                  15

His Glu Phe Pro Phe Leu Glu Gly Gly
                20                  25
```

<210> SEQ ID NO 106
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 106

```
Met Phe Ser Tyr Ile Trp Ile Asp Glu Thr Pro Ser Asn Ile Asp Arg
1               5                   10                  15

Tyr Met Leu Trp Leu Leu Glu Gly Gly
                20                  25
```

<210> SEQ ID NO 107
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 107

```
Met Val Asn Phe Pro Lys Val Pro Glu Asp Val Glu Pro Trp Pro Trp
1               5                   10                  15

Ser Leu Lys Leu Tyr Leu Glu Gly Gly Gly
                20                  25
```

<210> SEQ ID NO 108
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 108

```
Met Thr Trp His Pro Lys Thr Tyr Glu Glu Phe Ala Leu Pro Phe Phe
1               5                   10                  15

Val Pro Glu Ala Pro Leu Glu Gly Gly
                20                  25
```

<210> SEQ ID NO 109
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 109

```
Met Trp His Phe Gly Thr Pro Tyr Ile Gln Gln Gln Pro Gly Val Tyr
1               5                   10                  15

Trp Leu Gln Ala Pro Leu Glu Gly Gly
                20                  25
```

<210> SEQ ID NO 110
<211> LENGTH: 25
<212> TYPE: PRT
<213> ORGANISM: Artificial Sequence

```
<220> FEATURE:
<223> OTHER INFORMATION: Therapeutically active peptide of randomly
      generated, non-naturally occurring sequence

<400> SEQUENCE: 110

Met Val Trp Asn Tyr Gly Pro Phe Phe Met Asn Phe Pro Asp Ser Thr
1               5                   10                  15

Tyr Phe Leu His Glu Leu Glu Gly Gly
            20                  25

<210> SEQ ID NO 111
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 111

Met Trp Arg Ile His Ser Lys Pro Leu Asp Tyr Ser His Val Trp Phe
1               5                   10                  15

Phe Pro Ala Asp Phe Leu Glu Gly Gly
            20                  25

<210> SEQ ID NO 112
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 112

Met Phe Trp Asp Gly Asn Gln Pro Pro Asp Ile Leu Val Asp Trp Pro
1               5                   10                  15

Trp Asn Pro Pro Val Leu Glu Gly Gly
            20                  25

<210> SEQ ID NO 113
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 113

Met Phe Tyr Ser Leu Glu Trp Leu Lys Asp His Ser Glu Phe Phe Gln
1               5                   10                  15

Thr Val Thr Glu Trp Leu Glu Gly Gly
            20                  25

<210> SEQ ID NO 114
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 114

Met Gln Phe Met Glu Leu Leu Lys Phe Phe Asn Ser Pro Gly Asp Ser
1               5                   10                  15

Ser His His Phe Leu Leu Glu Gly Gly
            20                  25
```

<210> SEQ ID NO 115
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 115

His Met Thr Asn Val Asp Trp Ile Ser Asn Asn Trp Glu His Met Lys
1               5                   10                  15

Ser Phe Phe Thr Glu Asp Leu Glu Gly Gly
            20                  25

<210> SEQ ID NO 116
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 116

Met Pro Asn Glu Lys Pro Tyr Gln Met Gln Ser Trp Phe Pro Pro Asp
1               5                   10                  15

Trp Pro Val Pro Tyr Leu Glu Gly Gly
            20                  25

<210> SEQ ID NO 117
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 117

Met Trp Ser His Thr Glu Trp Val Pro Gln Val Trp Trp Lys Pro Pro
1               5                   10                  15

Asn His Phe Tyr Val Leu Glu Gly Gly
            20                  25

<210> SEQ ID NO 118
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 118

Met Trp Gly Glu Trp Ile Asn Asp Ala Gln Val His Met His Glu Gly
1               5                   10                  15

Phe Ile Ser Glu Ser Leu Glu Gly Gly
            20                  25

<210> SEQ ID NO 119
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 119

```
Met Val Pro Trp Glu His Asp His Asp Leu Trp Glu Ile Ile Ser Gln
1               5                   10                  15

Asp Trp His Ile Ala Leu Glu Gly Gly
            20                  25
```

<210> SEQ ID NO 120
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 120

```
Met Val Leu His Leu Gln Asp Pro Arg Gly Trp Ser Asn Phe Pro Pro
1               5                   10                  15

Gly Val Leu Glu Leu Leu Glu Gly Gly
            20                  25
```

<210> SEQ ID NO 121
<211> LENGTH: 777
<212> TYPE: DNA
<213> ORGANISM: Artificial Sequence
<220> FEATURE:
<223> OTHER INFORMATION: Expression vector

<400> SEQUENCE: 121

```
tctagatttg ttttaactaa ttaaaggagg aataacatat ggacaaaact cacacatgtc    60
caccttgtcc agctccggaa ctcctggggg accgtcagt cttcctcttc cccccaaaac   120
ccaaggacac cctcatgatc tcccggaccc ctgaggtcac atgcgtggtg gtggacgtga   180
gccacgaaga ccctgaggtc aagttcaact ggtacgtgga cggcgtggag gtgcataatg   240
ccaagacaaa gccgcgggag gagcagtaca acagcacgta ccgtgtggtc agcgtcctca   300
ccgtcctgca ccaggactgg ctgaatggca aggagtacaa gtgcaaggtc tccaacaaag   360
ccctcccagc ccccatcgag aaaaccatct ccaaagccaa agggcagccc cgagaaccac   420
aggtgtacac cctgccccca tcccgggatg agctgaccaa gaaccaggtc agcctgacct   480
gcctggtcaa aggcttctat cccagcgaca tcgccgtgga gtgggagagc aatgggcagc   540
cggagaacaa ctacaagacc acgcctcccg tgctggactc cgacggctcc ttcttcctct   600
acagcaagct caccgtggac aagagcaggt ggcagcaggg gaacgtcttc tcatgctccg   660
tgatgcatga ggctctgcac aaccactaca cgcagaagag cctctccctg tctccgggta   720
aaggtggagg tggtggtgca cagaaagcgg ccgcaaaaaa actcgagtaa tggatcc      777
```

<210> SEQ ID NO 122
<211> LENGTH: 777
<212> TYPE: DNA
<213> ORGANISM: Artificial Sequence
<220> FEATURE:
<223> OTHER INFORMATION: Expression vector

<400> SEQUENCE: 122

```
agatctaaac aaaattgatt aatttcctcc ttattgtata cctgttttga gtgtgtacag    60
gtggaacagg tcgaggcctt gaggaccccc ctggcagtca gaaggagaag ggggttttg   120
ggttcctgtg ggagtactag agggcctggg gactccagtg tacgcaccac cacctgcact   180
cggtgcttct gggactccag ttcaagttga ccatgcacct gccgcacctc acgtattac    240
ggttctgttt cggcgccctc ctcgtcatgt tgtcgtgcat ggcacaccag tcgcaggagt   300
```

```
ggcaggacgt ggtcctgacc gacttaccgt tcctcatgtt cacgttccag aggttgtttc     360
gggagggtcg ggggtagctc ttttggtaga ggtttcggtt tcccgtcggg gctcttggtg     420
tccacatgtg ggacgggggt agggccctac tcgactggtt cttggtccag tcggactgga     480
cggaccagtt tccgaagata gggtcgctgt agcggcacct caccctctcg ttacccgtcg     540
gcctcttgtt gatgttctgg tgcggagggc acgacctgag gctgccgagg aagaaggaga     600
tgtcgttcga gtggcacctg ttctcgtcca ccgtcgtccc cttgcagaag agtacgaggc     660
actacgtact ccgagacgtg ttggtgatgt gcgtcttctc ggagagggac agaggcccat     720
ttccacctcc accaccacgt gtctttcgcc ggcgtttttt tgagctcatt acctagg       777
```

<210> SEQ ID NO 123
<211> LENGTH: 8
<212> TYPE: PRT
<213> ORGANISM: Artificial Sequence
<220> FEATURE:
<223> OTHER INFORMATION: Linker for peptide-FC linkage

<400> SEQUENCE: 123

Gly Gly Gly Lys Gly Gly Gly Gly
1               5

<210> SEQ ID NO 124
<211> LENGTH: 8
<212> TYPE: PRT
<213> ORGANISM: Artificial Sequence
<220> FEATURE:
<223> OTHER INFORMATION: Linker for peptide-FC linkage

<400> SEQUENCE: 124

Gly Gly Gly Asn Gly Ser Gly Gly
1               5

<210> SEQ ID NO 125
<211> LENGTH: 8
<212> TYPE: PRT
<213> ORGANISM: Artificial Sequence
<220> FEATURE:
<223> OTHER INFORMATION: Linker for peptide-FC linkage

<400> SEQUENCE: 125

Gly Gly Gly Cys Gly Gly Gly Gly
1               5

<210> SEQ ID NO 126
<211> LENGTH: 5
<212> TYPE: PRT
<213> ORGANISM: Artificial Sequence
<220> FEATURE:
<223> OTHER INFORMATION: Linker for peptide-FC linkage

<400> SEQUENCE: 126

Gly Pro Asn Gly Gly
1               5

<210> SEQ ID NO 127
<211> LENGTH: 25
<212> TYPE: DNA
<213> ORGANISM: Artificial Sequence
<220> FEATURE:
<223> OTHER INFORMATION: Oligonucleotide primer for PCR

<400> SEQUENCE: 127
cggcgcaact atcggtatca agctg                                              25

<210> SEQ ID NO 128
<211> LENGTH: 26
<212> TYPE: DNA
<213> ORGANISM: Artificial Sequence
<220> FEATURE:
<223> OTHER INFORMATION: Oligonucleotide primer for PCR

<400> SEQUENCE: 128
catgtaccgt aacactgagt ttcgtc                                             26

<210> SEQ ID NO 129
<211> LENGTH: 47
<212> TYPE: DNA
<213> ORGANISM: Artificial Sequence
<220> FEATURE:
<223> OTHER INFORMATION: Oligonucleotide used in peptide construction

<400> SEQUENCE: 129
tatgattcat ggttgttggt ttacagaaga aggttgtgtt tggcaac                      47

<210> SEQ ID NO 130
<211> LENGTH: 49
<212> TYPE: DNA
<213> ORGANISM: Artificial Sequence
<220> FEATURE:
<223> OTHER INFORMATION: Oligonucleotide used in peptide construction

<400> SEQUENCE: 130
tcgagttgcc aaacacaacc ttcttctgta aaccaacaac catgaatca                    49

<210> SEQ ID NO 131
<211> LENGTH: 47
<212> TYPE: DNA
<213> ORGANISM: Artificial Sequence
<220> FEATURE:
<223> OTHER INFORMATION: Oligonucleotide used in peptide construction

<400> SEQUENCE: 131
tatgtatatg caatgtcaat ttgctcgtga tggttgtcca caatggc                      47

<210> SEQ ID NO 132
<211> LENGTH: 49
<212> TYPE: DNA
<213> ORGANISM: Artificial Sequence
<220> FEATURE:
<223> OTHER INFORMATION: Oligonucleotide used in peptide construction

<400> SEQUENCE: 132
tcgagccatt gtggacaacc atcacgagca aattgacatt gcatataca                    49

<210> SEQ ID NO 133
<211> LENGTH: 47
<212> TYPE: DNA
<213> ORGANISM: Artificial Sequence
<220> FEATURE:
<223> OTHER INFORMATION: Oligonucleotide used in peptide construction

<400> SEQUENCE: 133
tatgaaatta caatgtcaat attctgaatc tggttgtcca acaattc                      47

<210> SEQ ID NO 134
<211> LENGTH: 49
<212> TYPE: DNA
<213> ORGANISM: Artificial Sequence
<220> FEATURE:
<223> OTHER INFORMATION: Oligonucleotide used in peptide construction

<400> SEQUENCE: 134
tcgagaattg ttggacaacc agattcagaa tattgacatt gtaatttca                49

<210> SEQ ID NO 135
<211> LENGTH: 47
<212> TYPE: DNA
<213> ORGANISM: Artificial Sequence
<220> FEATURE:
<223> OTHER INFORMATION: Oligonucleotide used in peptide construction

<400> SEQUENCE: 135 tatgtttta caatgtgaaa tttctggtgg tgcttgtcca gctccac                47

<210> SEQ ID NO 136
<211> LENGTH: 49
<212> TYPE: DNA
<213> ORGANISM: Artificial Sequence
<220> FEATURE:
<223> OTHER INFORMATION: Oligonucleotide used in peptide construction

<400> SEQUENCE: 136
tcgagtggag ctggacaagc accaccagaa atttcacatt gtaaaaaca                49

<210> SEQ ID NO 137
<211> LENGTH: 47
<212> TYPE: DNA
<213> ORGANISM: Artificial Sequence
<220> FEATURE:
<223> OTHER INFORMATION: Oligonucleotide used in peptide construction

<400> SEQUENCE: 137
tatgaaatta caatgtgaat tttctacttc tggttgtcca gatttac                47

<210> SEQ ID NO 138
<211> LENGTH: 49
<212> TYPE: DNA
<213> ORGANISM: Artificial Sequence
<220> FEATURE:
<223> OTHER INFORMATION: Oligonucleotide used in peptide construction

<400> SEQUENCE: 138
tcgagtaaat ctggacaacc agaagtagaa aattcacatt gtaatttca                49

<210> SEQ ID NO 139
<211> LENGTH: 47
<212> TYPE: DNA
<213> ORGANISM: Artificial Sequence
<220> FEATURE:
<223> OTHER INFORMATION: Oligonucleotide used in peptide construction

<400> SEQUENCE: 139
tatgaaatta caatgtgaat tttctactca aggttgtcca gatttac                47

<210> SEQ ID NO 140
<211> LENGTH: 49
<212> TYPE: DNA
<213> ORGANISM: Artificial Sequence
<220> FEATURE:
<223> OTHER INFORMATION: Oligonucleotide used in peptide construction

<400> SEQUENCE: 140
tcgagtaaat ctggacaacc ttgagtagaa aattcacatt gtaatttca                49

<210> SEQ ID NO 141
<211> LENGTH: 47
<212> TYPE: DNA
<213> ORGANISM: Artificial Sequence
<220> FEATURE:
<223> OTHER INFORMATION: Oligonucleotide used in peptide construction

<400> SEQUENCE: 141
tatgaaatta caatgtgaat tttctacttc tggttgtcct tggttac          47

<210> SEQ ID NO 142
<211> LENGTH: 49
<212> TYPE: DNA
<213> ORGANISM: Artificial Sequence
<220> FEATURE:
<223> OTHER INFORMATION: Oligonucleotide used in peptide construction

<400> SEQUENCE: 142
tcgagtaacc aaggacaacc agaagtagaa aattcacatt gtaatttca        49

<210> SEQ ID NO 143
<211> LENGTH: 47
<212> TYPE: DNA
<213> ORGANISM: Artificial Sequence
<220> FEATURE:
<223> OTHER INFORMATION: Oligonucleotide used in peptide construction

<400> SEQUENCE: 143
tatgattcaa ggttgttggt ttactgaaga aggttgtcct tggcaac          47

<210> SEQ ID NO 144
<211> LENGTH: 49
<212> TYPE: DNA
<213> ORGANISM: Artificial Sequence
<220> FEATURE:
<223> OTHER INFORMATION: Oligonucleotide used in peptide construction

<400> SEQUENCE: 144
tcgagttgcc aaggacaacc ttcttcagta aaccaacaac cttgaatca        49

<210> SEQ ID NO 145
<211> LENGTH: 59
<212> TYPE: DNA
<213> ORGANISM: Artificial Sequence
<220> FEATURE:
<223> OTHER INFORMATION: Oligonucleotide used in peptide construction

<400> SEQUENCE: 145
tatgtctttt gattgtgata atccttgggg tcatgtttta caatcttgtt ttggttttc     59

<210> SEQ ID NO 146
<211> LENGTH: 61
<212> TYPE: DNA
<213> ORGANISM: Artificial Sequence
<220> FEATURE:
<223> OTHER INFORMATION: Oligonucleotide used in peptide construction

<400> SEQUENCE: 146
tcgagaaaac caaaacaaga ttgtaaaaca tgaccccaag gattatcaca atcaaaagac    60
a                                                                   61

<210> SEQ ID NO 147
<211> LENGTH: 59
<212> TYPE: DNA
<213> ORGANISM: Artificial Sequence

```
<220> FEATURE:
<223> OTHER INFORMATION: Oligonucleotide used in peptide construction

<400> SEQUENCE: 147 tatgtcttt  gattgtgata  atccttgggg  tcataaatta  caatcttgtt  ttggttttc         59

<210> SEQ ID NO 148
<211> LENGTH: 61
<212> TYPE: DNA
<213> ORGANISM: Artificial Sequence
<220> FEATURE:
<223> OTHER INFORMATION: Oligonucleotide used in peptide construction

<400> SEQUENCE: 148
tcgagaaaac  caaaacaaga  ttgtaattta  tgaccccaag  gattatcaca  atcaaaagac        60
a                                                                           61

<210> SEQ ID NO 149
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 149
tatgacaggt  tatacagaat  atacagaaga  atggccaatg  ggttttggtt  atcaatggtc        60
ctttc                                                                       65

<210> SEQ ID NO 150
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 150
tcgagaaagg  accattgata  accaaaaccc  attggccatt  cttctgtata  ttctgtataa        60
cctgtca                                                                     67

<210> SEQ ID NO 151
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 151
tatgacagat  tggttatctg  attttccatt  ctatgaacaa  tactttggtt  taatgccacc        60
tggtc                                                                       65

<210> SEQ ID NO 152
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 152
tcgagaccag  gtggcattaa  accaaagtat  tgttcataga  atggaaaatc  agataaccaa        60
tctgtca                                                                     67

<210> SEQ ID NO 153
```

<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 153
tatgtttatg cgttttccta acccatggaa attagttgaa ccacctcaag gttggtacta    60
tggtc    65

<210> SEQ ID NO 154
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 154
tcgagaccat agtaccaacc ttgaggtggt tcaactaatt tccatgggtt aggaaaacgc    60
ataaaca    67

<210> SEQ ID NO 155
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 155
tatggttgtt aaagctccac attttgaatt cttagctcca cctcattttc atgaatttcc    60
atttc    65

<210> SEQ ID NO 156
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 156
tcgagaaatg gaaattcatg aaaatgaggt ggagctaaga attcaaaatg tggagcttta    60
acaacca    67

<210> SEQ ID NO 157
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 157
tatgttttct tatatttgga ttgatgaaac tccgtctaac attgatcgtt atatgctgtg    60
gctgc    65

<210> SEQ ID NO 158
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 158
tcgagcagcc acagcatata acgatcaatg ttagacggag tttcatcaat ccaaatataa    60

-continued

```
gaaaaca                                                              67

<210> SEQ ID NO 159
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 159
tatggttaac tttccgaaag ttccggaaga tgttgaaccg tggccgtggt ctctgaaact    60
gtatc                                                                65

<210> SEQ ID NO 160
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 160
tcgagataca gtttcagaga ccacggccac ggttcaacat cttccggaac tttcggaaag    60
ttaacca                                                              67

<210> SEQ ID NO 161
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 161
tatgacttgg cacccgaaaa cttatgaaga atttgctctg ccgttttttg ttccggaagc    60
tccgc                                                                65

<210> SEQ ID NO 162
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 162
tcgagcggag cttccggaac aaaaaacggc agagcaaatt cttcataagt tttcgggtgc    60
caagtca                                                              67

<210> SEQ ID NO 163
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 163
tatgtggcat tttggtactc catatattca acaacaacca ggtgtttatt ggttacaagc    60
tccac                                                                65

<210> SEQ ID NO 164
<211> LENGTH: 67
<212> TYPE: DNA
<213> ORGANISM: Artificial Sequence
<220> FEATURE:
```

-continued

<223> OTHER INFORMATION: Oligonucleotide used in peptide construction

<400> SEQUENCE: 164
tcgagtggag cttgtaacca ataaacacct ggttgttgtt gaatatatgg agtaccaaaa    60
tgccaca                                                              67

<210> SEQ ID NO 165
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 165
tatggtttgg aattatggtc catttttat gaattttcca gattctactt attttttaca     60
tgaac                                                                65

<210> SEQ ID NO 166
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 166
tcgagttcat gtaaaaaata agtagaatct ggaaaattca taaaaaatgg accataattc    60
caaacca                                                              67

<210> SEQ ID NO 167
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 167
tatgtggcgt attcattcta aaccattaga ttattctcat gtttggtttt ttccagctga    60
ttttc                                                                65

<210> SEQ ID NO 168
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 168
tcgagaaaat cagctggaaa aaaccaaaca tgagaataat ctaatggttt agaatgaata    60
cgccaca                                                              67

<210> SEQ ID NO 169
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 169
tatgttttgg gatggtaatc aaccaccaga tattttagtt gattggccat ggaatccacc    60
agttc                                                                65

<210> SEQ ID NO 170
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 170
tcgagaactg gtggattcca tggccaatca actaaaatat ctggtggttg attaccatcc    60
caaaaca                                                              67

<210> SEQ ID NO 171
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 171
tatgttttat tctttagaat ggttaaaaga tcattctgaa tttttcaaa ctgttactga     60 atggc                                                                65

<210> SEQ ID NO 172
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 172
tcgagccatt cagtaacagt ttgaaaaaat tcagaatgat cttttaacca ttctaaagaa    60
taaaaca                                                              67

<210> SEQ ID NO 173
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 173
tatgcaattt atggaattac tgaaattctt taattctcca ggtgattctt ctcatcactt    60
cttac                                                                65

<210> SEQ ID NO 174
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 174
tcgagtaaga agtgatgaga agaatcacct ggagaattaa agaatttcag taattccata    60
aattgca                                                              67

<210> SEQ ID NO 175
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 175

```
tatgactaat gttgattgga tttctaataa ttgggaacat atgaaatctt tttttactga    60
agatc                                                                65

<210> SEQ ID NO 176
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 176
tcgagatctt cagtaaaaaa agatttcata tgttcccaat tattagaaat ccaatcaaca    60
ttagtca                                                              67

<210> SEQ ID NO 177
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 177
tatgccaaat gaaaaaccat atcaaatgca atcttggttt ccaccagatt ggccagttcc    60
atatc                                                                65

<210> SEQ ID NO 178
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 178
tcgagatatg gaactggcca atctggtgga aaccaagatt gcatttgata tggttttca    60 tttggca                                                              67

<210> SEQ ID NO 179
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 179
tatgtggtct catactgaat gggttccaca agtttggtgg aaaccaccaa atcatttta    60 tgttc                                                                65

<210> SEQ ID NO 180
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 180
tcgagaacat aaaaatgatt tggtggtttc caccaaactt gtggaaccca ttcagtatga    60
gaccaca                                                              67

<210> SEQ ID NO 181
<211> LENGTH: 65
<212> TYPE: DNA
<213> ORGANISM: Artificial Sequence
```

<220> FEATURE:
<223> OTHER INFORMATION: Oligonucleotide used in peptide construction

<400> SEQUENCE: 181
tatggttcca tgggaacatg atcatgattt atgggaaatt atttctcaag attggcatat    60
tgctc                                                               65

<210> SEQ ID NO 182
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 182
tcgagagcaa tatgccaatc ttgagaaata atttcccata aatcatgatc atgttcccat    60
ggaacca                                                             67

<210> SEQ ID NO 183
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 183
tatggtttta catttacaag atccacgtgg ttggtctaat tttccaccag gtgttttaga    60
attac                                                               65

<210> SEQ ID NO 184
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 184
tcgagtaatt ctaaaacacc tggtggaaaa ttagaccaac cacgtggatc ttgtaaatgt    60
aaaacca                                                             67

<210> SEQ ID NO 185
<211> LENGTH: 65
<212> TYPE: DNA
<213> ORGANISM: Artificial Sequence
<220> FEATURE:
<223> OTHER INFORMATION: Oligonucleotide used in peptide construction

<400> SEQUENCE: 185
tatgtggggt gaatggatta atgatgctca agttcacatg catgaaggtt ttatttctga    60
atctc                                                               65

<210> SEQ ID NO 186
<211> LENGTH: 67
<212> TYPE: DNA
<213> ORGANISM: Artificial Sequence
<220> FEATURE:
<223> OTHER INFORMATION: Oligonucleotide used in peptide construction

<400> SEQUENCE: 186
tcgagagatt cagaaataaa accttcatgc atgtgaactt gagcatcatt aatccattca    60
ccccaca                                                             67

```
<210> SEQ ID NO 187
<211> LENGTH: 67
<212> TYPE: DNA
<213> ORGANISM: Artificial Sequence
<220> FEATURE:
<223> OTHER INFORMATION: Oligonucleotide primer for PCR

<400> SEQUENCE: 187
acaaacaaac atatgggtgc acagaaagcg gccgcaaaaa aactcgaggg tggaggcggt        60
ggggaca                                                                 67

<210> SEQ ID NO 188
<211> LENGTH: 20
<212> TYPE: DNA
<213> ORGANISM: Artificial Sequence
<220> FEATURE:
<223> OTHER INFORMATION: Oligonucleotide primer for PCR

<400> SEQUENCE: 188
ggtcattact ggaccggatc                                                   20

<210> SEQ ID NO 189
<211> LENGTH: 25
<212> TYPE: DNA
<213> ORGANISM: Artificial Sequence
<220> FEATURE:
<223> OTHER INFORMATION: Oligonucleotide primer used in PCR

<400> SEQUENCE: 189
cgtacaggtt tacgcaagaa aatgg                                             25

<210> SEQ ID NO 190
<211> LENGTH: 66
<212> TYPE: DNA
<213> ORGANISM: Artificial Sequence
<220> FEATURE:
<223> OTHER INFORMATION: Oligonucleotide primer used in PCR

<400> SEQUENCE: 190
tttgttggat ccattactcg agttttttg cggccgcttt ctgtgcacca ccacctccac        60
ctttac                                                                  66

<210> SEQ ID NO 191
<211> LENGTH: 29
<212> TYPE: DNA
<213> ORGANISM: Artificial Sequence
<220> FEATURE:
<223> OTHER INFORMATION: Oligonucleotide primer used in PCR

<400> SEQUENCE: 191
caaacgaatg gatcctcatt aaagccaga                                         29

<210> SEQ ID NO 192
<211> LENGTH: 42
<212> TYPE: DNA
<213> ORGANISM: Artificial Sequence
<220> FEATURE:
<223> OTHER INFORMATION: Oligonucleotide primer used in PCR

<400> SEQUENCE: 192
ggtggtgcgg ccgcactcga gactgttgaa agttgtttag ca                          42

<210> SEQ ID NO 193
<211> LENGTH: 43
```

<212> TYPE: DNA
<213> ORGANISM: Artificial Sequence
<220> FEATURE:
<223> OTHER INFORMATION: Oligonucleotide primer used in PCR

<400> SEQUENCE: 193
aacacaaaag tgcacagggt ggaggtggtg gtgcggccgc act                    43

<210> SEQ ID NO 194
<211> LENGTH: 76
<212> TYPE: DNA
<213> ORGANISM: Artificial Sequence
<220> FEATURE:
<223> OTHER INFORMATION: Oligonucleotide for library preparation
<220> FEATURE:
<221> NAME/KEY: misc_feature
<222> LOCATION: (1)..(2)
<223> OTHER INFORMATION: N in positions 1-2 can be any nucleotide A, G,
    C or T
<220> FEATURE:
<221> NAME/KEY: misc_feature
<222> LOCATION: (4)..(5)
<223> OTHER INFORMATION: N in positions 4-5 can be any nucleotide A, G,
    C or T
<220> FEATURE:
<221> NAME/KEY: misc_feature
<222> LOCATION: (7)..(8)
<223> OTHER INFORMATION: N in positions 7-8 can be any nucleotide
    A, G, C or T
<220> FEATURE:
<221> NAME/KEY: misc_feature
<222> LOCATION: (10)..(11)
<223> OTHER INFORMATION: N in positions 10-11 can be any nucleotide
    A, G, C or T
<220> FEATURE:
<221> NAME/KEY: misc_feature
<222> LOCATION: (13)..(14)
<223> OTHER INFORMATION: N in positions 13-14 can be any nucleotide
    A, G, C or T
<220> FEATURE:
<221> NAME/KEY: misc_feature
<222> LOCATION: (16)..(17)
<223> OTHER INFORMATION: N in positions 16-17 can be any nucleotide
    A, G, C or T
<220> FEATURE:
<221> NAME/KEY: misc_feature
<222> LOCATION: (19)..(20)
<223> OTHER INFORMATION: N in positions 19-20 can be any nucleotide
    A, G, C or T
<220> FEATURE:
<221> NAME/KEY: misc_feature
<222> LOCATION: (28)..(29)
<223> OTHER INFORMATION: N in positions 28-29 can be any nucleotide
    A, G, C or T
<220> FEATURE:
<221> NAME/KEY: misc_feature
<222> LOCATION: (40)..(41)
<223> OTHER INFORMATION: N in positions 40-41 can be any nucleotide
    A, G, C or T
<220> FEATURE:
<221> NAME/KEY: misc_feature
<222> LOCATION: (43)..(44)
<223> OTHER INFORMATION: N in positions 43-44 can be any nucleotide
    A, G, C or T
<220> FEATURE:
<221> NAME/KEY: misc_feature
<222> LOCATION: (46)..(47)
<223> OTHER INFORMATION: N in positions 46-47 can be any nucleotide
    A, G, C or T
<220> FEATURE:
<221> NAME/KEY: misc_feature
<222> LOCATION: (49)..(50)
<223> OTHER INFORMATION: N in positions 49-50 can be any nucleotide
    A, G, C or T
<220> FEATURE:
<221> NAME/KEY: misc_feature
<222> LOCATION: (52)..(53)

```
<223> OTHER INFORMATION: N in positions 52-53 can be any nucleotide
     A, G, C or T
<220> FEATURE:
<221> NAME/KEY: misc_feature
<222> LOCATION: (55)..(56)
<223> OTHER INFORMATION: N in positions 55-56 can be any nucleotide
     A, G, C or T
<220> FEATURE:
<221> NAME/KEY: misc_feature
<222> LOCATION: (58)..(59)
<223> OTHER INFORMATION: N in positions 58-59 can be any nucleotide
     A, G, C or T
<220> FEATURE:
<221> NAME/KEY: misc_feature
<223> OTHER INFORMATION: K in positions 3, 6, 9, 12, 15, 18, 21, 30, 42,
     45, 48, 51, 54, 57, and 60 represents an equal representation of
     nucleotides G and T

<400> SEQUENCE: 194
nnknnknnkn nknnknnknn kctgcagnnk sartwtagcn nknnknnknn knnknnknnk     60
cattctctcg agatca                                                    76

<210> SEQ ID NO 195
<211> LENGTH: 91
<212> TYPE: DNA
<213> ORGANISM: Artificial Sequence
<220> FEATURE:
<223> OTHER INFORMATION: Oligonucleotide for library preparation
<220> FEATURE:
<221> NAME/KEY: misc_feature
<222> LOCATION: (16)..(17)
<223> OTHER INFORMATION: N in positions 16-17 can be any nucleotide A,
     G, C or T
<220> FEATURE:
<221> NAME/KEY: misc_feature
<222> LOCATION: (19)..(20)
<223> OTHER INFORMATION: N in positions 19-20 can be any nucleotide A,
     G, C or T
<220> FEATURE:
<221> NAME/KEY: misc_feature
<222> LOCATION: (22)..(23)
<223> OTHER INFORMATION: N in positions 22-23 can be any nucleotide A,
     G, C or T
<220> FEATURE:
<221> NAME/KEY: misc_feature
<222> LOCATION: (34)..(35)
<223> OTHER INFORMATION: N in positions 34-35 can be any nucleotide A,
     G, C or T
<220> FEATURE:
<221> NAME/KEY: misc_feature
<222> LOCATION: (55)..(56)
<223> OTHER INFORMATION: N in positions 55-56 can be any nucleotide A,
     G, C or T
<220> FEATURE:
<221> NAME/KEY: misc_feature
<222> LOCATION: (67)..(68)
<223> OTHER INFORMATION: N in positions 67-68 can be any nucleotide A,
     G, C or T
<220> FEATURE:
<221> NAME/KEY: misc_feature
<222> LOCATION: (70)..(71)
<223> OTHER INFORMATION: N in positions 70-71 can be any nucleotide A,
     G, C or T
<220> FEATURE:
<221> NAME/KEY: misc_feature
<222> LOCATION: (73)..(74)
<223> OTHER INFORMATION: N in positions 73-74 can be any nucleotide A,
     G, C or T
<220> FEATURE:
<221> NAME/KEY: misc_feature
<223> OTHER INFORMATION: K in positions 18, 21, 24, 36, 57 69, 72 and 75
     represents an equal representation of nucleotides G and T

<400> SEQUENCE: 195
cacagtgcac agggtnnknn knnkaaactg cagnnkgaat ttagcaccag cggcnnkccg     60
```

```
gatctgnnkn nknnkcattc tctcgagatc a                                      91
```

<210> SEQ ID NO 196
<211> LENGTH: 91
<212> TYPE: DNA
<213> ORGANISM: Artificial Sequence
<220> FEATURE:
<223> OTHER INFORMATION: Oligonucleotide for library preparation
<220> FEATURE:
<221> NAME/KEY: misc_feature
<222> LOCATION: (16)..(17)
<223> OTHER INFORMATION: N in positions 16-17 can be any nucleotide A,
      G, C or T
<220> FEATURE:
<221> NAME/KEY: misc_feature
<222> LOCATION: (19)..(20)
<223> OTHER INFORMATION: N in positions 19-20 can be any nucleotide A,
      G, C or T
<220> FEATURE:
<221> NAME/KEY: misc_feature
<222> LOCATION: (22)..(23)
<223> OTHER INFORMATION: N in positions 22-23 can be any nucleotide A,
      G, C or T
<220> FEATURE:
<221> NAME/KEY: misc_feature
<222> LOCATION: (25)..(26)
<223> OTHER INFORMATION: N in positions 25-26 can be any nucleotide A,
      G, C or T
<220> FEATURE:
<221> NAME/KEY: misc_feature
<222> LOCATION: (28)..(29)
<223> OTHER INFORMATION: N in positions 28-29 can be any nucleotide A,
      G, C or T
<220> FEATURE:
<221> NAME/KEY: misc_feature
<222> LOCATION: (31)..(32)
<223> OTHER INFORMATION: N in positions 31-32 can be any nucleotide A,
      G, C or T
<220> FEATURE:
<221> NAME/KEY: misc_feature
<222> LOCATION: (34)..(35)
<223> OTHER INFORMATION: N in positions 34-35 can be any nucleotide A,
      G, C or T
<220> FEATURE:
<221> NAME/KEY: misc_feature
<222> LOCATION: (55)..(56)
<223> OTHER INFORMATION: N in positions 55-56 can be any nucleotide A,
      G, C or T
<220> FEATURE:
<221> NAME/KEY: misc_feature
<222> LOCATION: (58)..(59)
<223> OTHER INFORMATION: N in positions 58-59 can be any nucleotide A,
      G, C or T
<220> FEATURE:
<221> NAME/KEY: misc_feature
<222> LOCATION: (61)..(62)
<223> OTHER INFORMATION: N in positions 61-62 can be any nucleotide A,
      G, C or T
<220> FEATURE:
<221> NAME/KEY: misc_feature
<222> LOCATION: (64)..(65)
<223> OTHER INFORMATION: N in positions 64-65 can be any nucleotide A,
      G, C or T
<220> FEATURE:
<221> NAME/KEY: misc_feature
<222> LOCATION: (67)..(68)
<223> OTHER INFORMATION: N in positions 67-68 can be any nucleotide A,
      G, C or T
<220> FEATURE:
<221> NAME/KEY: misc_feature
<222> LOCATION: (70)..(71)
<223> OTHER INFORMATION: N in positions 70-71 can be any nucleotide A,
      G, C or T
<220> FEATURE:
<221> NAME/KEY: misc_feature
<222> LOCATION: (73)..(74)
<223> OTHER INFORMATION: N in positions 73-74 can be any nucleotide A,

```
        G, C or T
<220> FEATURE:
<221> NAME/KEY: misc_feature
<223> OTHER INFORMATION: K in positions 18, 21, 24, 27, 30, 33, 36, 39,
      42, 45, 48, 51, 54, 57, 60, 63, 66, 69, 72 and 75 represents an
      equal representation of nucleotides G and T

<400> SEQUENCE: 196
cacagtgcac agggtnnknn knnknnknnk nnknnktgkt tkackgakga kggknnknnk      60
nnknnknnkn nknnkcattc tctcgagatc a                                    91

<210> SEQ ID NO 197
<211> LENGTH: 97
<212> TYPE: DNA
<213> ORGANISM: Artificial Sequence
<220> FEATURE:
<223> OTHER INFORMATION: Oligonucleotide for library preparation
<220> FEATURE:
<221> NAME/KEY: misc_feature
<222> LOCATION: (16)..(17)
<223> OTHER INFORMATION: N in positions 16-17 can be any nucleotide A,
      G, C or T
<220> FEATURE:
<221> NAME/KEY: misc_feature
<222> LOCATION: (79)..(80)
<223> OTHER INFORMATION: N in positions 79-80 can be any nucleotide A,
      G, C or T
<220> FEATURE:
<221> NAME/KEY: misc_feature
<223> OTHER INFORMATION: K in positions 18, 21, 24, 27, 30, 33, 36, 39,
      42, 45, 48, 51, 54, 57, 60, 63, 66, 69, 72, 75, 78 and 81
      represents an equal representation of nucleotides G and T

<400> SEQUENCE: 197
cacagtgcac agggtnnktt ktgkgakggk aakcakcckc ckgakatktt kgtkgaktgk      60
ccktgkaakc ckcckgtknn kcattctctc gagatca                              97

<210> SEQ ID NO 198
<211> LENGTH: 97
<212> TYPE: DNA
<213> ORGANISM: Artificial Sequence
<220> FEATURE:
<223> OTHER INFORMATION: Oligonucleotide for library preparation
<220> FEATURE:
<221> NAME/KEY: misc_feature
<222> LOCATION: (16)..(17)
<223> OTHER INFORMATION: N in positions 16-17 can be any nucleotide A,
      G, C or T
<220> FEATURE:
<221> NAME/KEY: misc_feature
<222> LOCATION: (79)..(80)
<223> THER INFORMATION: N in positions 79-80 can be any nucleotide A, G,
      C or T
<220> FEATURE:
<221> NAME/KEY: misc_feature
<223> OTHER INFORMATION: K in positions 18, 21, 24, 27, 30, 33, 36, 39,
      42, 45, 48, 51, 54, 57, 60, 63, 66, 69, 72, 75, 78 and 81
      represents an equal representation of nucleotides G and T

<400> SEQUENCE: 198
cacagtgcac agggtnnkac kgaktgkctk agkgakttkc ckttktakga kcaktakttk      60
ggkctkatkc ckcckggknn kcattctctc gagatca                              97

<210> SEQ ID NO 199
<211> LENGTH: 91
<212> TYPE: DNA
<213> ORGANISM: Artificial Sequence
<220> FEATURE:
<223> OTHER INFORMATION: Oligonucleotide for library preparation
<220> FEATURE:
```

```
<221> NAME/KEY: misc_feature
<222> LOCATION: (16)..(17)
<223> OTHER INFORMATION: N in positions 16-17 can be any nucleotide A,
      G, C or T
<220> FEATURE:
<221> NAME/KEY: misc_feature
<222> LOCATION: (19)..(20)
<223> OTHER INFORMATION: N in positions 19-20 can be any nucleotide A,
      G, C or T
<220> FEATURE:
<221> NAME/KEY: misc_feature
<222> LOCATION: (22)..(23)
<223> OTHER INFORMATION: N in positions 22-23 can be any nucleotide A,
      G, C or T
<220> FEATURE:
<221> NAME/KEY: misc_feature
<222> LOCATION: (34)..(35)
<223> OTHER INFORMATION: N in positions 34-35 can be any nucleotide A,
      G, C or T
<220> FEATURE:
<221> NAME/KEY: misc_feature
<222> LOCATION: (55)..(56)
<223> OTHER INFORMATION: N in positions 55-56 can be any nucleotide A,
      G, C or T
<220> FEATURE:
<221> NAME/KEY: misc_feature
<222> LOCATION: (67)..(68)
<223> OTHER INFORMATION: N in positions 67-68 can be any nucleotide A,
      G, C or T
<220> FEATURE:
<221> NAME/KEY: misc_feature
<222> LOCATION: (70)..(71)
<223> OTHER INFORMATION: N in positions 70-71 can be any nucleotide A,
      G, C or T
<220> FEATURE:
<221> NAME/KEY: misc_feature
<222> LOCATION: (73)..(74)
<223> THER INFORMATION: N in positions 73-74 can be any nucleotide A, G,
      C or T
<220> FEATURE:
<221> NAME/KEY: misc_feature
<223> OTHER INFORMATION: K in positions 18, 21, 24, 27, 30, 33, 36, 39,
      42, 45, 48, 51, 54, 57, 60, 63, 66, 69, 72 and 75 represents an
      equal representation of nucleotides G and T

<400> SEQUENCE: 199
cacagtgcac agggtnnknn knnkaakctk caknnkgakt tktckacktc kggknnkcck      60
gakctknnkn nknnkcattc tctcgagatc a                                    91

<210> SEQ ID NO 200
<211> LENGTH: 15
<212> TYPE: DNA
<213> ORGANISM: Artificial Sequence
<220> FEATURE:
<223> OTHER INFORMATION: Oligonucleotide primer for PCR

<400> SEQUENCE: 200
cacagtgcac agggt                                                      15

<210> SEQ ID NO 201
<211> LENGTH: 16
<212> TYPE: DNA
<213> ORGANISM: Artificial Sequence
<220> FEATURE:
<223> OTHER INFORMATION: Oligonucleotide primer for PCR

<400> SEQUENCE: 201
tgatctcgag agaatg                                                     16

<210> SEQ ID NO 202
<211> LENGTH: 22
<212> TYPE: PRT
```

```
<213> ORGANISM: Artificial Sequence
<220> FEATURE:
<223> OTHER INFORMATION: Therapeutically active peptide of randomly
      generated, non-naturally occurring sequence

<400> SEQUENCE: 202

Ala Gln Pro Thr Asp Gln Leu Gly Asp Trp Met Leu Asn Tyr Phe Arg
1               5                   10                  15

Leu Val Pro Pro Gly Thr
            20

<210> SEQ ID NO 203
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 203

Met Tyr Leu Asp Glu Trp Gln Trp Pro Pro Asp Val Phe Val Glu Trp
1               5                   10                  15

Pro Trp Lys Val Ser Val Asp
            20

<210> SEQ ID NO 204
<211> LENGTH: 22
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 204

Met Tyr Gln Lys Leu Gln Cys Glu Leu Ser Thr Ser Gly Cys Pro Asp
1               5                   10                  15

Leu Trp Arg Ala Leu Glu
            20

<210> SEQ ID NO 205
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 205

Ala Gln Leu Gln Ala Leu Leu Arg Glu Leu Pro Leu Tyr Glu Gln Phe
1               5                   10                  15

Phe Arg Leu Met Pro Pro Gly Tyr Leu Glu
            20                  25

<210> SEQ ID NO 206
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 206

Ala Gln Val Thr Asn Ile Leu Ser Gln Leu Pro Leu Trp Gln Gln Trp
1               5                   10                  15

Leu Gly Leu Met Pro Pro Gly Val Leu Glu
```

<210> SEQ ID NO 207
<211> LENGTH: 21
<212> TYPE: PRT
<213> ORGANISM: Artificial Sequence
<220> FEATURE:
<223> OTHER INFORMATION: Therapeutically active peptide of randomly
     generated, non-naturally occurring sequence

<400> SEQUENCE: 207

Met Ala Met Ala Gln Leu Gln Cys Glu Phe Ser Val Gln Gly Cys Pro
1               5                   10                  15

Ser Phe Val Leu Glu
            20

<210> SEQ ID NO 208
<211> LENGTH: 23
<212> TYPE: PRT
<213> ORGANISM: Artificial Sequence
<220> FEATURE:
<223> OTHER INFORMATION: Therapeutically active peptide of randomly
     generated, non-naturally occurring sequence

<400> SEQUENCE: 208

Met Leu His Asn Thr Leu Gln Cys Glu Phe Ser Thr Ser Gly Cys Pro
1               5                   10                  15

Asp Leu Pro Leu Gln Leu Glu
            20

<210> SEQ ID NO 209
<211> LENGTH: 23
<212> TYPE: PRT
<213> ORGANISM: Artificial Sequence
<220> FEATURE:
<223> OTHER INFORMATION: Therapeutically active peptide of randomly
     generated, non-naturally occurring sequence

<400> SEQUENCE: 209

Met Trp Gly Gln Lys Leu Gln Cys Glu Phe Ser Thr Ser Gly Cys Pro
1               5                   10                  15

Asp Leu Pro Lys Ala Leu Glu
            20

<210> SEQ ID NO 210
<211> LENGTH: 21
<212> TYPE: PRT
<213> ORGANISM: Artificial Sequence
<220> FEATURE:
<223> OTHER INFORMATION: Therapeutically active peptide of randomly
     generated, non-naturally occurring sequence

<400> SEQUENCE: 210

Met Ile Asp Trp Leu Ser Gln Asn Arg Leu Phe Glu Gln Tyr Phe Glu
1               5                   10                  15

Leu Ile Pro Pro Gly
            20

<210> SEQ ID NO 211
<211> LENGTH: 23
<212> TYPE: PRT
<213> ORGANISM: Artificial Sequence
<220> FEATURE:
<223> OTHER INFORMATION: Therapeutically active peptide of randomly
     generated, non-naturally occurring sequence

```
<400> SEQUENCE: 211

Gln Pro Thr Asp Gln Leu Gly Asp Trp Met Leu Asn Tyr Phe Arg Leu
1               5                   10                  15

Val Pro Pro Gly Thr Leu Glu
            20

<210> SEQ ID NO 212
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 212

Ala Gln Leu Ala Asp Leu Leu Ala Gln Leu Pro Met Trp Glu Gln Tyr
1               5                   10                  15

Leu Gly Leu Thr Pro Pro Ser Ser Leu Glu
            20                  25

<210> SEQ ID NO 213
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 213

Ala Gln Leu Arg Glu Leu Leu Ser Asp Leu Pro Met Trp Glu Gln Tyr
1               5                   10                  15

Phe Arg Leu Met Pro Pro Gly Tyr Leu Glu
            20                  25

<210> SEQ ID NO 214
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 214

Met Val Gln Arg Lys Leu Gln Cys Glu Phe Ser Thr Ser Gly Cys Pro
1               5                   10                  15

Asp Leu Thr Leu Leu Leu Glu
            20

<210> SEQ ID NO 215
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 215

Met Gly Pro Leu Val Leu Gln Cys Glu Phe Ser Gln Gly Gly Cys Pro
1               5                   10                  15

Thr Phe Leu Leu Glu
            20

<210> SEQ ID NO 216
<211> LENGTH: 24
```

<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 216

Ala Glu Gln Ser Gln Lys Leu Gln Cys Glu Phe Ser Thr Ser Gly Cys
1               5                   10                  15

Pro Asp Leu Pro Gln Met Leu Glu
            20

<210> SEQ ID NO 217
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 217

Met His Met Ser Asp Val Tyr Trp Pro Pro Asp Val Phe Val Glu Trp
1               5                   10                  15

Pro Trp Val Pro Gln Val Pro Leu Glu
            20                  25

<210> SEQ ID NO 218
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 218

Met Trp Val Gly Lys Gly Arg Leu Gln Cys Glu Ile Val Gly Gln Cys
1               5                   10                  15

Pro Gln Asn Pro Arg Trp Leu Leu Glu
            20                  25

<210> SEQ ID NO 219
<211> LENGTH: 24
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 219

Ala Gln Pro Thr Asp Gln Leu Gly Asp Trp Met Leu Asn Tyr Phe Arg
1               5                   10                  15

Leu Val Pro Pro Gly Thr Leu Glu
            20

<210> SEQ ID NO 220
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 220

Met Pro Glu Trp Lys Gly Tyr Trp Pro Pro Glu Val Phe Ile Glu Trp
1               5                   10                  15

-continued

Pro Trp Ser Pro Pro Val Gln Leu Glu
            20                  25

<210> SEQ ID NO 221
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 221

Pro Thr Asp Gln Leu Gly Asp Trp Met Leu Asn Tyr Phe Arg Leu Val
1               5                   10                  15

Pro Pro Gly Thr
            20

<210> SEQ ID NO 222
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 222

Met Ile Pro Gly Lys Leu Gln Cys Glu Leu Ser Ser Ser Gly Cys Pro
1               5                   10                  15

Asn Leu Gln Ala Met Leu Glu
            20

<210> SEQ ID NO 223
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 223

Met Asn Arg Met Gln Leu Gln Cys Glu Phe Ser Gln Ala Gly Cys Pro
1               5                   10                  15

Val Trp Ala Leu Glu
            20

<210> SEQ ID NO 224
<211> LENGTH: 24
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 224

Ala Gln Gln Ser Gln Lys Leu Gln Cys Glu Phe Ser Thr Ser Gly Cys
1               5                   10                  15

Pro Asp Leu Pro Leu Gln Leu Glu
            20

<210> SEQ ID NO 225
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

```
<400> SEQUENCE: 225

Ala Gln Gln Thr Glu Trp Leu Trp Ser Leu Pro Leu Val Gln Tyr
1               5                   10                  15

Phe Ser Leu Val Pro Pro Gly Tyr Leu Glu
            20                  25

<210> SEQ ID NO 226
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 226

Ala Gln Thr Gln Glu Trp Met Met Asn Leu Pro Leu Val Gln Tyr
1               5                   10                  15

Phe Gly Leu Thr Pro Pro Gly Met Leu Glu
            20                  25

<210> SEQ ID NO 227
<211> LENGTH: 19
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 227

Pro Thr Asp Gln Leu Gly Asp Trp Met Leu Asn Tyr Phe Arg Leu Val
1               5                   10                  15

Pro Pro Gly

<210> SEQ ID NO 228
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 228

Met Asp Glu Trp Gln Trp Pro Pro Asp Val Phe Val Glu Trp Pro Trp
1               5                   10                  15

Lys Val Ser Val Asp
            20

<210> SEQ ID NO 229
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 229

Met Ser Trp Gln Glu Gly Met Trp Pro Pro Glu Val Phe Val Glu Trp
1               5                   10                  15

Pro Trp Thr Ala His Asp Trp Leu Glu
            20                  25

<210> SEQ ID NO 230
<211> LENGTH: 26
```

```
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 230

Ala Gln Gln Gly Met Trp Pro Gly Ala Met Ser Leu Leu Glu Gln Tyr
1               5                   10                  15

Phe Ala Leu Thr Pro Pro Gly Leu Leu Glu
            20                  25

<210> SEQ ID NO 231
<211> LENGTH: 18
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 231

Asp Gln Leu Gly Asp Trp Met Leu Asn Tyr Phe Arg Leu Val Pro Pro
1               5                   10                  15

Gly Thr

<210> SEQ ID NO 232
<211> LENGTH: 22
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 232

Met Ile Asp Trp Leu Ser Gln Asn Arg Leu Phe Glu Gln Tyr Phe Glu
1               5                   10                  15

Leu Ile Pro Pro Gly Val
            20

<210> SEQ ID NO 233
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 233

Met Ser Gly Asp Lys Leu Gln Cys Glu Phe Ser Thr Ser Gly Cys Pro
1               5                   10                  15

Asp Leu Pro Ile Ser Leu Glu
            20

<210> SEQ ID NO 234
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 234

Met Gln Gln Gly Lys Leu Gln Cys Glu Leu Ser Thr Ala Gly Cys Pro
1               5                   10                  15

Glu Leu Leu Leu Pro Leu Glu
```

```
                     20

<210> SEQ ID NO 235
<211> LENGTH: 24
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 235

Ala Gln Gln Ser Gln Lys Leu Gln Cys Glu Phe Ser Thr Ser Gly Cys
1               5                   10                  15

Pro Asp Leu Pro Leu Met Leu Glu
            20

<210> SEQ ID NO 236
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 236

Ala Gln Asn Pro Gly His Leu Leu Asp Leu Pro Leu Phe Tyr Gln Tyr
1               5                   10                  15

Phe Gln Leu Met Pro Pro Gly Ile Leu Glu
            20                  25

<210> SEQ ID NO 237
<211> LENGTH: 22
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 237

Pro Thr Asp Gln Leu Gly Asp Trp Met Leu Asn Tyr Phe Arg Leu Val
1               5                   10                  15

Pro Pro Gly Thr Leu Glu
            20

<210> SEQ ID NO 238
<211> LENGTH: 22
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 238

Gln Thr Asp Trp Arg Trp Asp Leu Pro Phe Val Glu Asp Tyr Phe Arg
1               5                   10                  15

Leu Arg Pro Pro Gly Val
            20

<210> SEQ ID NO 239
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence
```

-continued

```
<400> SEQUENCE: 239

Ala Gln Met Ile Asp Trp Leu Ser Gln Asn Arg Leu Phe Glu Gln Tyr
1               5                   10                  15

Phe Glu Leu Ile Pro Pro Gly Val Leu Glu
            20                  25

<210> SEQ ID NO 240
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 240

Met Gln Leu Trp Asp Gly Lys Trp Pro Pro Glu Val Phe Val Glu Trp
1               5                   10                  15

Pro Trp Asn Pro Pro Val Gln
            20

<210> SEQ ID NO 241
<211> LENGTH: 24
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 241

Ala Gln Gln Ser Gln Lys Leu Gln Cys Glu Phe Ser Thr Ser Gly Cys
1               5                   10                  15

Pro Asp Leu Pro Gln Gln Leu Glu
            20

<210> SEQ ID NO 242
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 242

Met Val Glu Trp Gln Trp Cys Trp Phe Thr Glu Glu Gly Cys Pro Leu
1               5                   10                  15

Pro Leu Arg Leu Glu
            20

<210> SEQ ID NO 243
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 243

Met Trp Leu Phe Glu Gly Gln His Pro Pro Glu Val Leu Val Glu Trp
1               5                   10                  15

Pro Trp Val Trp Pro Val Ala Leu Glu
            20                  25

<210> SEQ ID NO 244
<211> LENGTH: 25
```

```
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 244

Met Arg Tyr Phe Glu Gly Asn Trp Pro Leu Asp Val Phe Val Asp Trp
1               5                   10                  15

Pro Trp Asn Pro Thr Val Asp Leu Glu
            20                  25

<210> SEQ ID NO 245
<211> LENGTH: 22
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 245

Met Gln Val Lys Leu Gln Cys Glu Phe Ser Thr Ser Gly Cys Pro Glu
1               5                   10                  15

Met His Arg Ile Leu Glu
            20

<210> SEQ ID NO 246
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 246

Met Gln Leu Gly Lys Leu Gln Cys Glu Leu Ser Thr Ala Gly Cys Pro
1               5                   10                  15

Asp Leu Pro Tyr Val Leu Glu
            20

<210> SEQ ID NO 247
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 247

Met Tyr Leu Asp Glu Trp Gln Trp Pro Pro Asp Val Phe Val Glu Trp
1               5                   10                  15

Pro Trp Lys Val Ser
            20

<210> SEQ ID NO 248
<211> LENGTH: 22
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 248

Met Thr Val Lys Leu Gln Cys Glu Phe Ser Thr Ser Gly Cys Pro Asp
1               5                   10                  15
```

Leu Ala Trp Gln Leu Glu
            20

<210> SEQ ID NO 249
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 249

Met Phe Arg Tyr Gln Leu Gln Cys Glu Leu Ser Ser Ser Gly Cys Pro
1               5                   10                  15

Asp Leu Asn Asn Ile Leu Glu
            20

<210> SEQ ID NO 250
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 250

Ala Gln Ala Arg Glu Trp Gln Thr Glu Leu Pro Phe Phe Glu Gln Tyr
1               5                   10                  15

Phe Ala Leu Met Pro Pro Gly Val Leu Glu
            20                  25

<210> SEQ ID NO 251
<211> LENGTH: 22
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 251

Gln Thr Asp Trp Leu Ser Asp Leu Pro Leu Leu Glu Gln Tyr Phe Arg
1               5                   10                  15

Leu Met Pro Pro Gly Val
            20

<210> SEQ ID NO 252
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 252

Met Ser Gln Ala Pro Leu Gln Cys Glu Tyr Ser Ser Ser Gly Cys Pro
1               5                   10                  15

Leu Trp Gln Leu Glu
            20

<210> SEQ ID NO 253
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

```
<400> SEQUENCE: 253

Ala Gln Leu Thr Asp Gln Leu Arg Leu Leu Pro Leu Tyr Leu Gln Tyr
1               5                   10                  15

Phe Ser Leu Ile Pro Pro Val Thr Leu Glu
            20                  25

<210> SEQ ID NO 254
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 254

Met Gln Ser Trp Asp Val Lys Trp Pro Pro Asp Val Phe Val Glu Trp
1               5                   10                  15

Pro Tyr Asn Pro Pro Ile Gln Leu Glu
            20                  25

<210> SEQ ID NO 255
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 255

Met Ile Lys Gln Lys Leu Gln Cys Glu Phe Ser Thr Ser Gly Cys Pro
1               5                   10                  15

Asp Leu Trp Met Ser Leu Glu
            20

<210> SEQ ID NO 256
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 256

Met His Glu Gln Lys Leu Gln Cys Glu Leu Ser Thr Ser Gly Cys Pro
1               5                   10                  15

Asp Leu Val Gln Met Leu Glu
            20

<210> SEQ ID NO 257
<211> LENGTH: 22
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 257

Met Gln Phe Lys Leu Gln Cys Glu Phe Ser Thr Ser Gly Cys Pro Asp
1               5                   10                  15

Leu Arg His Pro Leu Glu
            20

<210> SEQ ID NO 258
```

```
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 258

Ala Gln Met Gln Glu Leu Leu Arg Glu Leu Pro Leu Tyr Glu Gln Tyr
1               5                   10                  15

Met Ala Leu Met Pro Pro Gly Met Leu Glu
            20                  25

<210> SEQ ID NO 259
<211> LENGTH: 24
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 259

Ala Gln Gln Gln Gln Lys Leu Gln Cys Glu Phe Ser Thr Ser Gly Cys
1               5                   10                  15

Pro Asp Leu Pro Leu Met Leu Glu
            20

<210> SEQ ID NO 260
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 260

Ala Gln Gln Thr Asn Trp Cys Met Gly Ile Pro Tyr Cys Glu Gln Tyr
1               5                   10                  15

Phe Gly Leu Ser Pro His Gly Ile Leu Glu
            20                  25

<210> SEQ ID NO 261
<211> LENGTH: 21
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 261

Met Ala Ser Leu Thr Leu Gln Cys Glu Tyr Ser Gly Gln Gly Cys Pro
1               5                   10                  15

Lys Trp Pro Leu Glu
            20

<210> SEQ ID NO 262
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 262

Ala Gln Leu Ala Glu Trp Leu Gln Gln Ile Pro Leu Tyr Glu Gln Tyr
1               5                   10                  15
```

Phe Gly Leu Met Pro Pro Asp Leu Leu Glu
            20                  25

<210> SEQ ID NO 263
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 263

Met Glu Leu Ser Ala Arg Asn Trp Pro Pro Glu Ile Phe Glu Asp Trp
1               5                   10                  15

Pro Trp Gln Leu Pro Val Asp Leu Glu
            20                  25

<210> SEQ ID NO 264
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 264

Met Trp Met Thr Lys Leu Gln Cys Glu Phe Ser Ser His Gly Cys Pro
1               5                   10                  15

Gln Leu Thr Ser Met Leu Glu
            20

<210> SEQ ID NO 265
<211> LENGTH: 22
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 265

Ala Glu Val Glu Trp Gln Trp Cys Trp Phe Thr Glu Glu Gly Cys Pro
1               5                   10                  15

Leu Pro Leu Arg Leu Glu
            20

<210> SEQ ID NO 266
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 266

Met Tyr Leu Asp Glu Trp Gln Trp Pro Pro Asp Val Phe Val Glu Trp
1               5                   10                  15

Pro Trp Lys Val Ser Val Asp Leu Glu
            20                  25

<210> SEQ ID NO 267
<211> LENGTH: 23
<212> TYPE: PRT
<213> ORGANISM: Artificial Sequence
<220> FEATURE:
<223> OTHER INFORMATION: Therapeutically active peptide of randomly -continued generated, non-naturally occurring sequence

<400> SEQUENCE: 267

Met Gln Ser Asn Lys Leu Gln Cys Glu Phe Ser Thr Ser Gly Cys Pro
1               5                   10                  15

Glu Leu Leu Asp Leu Leu Glu
            20

<210> SEQ ID NO 268
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 268

Met Asn Val Gly Lys Leu Gln Cys Glu Leu Ser Thr Trp Gly Cys Pro
1               5                   10                  15

Val Pro Val Gln Gly Leu Glu
            20

<210> SEQ ID NO 269
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 269

Met Tyr Leu Trp Glu Gly Ile Trp Pro Ala Glu Val Phe Arg Glu Trp
1               5                   10                  15

Pro Trp Lys Pro Pro Asn Arg Leu Glu
            20                  25

<210> SEQ ID NO 270
<211> LENGTH: 25
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 270

Met Leu Phe Trp Gln Gly Asn Pro Pro Asp Val Phe Val Glu Trp
1               5                   10                  15

Pro Trp Gln Leu Pro Ala Ser Leu Glu
            20                  25

<210> SEQ ID NO 271
<211> LENGTH: 26
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 271

Ala Gln Asn Gly Asp Trp Met Arg Gly Leu Pro Phe Leu Glu Gln Tyr
1               5                   10                  15

Phe Gln Leu Leu Pro Pro Gly Val Leu Glu
            20                  25

```
<210> SEQ ID NO 272
<211> LENGTH: 23
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 272

Ala Gln Pro Thr Asp Gln Leu Gly Asp Trp Met Leu Asn Tyr Phe Arg
1               5                   10                  15

Leu Val Pro Pro Gly Thr Leu
            20

<210> SEQ ID NO 273
<211> LENGTH: 18
<212> TYPE: PRT
<213> ORGANISM: Artificial Sequence
<220> FEATURE:
<223> OTHER INFORMATION: Therapeutically active peptide of randomly
      generated, non-naturally occurring sequence

<400> SEQUENCE: 273

Trp Asp Met Cys His Phe Ser His Ala Ala Lys Leu Gln Ser Cys Phe
1               5                   10                  15

Pro His

<210> SEQ ID NO 274
<211> LENGTH: 12
<212> TYPE: PRT
<213> ORGANISM: Artificial Sequence
<220> FEATURE:
<223> OTHER INFORMATION: Consensus sequences from therapeutically active
      peptide of randomly generated, non-naturally occurring sequence
<220> FEATURE:
<221> NAME/KEY: misc_feature
<222> LOCATION: (1)..(1)
<223> OTHER INFORMATION: X in position 1 is equal to any amino acid.
<220> FEATURE:
<221> NAME/KEY: misc_feature
<222> LOCATION: (10)..(12)
<223> OTHER INFORMATION: X in positions 10, 11 and 12 is equal to any
      amino acid.
<220> FEATURE:
<221> NAME/KEY: misc_feature
<222> LOCATION: (4)..(4)
<223> OTHER INFORMATION: X at position 4 is equal to F or W.
<220> FEATURE:
<221> NAME/KEY: misc_feature
<222> LOCATION: (5)..(5)
<223> OTHER INFORMATION: X at position 5 is equal to S or T.

<400> SEQUENCE: 274

Xaa Cys Trp Xaa Xaa Glu Glu Gly Cys Xaa Xaa Xaa
1               5                   10

<210> SEQ ID NO 275
<211> LENGTH: 13
<212> TYPE: PRT
<213> ORGANISM: Artificial Sequence
<220> FEATURE:
<223> OTHER INFORMATION: Consensus sequences from therapeutically active
      peptide of randomly generated, non-naturally occurring sequence
<220> FEATURE:
<221> NAME/KEY: MISC_FEATURE
<222> LOCATION: (4)..(4)
<223> OTHER INFORMATION: X in position 4 is equal to any amino acids.
<220> FEATURE:
<221> NAME/KEY: MISC_FEATURE
<222> LOCATION: (5)..(5)
<223> OTHER INFORMATION: X at position 5 is equal to F or Y.
```

```
<220> FEATURE:
<221> NAME/KEY: MISC_FEATURE
<222> LOCATION: (7)..(8)
<223> OTHER INFORMATION: X in positions 7 and 8 is equal to any amino
      acid.
<220> FEATURE:
<221> NAME/KEY: MISC_FEATURE
<222> LOCATION: (12)..(13)
<223> OTHER INFORMATION: X in positions 12 and 13 is equal to any amino
      acid.

<400> SEQUENCE: 275

Leu Gln Cys Xaa Xaa Ser Xaa Xaa Gly Cys Pro Xaa Xaa
1               5                   10

<210> SEQ ID NO 276
<211> LENGTH: 18
<212> TYPE: PRT
<213> ORGANISM: Artificial Sequence
<220> FEATURE:
<223> OTHER INFORMATION: Consensus sequences from therapeutically active
      peptide of randomly generated, non-naturally occurring sequence
<220> FEATURE:
<221> NAME/KEY: MISC_FEATURE
<222> LOCATION: (1)..(3)
<223> OTHER INFORMATION: X in positions 1 through 3 is equal to any
      amino acid.
<220> FEATURE:
<221> NAME/KEY: MISC_FEATURE
<222> LOCATION: (5)..(11)
<223> OTHER INFORMATION: X in positions 5 through 11 is equal to any
      amino acid.
<220> FEATURE:
<221> NAME/KEY: MISC_FEATURE
<222> LOCATION: (16)..(18)
<223> OTHER INFORMATION: X in positions 16 through 18 is equal to any
      amino acid.

<400> SEQUENCE: 276

Xaa Xaa Xaa Cys Xaa Xaa Xaa Xaa Xaa Xaa Xaa Leu Gln Ser Cys Xaa
1               5                   10                  15

Xaa Xaa

<210> SEQ ID NO 277
<211> LENGTH: 14
<212> TYPE: PRT
<213> ORGANISM: Artificial Sequence
<220> FEATURE:
<223> OTHER INFORMATION: Peptide of randomly generated, non-naturally
      occurring sequence

<400> SEQUENCE: 277

Ile His Gly Cys Trp Phe Thr Glu Glu Gly Cys Val Trp Gln
1               5                   10

<210> SEQ ID NO 278
<211> LENGTH: 14
<212> TYPE: PRT
<213> ORGANISM: Artificial Sequence
<220> FEATURE:
<223> OTHER INFORMATION: Peptide of randomly generated, non-naturally
      occurring sequence

<400> SEQUENCE: 278

Leu Gln Met Cys Trp Phe Thr Glu Lys Gly Cys Glu Val Pro
1               5                   10

<210> SEQ ID NO 279
<211> LENGTH: 24
<212> TYPE: PRT
```

<213> ORGANISM: Artificial Sequence
<220> FEATURE:
<223> OTHER INFORMATION: Peptide of randomly generated, non-naturally
     occurring sequence

<400> SEQUENCE: 279

Ala Gln Gln Gln Gln Lys Leu Gln Cys Glu Phe Ser Thr Ser Gly Cys
1               5                   10                  15

Pro Asp Leu Pro Leu Met Leu Glu
            20

<210> SEQ ID NO 280
<211> LENGTH: 24
<212> TYPE: PRT
<213> ORGANISM: Artificial Sequence
<220> FEATURE:
<223> OTHER INFORMATION: Peptide of randomly generated, non-naturally
     occurring sequence

<400> SEQUENCE: 280

Ala Gln Gln Ser Gln Lys Leu Gln Cys Glu Phe Ser Thr Ser Gly Cys
1               5                   10                  15

Pro Asp Leu Pro Gln Met Leu Glu
            20

<210> SEQ ID NO 281
<211> LENGTH: 21
<212> TYPE: DNA
<213> ORGANISM: Artificial Sequence
<220> FEATURE:
<223> OTHER INFORMATION: PCR forward primer to amplify phage clones

<400> SEQUENCE: 281
gttagctcac tcattaggca c                                         21

<210> SEQ ID NO 282
<211> LENGTH: 21
<212> TYPE: DNA
<213> ORGANISM: Artificial Sequence
<220> FEATURE:
<223> OTHER INFORMATION: PCR reverse primer to amplify phage clones

<400> SEQUENCE: 282
gtaccgtaac actgagtttc g                                         21

<210> SEQ ID NO 283
<211> LENGTH: 21
<212> TYPE: DNA
<213> ORGANISM: Artificial Sequence
<220> FEATURE:
<223> OTHER INFORMATION: Primer used to sequence amplified inserts of
     phage clones

<400> SEQUENCE: 283
gtaccgtaac actgagtttc g                                         21

<210> SEQ ID NO 284
<211> LENGTH: 4
<212> TYPE: PRT
<213> ORGANISM: Artificial Sequence
<220> FEATURE:
<223> OTHER INFORMATION: Linker for peptide-FC linkage

<400> SEQUENCE: 284

Gly Gly Gly Gly
1

```
<210> SEQ ID NO 285
<211> LENGTH: 5
<212> TYPE: PRT
<213> ORGANISM: Artificial Sequence
<220> FEATURE:
<223> OTHER INFORMATION: Linker for peptide-FC linkage

<400> SEQUENCE: 285

Gly Gly Gly Gly Gly
1               5

<210> SEQ ID NO 286
<211> LENGTH: 7
<212> TYPE: PRT
<213> ORGANISM: Artificial Sequence
<220> FEATURE:
<223> OTHER INFORMATION: Linker for peptide-FC linkage

<400> SEQUENCE: 286

Gly Gly Gly Gly Gly Gly Gly
1               5
```